(12) United States Patent
Fayol et al.

(10) Patent No.: US 8,198,287 B2
(45) Date of Patent: Jun. 12, 2012

(54) SUBSTITUTED HETEROARYL PYRIDOPYRIMIDONE DERIVATIVES

(75) Inventors: Aude Fayol, Paris (FR); Thierry Gallet, Paris (FR); Alistair Lochead, Paris (FR); Mourad Saady, Paris (FR); Corinne Veronique, Paris (FR); Philippe Yaiche, Paris (FR)

(73) Assignees: Sanofi-Aventis, Paris (FR); Tanabe Pharma Corporation, Osaka (JP)

( * ) Notice: Subject to any disclaimer, the term of this patent is extended or adjusted under 35 U.S.C. 154(b) by 185 days.

(21) Appl. No.: 12/487,270

(22) Filed: Jun. 18, 2009

(65) Prior Publication Data

US 2009/0306088 A1    Dec. 10, 2009

Related U.S. Application Data

(63) Continuation of application No. PCT/IB2007/004409, filed on Dec. 20, 2007.

(30) Foreign Application Priority Data

Dec. 20, 2006 (EP) .................................. 06291995

(51) Int. Cl.
- *A01N 43/90* (2006.01)
- *A61K 31/519* (2006.01)
- *C07D 239/70* (2006.01)

(52) U.S. Cl. .................. 514/259.41; 544/282
(58) Field of Classification Search .......... None
See application file for complete search history.

(56) References Cited

FOREIGN PATENT DOCUMENTS

| DE | 2705582 | 8/1977 |
|---|---|---|
| WO | WO 96/14844 | 5/1996 |
| WO | WO03/027115 | 4/2003 |
| WO | WO2004/082577 | 9/2004 |
| WO | WO2004/083210 | 9/2004 |

OTHER PUBLICATIONS

Dorwald F. A. Side Reactions in Organic Synthesis, 2005, Wiley: VCH, Weinheim p. IX of Preface.*
Belyaev, A., et. al., A Novel Synthetic Route to N6-Methyl-L-Lysine and N5-Methyl-L-Omithine Via N3-Protected (S)-3-Aminolactamsl, Synthesis, (1991), pp. 417-420.
Bhat, R.V., et. al., Glycogen Synthase Kinase 3: A Drug Target for CNS Therapies, Journal of Neurochemistry, vol. 89, pp. 1313-1317 (2004).
Carmichael, J., et. al., Glycogen Synthase Kinase-3B Inhibitors Prevent Cellular Polyglutamine Toxicity Caused by the Huntington's Disease Mutation, The Journal of Biological Chemistry, vol. 277, No. 37, pp. 33791-33798, (2002).
Cohen, P., et. al., GSK3 Inhiibitors: Development and Therapeutic Potential, Nature Reviews, vol. 3, (2004) pp. 479-487.
Droucheau, E., et. al., *Plasmodium falciparum* Glycogen Synthase Kinase-3: Molecular Model, Expression, Intracellular Localisation and Selective Inhibitors, Biochimica et Biophysica Acta (2004), vol. 1697, pp. 181-196.
Hansen, D. W., et. al., 2-Iminohomopiperidinium Salts as Selective Inhibitors of Inducible Nitric Oxide Synthase (INOS), J. Med. Chem., (1998), vol. 41, pp. 1361-1366.
Koh, S., et al., Role of GSK-3B Activity in Motor Neuronal Cell Death Induced by G93A or A4V Mutant HSOD1 Gene, European Journal of Neuroscience, vol. 22, pp. 301-309, (2005).
Martinez, A., et. al., Glycogen Synthase Kinase 3 (GSK-3) Inhibitors as New Promising Drugs for Diabetes, Neurodegeneration, Cancer, and Inflammation, Med. Res. Rev., vol. 22, No. 4, pp. 373-384, (2002).
Meijer, L., et. al., Pharmacological Inhibitors of Glycogen Synthase Kinase 3, Trends in Pharmacological Sciences, vol. 25, No. 9, (2004), pp. 471-480.
Perez, M., et. al., Prion Peptide Induces Neuronal Cell Death Through a Pathway Involving Glycogen Synthase Kinase 3, Biochem. J., vol. 372, p. 129-136, (2003).
Sato, N., et. al., Maintenance of Pluripotency in Human and Mouse Embryonic Stem Cells Through Activation of Wnt Signaling by a Pharmacological GSK-3-Specific Inhibitor, Nature Medicine, vol. 10, No. 1, pp. 55-63, (2004).
Thenappan, A., et. al., An Expedient Synthesis of A-Fluoro-B-Ketoesters1, Tetrahedron Letters, vol. 30, No. 45 (1989) pp. 6113-6116.
Watanabe, N., et. al., Dirhodium(II) Tetrakis[3(S)-Phthalimido-2-Piperidinonate]: A Novel Dirhodium(II) Carboxamidate Catalyst for Asymmetric Cyclopropanation, Heterocycles, vol. 42, No. 2, (1996), pp. 537-542.

* cited by examiner

*Primary Examiner* — Jeffrey Murray
(74) *Attorney, Agent, or Firm* — Scully, Scott, Murphy & Presser, P.C.

(57) ABSTRACT

A pyrimidone derivative represented by formula (I) or a salt thereof, or a solvate thereof or a hydrate thereof are disclosed and claimed.

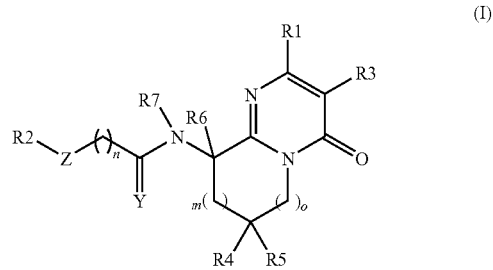

(I)

Wherein m, n, o, Y, Z, R1, R2, R3, R4, R5 R6 and R7 are as described herein. Also disclosed are the salts of compounds of formula (I). The invention relates also to a medicament comprising the said derivative or a salt thereof as an active ingredient which is used for preventive and/or therapeutic treatment of a neurodegenerative disease caused by abnormal activity of GSK3β, such as Alzheimer disease.

10 Claims, No Drawings

SUBSTITUTED HETEROARYL PYRIDOPYRIMIDONE DERIVATIVES

CROSS REFERENCE TO RELATED APPLICATIONS

This application is a continuation of International application No. PCT/IB2007/004,409, filed Dec. 20, 2007, which is incorporated herein by reference in its entirety; which claims the benefit of priority of European Patent Application No. 06291995.6, filed Dec. 20, 2006.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as p53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases and other pathologies where GSK3β is deregulated (Nature reviews Vol. 3, June 2004, p. 479-487; Trends in Pharmacological Sciences Vol. 25 No. 9, September 2004, p. 471-480; Journal of neurochemistry 2004, 89, 1313-1317; Medicinal Research Reviews, Vol. 22, No. 4, 373-384, 2002).

The neurodegenerative diseases include, in a non-limiting manner, Parkinson's disease, taupathies (e.g. Fronto temporal dementia, corticobasal degeneration, Pick's disease, progressive supranuclear palsy), Wilson's disease, Huntington's disease (The Journal of biological chemistry Vol. 277, No. 37, Issue of September 13, pp. 33791-33798, 2002), Prion disease (Biochem. J. 372, p. 129-136, 2003) and other dementia including vascular dementia; acute stroke and other traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of GSK3β results in neuronal differentiation of embryonic stem cells (ESC) and support the renewal of human and mouse ESCs and the maintenance of their pluripotency. This suggests that inhibitors of GSK3β could have applications in regenerative medicine (Nature Medicine 10, p. 55-63, 2004).

Inhibitors of GSK3β may also find application in the treatment of other nervous system disorders, such as bipolar disorders (manic-depressive illness). For example lithium has been used for more than 50 years as a mood stabilizer and the primary treatment for bipolar disorder. The therapeutic actions of lithium are observed at doses (1-2 mM) where it is a direct inhibitor of GSK3β. Although the mechanism of action of lithium is unclear, inhibitors of GSK3β could be used to mimic the mood stabilizing effects of lithium. Alterations in Akt-GSK3β signaling have also been implicated in the pathogenesis of schizophrenia.

In addition, inhibition of GSK3β could be useful in treating cancers, such as colorectal, prostate, breast, non-small lung carcinoma, thyroid cancer, T or B-cell leukemia and several virus-induced tumors. For example, the active form of GSK3β has been shown to be elevated in the tumors of colorectal cancer patients and inhibition of GSK3β in colorectal cancer cells activates p53-dependent apoptosis and antagonizes tumor growth. Inhibition of GSK3β also enhances TRAIL-induced apoptosis in prostate cancer cell lines. GSK3β also plays a role in the dynamics of the mitotic spindle and inhibitors of GSK3β prevent chromosome movement and lead to a stabilization of microtubules and a prometaphase-like arrest that is similar to that observed with low doses of Taxol. Other possible applications for GSK3β inhibitors include therapy for non-insulin dependent diabetes (such as diabetes type II), obesity and alopecia.

Inhibitors of human GSK3β may also inhibit pfGSK3, an ortholog of this enzyme found in *Plasmodium falciparum*, as a consequence they could be used for the treatment of malaria (Biochimica et Biophysica Acta 1697, 181-196, 2004).

Recently, both human genetics and animal studies have pointed out the role of Wnt/LPR5 pathway as a major regulator of bone mass accrual. Inhibition of GSK3β leads to the consequent activation of canonical Wnt signaling. Because deficient Wnt signaling has been implicated in disorders of reduced bone mass, GSK3β inhibitors may also be used for treating disorders of reduced bone mass, bone-related pathologies, osteoporosis.

According to recent data, GSK3β inhibitors might be used in the treatment or prevention of *Pemphigus vulgaris*.

Recent studies show that GSK3beta inhibitor treatment improves neutrophil and megakaryocyte recovery. Therefore, GSK3beta inhibitors will be useful for the treatment of neutropenia induced by cancer chemotherapy.

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides as an object of the invention the pyrimidone derivatives represented by formula (I) or salts thereof, solvates thereof or hydrates thereof:

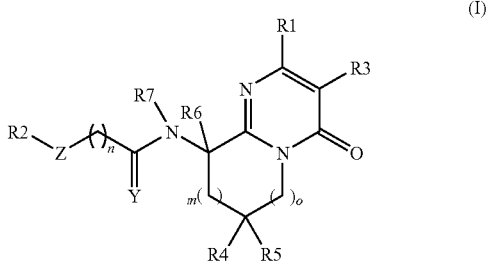

(I)

wherein:
Y represents two hydrogen atoms, a sulfur atom, an oxygen atom or a $C_{1-2}$ alkyl group and a hydrogen atom;
Z represents a bond, an oxygen atom, a nitrogen atom, a sulfur atom, a methylene group optionally substituted by one or two groups chosen from a $C_{1-6}$ alkyl group, a hydroxyl group, a $C_{1-6}$ alkoxy group, a $C_{1-2}$ perhalogenated alkyl group or an amino group;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a 4-15 membered heterocyclic group, this group being optionally substituted by 1 to 4 substituents selected from a $C_{1-6}$ alkyl group, a halogen atom, a $C_{1-2}$ perhalogenated alkyl group, a $C_{1-6}$ halogenated alkyl group, a hydroxyl group, a $C_{1-6}$ alkoxy group, a $C_{1-2}$ perhalogenated alkoxy group, a $C_{1-6}$ halogenated alkoxy group, a nitro, a cyano, an amino, a $C_{1-6}$ monoalkylamino group, a $C_{2-12}$ dialkylamino group, a S—($C_{1-6}$-alkyl) group, an 4-15 membered heterocyclic group, an aryl group, a O-aryl group or a S-aryl group, the above-mentioned groups being optionally substituted by 1 to 4 substituents selected from a $C_{1-6}$ alkyl group, a halogen atom, a ($C_{1-6}$) alkoxy group, a C(O) O($C_{1-6}$-alkyl) or a C(O)O (aryl) group;
R3 represents a hydrogen atom, a $C_{1-6}$ alkyl group or a halogen atom;
R4 and R5 represent, each independently, a hydrogen atom, a $C_{1-6}$ alkyl group, optionally substituted by 1 to 4 substituents selected from a halogen atom, a phenyl group, a hydroxyl group or a $C_{1-6}$ alkoxy group;
R6 represents a hydrogen atom, a $C_{1-6}$ alkyl group optionally substituted by a halogen atom or a cycloalkyl group, or a halogen atom;
R7 represents a hydrogen atom or a $C_{1-6}$ alkyl group;
n represents 0 to 3; m represents 0 to 1; o represents 0 to 2; in the form of a free base or of an addition salt with an acid.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as:

Non-insulin dependent diabetes (such as diabetes type II) and obesity; malaria, bipolar disorders (manic depressive illness); schizophrenia; alopecia or cancers such as colorectal, prostate, breast cancer, non-small cell lung carcinoma, thyroid cancer, T or B-cell leukemia, several virus-induced tumors. The medicament could also find an application in regenerative medicine, *Pemphigus vulgaris*, neutropenia and bone diseases.

As further embodiments of the present invention, there are provided the aforementioned medicament wherein the diseases are neurodegenerative diseases and are selected from the group consisting of Alzheimer's disease, Parkinson's disease, taupathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis; peripheral neuropathies; retinopathies and glaucoma, and the aforementioned medicament in the form of pharmaceutical composition containing the above substance as an active ingredient together with one or more pharmaceutical additives.

As further embodiments of the present invention, there are provided the aforementioned medicament wherein the bones diseases are osteoporosis.

The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched or cyclo alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like.

The 4-15 membered heterocyclic group represents an unsaturated, fully saturated or partially saturated mono- or polycyclic group (for example 4 to 10 members) containing carbons atoms and one to seven heteroatoms chosen from N, O, and S. Examples of heterocyclic groups include pyridine, pyrindine, pyrimidine, pyrazine, pyridazine, triazine, pyrrole, furan, thiophene, pyrazole, imidazole, triazole, tetrazole, oxazole, isoxazole, oxadiazole, thiazole, isothiazole, thiadiazole pyrrolopyrrole, pyrroloimidazole, pyrrolopyrazole, pyrrolotriazole, imidazoimidazole, imidazopyrazole, imidazotriazole, isoxazole, oxadiazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrimidotriazine, pyrazinopyrazine, pyrazinopyridazine, pyrazinotriazine, pyridazinopyridazine, pyridazinotriazine, indole, isoindole, benzimidazole, indazole, indolizine, benzofuran, isobenzofuran, benzothiophene, benzo[c]thiophene, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, tetrazolopyrimidine, pyrrolopyrazine, imidazopyrazine, pyrazolopyrazine, triazolopyrazine, tetrazolopyrazine, pyrrolopyridazine, imidazopyridazine, pyrazolopyridazine, triazolopyridazine, tetrazolopyridazine, pyrrolotriazine, imidazotriazine, pyrazolotriazine, triazolotriazine, tetrazolotriazine, furopyridine, furopyrimidine, furopyrazine, furopyridazine, furotriazine, oxazolopyridine, oxazolopyrimidine, oxazolopyrazine, oxazolopyridazine, oxazolotriazine, isoxazolopyridine, isoxazolopyrimidine, isoxazolopyrazine, isoxazolopyridazine, isoxazolotriazine, oxadiazolopyridine, oxadiazolopyrimidine, oxadiazolopyrazine, oxadiazolopyridazine, oxadiazolotriazine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, thiazolotriazine, isothiazolopyridine, isothiazolopyrimidine, isothiazolopyrazine, isothiazolopyridazine, isothiazolotriazine, thiadiazolopyridine, thiadiazolopyrimidine, thiadiazolopyrazine, thiadiazolopyridazine, thiadiazolotriazine, benzothiazole, benzoisothiazole, benzothiadiazole, benzotriazole, benzodioxepine, benzodioxane, benzodioxine, benzodioxole, diazepane. These heterocycles can exist also in a partially or fully saturated form, for example as an illustration dihydrobenzofuran, tetrahydroquinoline etc. . . .

The $C_{1-6}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl or alkoxy group represents an alkyl or alkoxy group wherein all the hydrogen atoms have been substituted by a halogen atom, for example a $CF_3$ or $C_2F_5$; O—$CF_3$ or O—$C_2F_5$;

The $C_{1-6}$ halogenated alkyl group represents an alkyl group wherein at least one hydrogen has been substituted by a halogen atom;

The $C_{1-6}$ halogenated alkoxy group represents an alkoxy group wherein at least one hydrogen of the alkyl group has not been substituted by an halogen atom;

The $C_{1-6}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group, isopentylamino group and the like;

The $C_{2-12}$ dialkylamino group represents an amino group substituted by two $C_{1-6}$ alkyl groups, for example, dimethylamino group, ethylmethylamino group, diethylamino group, methylpropylamino group and diisopropylamino group and the like;

The aryl group represents an aromatic mono or bicyclic ring (for example 6 to 10 members) such as phenyl, naphthyl, pentalene, azulene, heptalene, indacene, acenaphthylene, benzocyclooctatetraene, bicyclo[4.2.0]octa-1,3,5,7-tetraene, bicyclo[5.1.0]octa-1,3,5,7-tetraene, bicyclo[6.2.0]deca-1,3,5,7,9-pentaene.

A leaving group L represents a group which could be easily cleaved and substituted, such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N -bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention.

The pyrimidone derivatives represented by the aforementioned formula (I) may have one or more asymmetric carbon atoms. As for the stereochemistry of such asymmetric carbon atoms, they may independently be in either (R) and (S) configuration, and the derivative may exist as stereoisomers such as optical isomers, or diastereoisomers. Any stereoisomers in pure form, any mixtures of stereoisomers, racemates and the like fall within the scope of the present invention.

In a first embodiment of the invention, there is provided compounds wherein R1 represents an unsubstituted 4-pyridine ring or unsubstituted 4-pyrimidine ring, in the form of a free base or of an addition salt with an acid.

In a second embodiment of the invention, there is provided compounds of formula (I) wherein R4 and R5 represent a hydrogen atom, in the form of a free base or of an addition salt with an acid.

In a third embodiment of the invention, there is provided compounds of formula (I) wherein (m+o) represents 2 or 3, in the form of a free base or of an addition salt with an acid In an another embodiment of the invention, there is provided compounds of formula (I) wherein R2 represents a benzotriazole group, quinoxaline group, benzodioxepine group, benzodioxane group, benzodioxine group, benzodioxole group, indole group, pyridine group, pyrindine group, quinoline group, pyridazine group, isoquinoline group, pyrimidine group, naphthyridine group, imidazopyridine group, cinnoline group or benzofuran group and where the above-mentioned group being optionally substituted by 1 to 4 substituents selected from a $C_{1-6}$ alkyl group, a halogen atom, a $C_{1-6}$ alkoxy group, a $C_{1-2}$ perhalogenated alkoxy group, an amino, a S—$C_{1-6}$-alkyl group, a furan group, a thiophene group, a [1,4]diazepane, a phenyl group, a O-phenyl group or a S-phenyl group, the above-mentioned groups being optionally substituted by 1 to 4 substituents selected from a $C_{1-6}$ alkyl group, a halogen atom, a $C_{1-6}$ alkoxy group, or a C(O)O $C_{1-6}$-alkyl in the form of a free base or of an addition salt with an acid.

In another embodiment of the invention, there is provided compounds of formula (I) wherein R6 represents a hydrogen atom, a methyl or an ethyl group, in the form of a free base or of an addition salt with an acid.

In another embodiment of the invention, there is provided compounds of formula (I) wherein n represents 0, in the form of a free base or of an addition salt with an acid.

In another embodiment of the invention, there is provided compounds of formula (I) wherein Z represents a bond, in the form of a free base or of an addition salt with an acid.

In another embodiment of the invention, there is provided compounds of formula (I) wherein Y represents an oxygen atom, in the form of a free base or of an addition salt with an acid.

In another embodiment of the invention, there is provided compounds of formula (I) wherein R4 and R5 represent a hydrogen atom; (m+o) represents 2 or 3;
R2 represents a benzotriazole group, quinoxaline group, benzodioxepine group, benzodioxane group, benzodioxine group, benzodioxole group, indole group, pyridine group, pyrindine group, quinoline group, pyridazine group, isoquinoline group, pyrimidine group, naphthyridine group, imidazopyridine group, cinnoline group or benzofuran group and where the above-mentioned group being optionally substituted by 1 to 4 substituents selected from a $C_{1-6}$ alkyl group, a halogen atom, a $C_{1-6}$ alkoxy group, a $C_{1-2}$ perhalogenated alkoxy group, an amino, a S—$C_{1-6}$-alkyl group, a furan group, a thiophene group, a [1,4]diazepane, a phenyl group, a O-phenyl group or a S-phenyl group, the above-mentioned groups being optionally substituted by 1 to 4 substituents selected from a $C_{1-6}$ alkyl group, a halogen atom, a $C_{1-6}$ alkoxy group, or a C(O)O $C_{1-6}$-alkyl;
R6 represents a hydrogen atom, a methyl or an ethyl group;
n represents 0;
Z represents a bond, and
Y represents an oxygen atom, in the form of a free base or of an addition salt with an acid.

Examples of compounds of the present invention are shown in table 1, table 2 and table 3 hereinafter. However, the scope of the present invention is not limited by these compounds. The nomenclature is given according to IUPAC rules.

A further object of the present invention includes the group of compounds of table 1 of formula as defined hereunder:

1. (+/−)2,2-Dimethyl-2,3-dihydro-benzofuran-7-carboxylic acid (4-oxo-2-pyridin-4-yl-6,7,8,9-tetrahydro-4H-pyrido[1,2-a]pyrimidin-9-yl)-amide
2. (+/−)1-Methyl-1H-benzotriazole-5-carboxylic acid (4-oxo-2-pyridin-4-yl-6,7,8,9-tetrahydro-4H-pyrido[1,2-a]pyrimidin-9-yl)-amide
3. (+/−)Quinoxaline-6-carboxylic acid (4-oxo-2-pyridin-4-yl-6,7,8,9-tetrahydro-4H-pyrido[1,2-a]pyrimidin-9-yl)-amide
4. (+/−)2,3-Dihydro-benzofuran-7-carboxylic acid (4-oxo-2-pyrimidin-4-yl-6,7,8,9-tetrahydro-4H-pyrido[1,2-a]pyrimidin-9-yl)-amide
5. (+/−)2,2-Difluoro-benzo[1,3]dioxole-4-carboxylic acid (4-oxo-2-pyridin-4-yl-6,7,8,9-tetrahydro-4H-pyrido[1,2-a]pyrimidin-9-yl)-amide
6. (+/−)3,4-Dihydro-2H-benzo[b][1,4]dioxepine-6-carboxylic acid (4-oxo-2-pyridin-4-yl-6,7,8,9-tetrahydro-4H-pyrido[1,2-a]pyrimidin-9-yl)-amide
7. (+/−)Benzofuran-2-carboxylic acid (4-oxo-2-pyridin-4-yl-6,7,8,9-tetrahydro-4H-pyrido[1,2-a]pyrimidin-9-yl)-amide
8. (+/−)2,2-Dimethyl-2,3-dihydro-benzofuran-7-carboxylic acid (4-oxo-2-pyrimidin-4-yl-6,7,8,9-tetrahydro-4H-pyrido[1,2-a]pyrimidin-9-yl)-amide
9. (+/−)8-Amino-7-chloro-2,3-dihydro-benzo[1,4]dioxine-5-carboxylic acid (4-oxo-2-pyrimidin-4-yl-6,7,8,9-tetrahydro-4H-pyrido[1,2-a]pyrimidin-9-yl)-amide
10. (+/−)6-Fluoro-4H-benzo[1,3]dioxine-8-carboxylic acid (4-oxo-2-pyrimidin-4-yl-6,7,8,9-tetrahydro-4H-pyrido[1,2-a]pyrimidin-9-yl)-amide
11. (+/−)6-Fluoro-4H-benzo[1,3]dioxine-8-carboxylic acid (4-oxo-2-pyridin-4-yl-6,7,8,9-tetrahydro-4H-pyrido[1,2-a]pyrimidin-9-yl)-amide
12. (+/−)2,3-Dihydro-benzofuran-5-carboxylic acid (4-oxo-2-pyridin-4-yl-6,7,8,9-tetrahydro-4H-pyrido[1,2-a]pyrimidin-9-yl)-amide
13. (+/−)8-Amino-7-chloro-2,3-dihydro-benzo[1,4]dioxine-5-carboxylic acid (4-oxo-2-pyridin-4-yl-6,7,8,9-tetrahydro-4H-pyrido[1,2-a]pyrimidin-9-yl)-amide
14. (+/−)1-Methyl-1H-indole-3-carboxylic acid (4-oxo-2-pyridin-4-yl-6,7,8,9-tetrahydro-4H-pyrido[1,2-a]pyrimidin-9-yl)-amide
15. (+/−)2-Methoxy-N-(4-oxo-2-pyridin-4-yl-6,7,8,9-tetrahydro-4H-pyrido[1,2-a]pyrimidin-9-yl)-nicotinamide
16. (+/−)6,7-Dihydro-5H-[1]pyrindine-6-carboxylic acid (4-oxo-2-pyridin-4-yl-6,7,8,9-tetrahydro-4H-pyrido[1,2-a]pyrimidin-9-yl)-amide
17. (+/−)2-Methoxy-N-(4-oxo-2-pyrimidin-4-yl-6,7,8,9-tetrahydro-4H-pyrido[1,2-a]pyrimidin-9-yl)-nicotinamide
18. (+/−)2,6-Dimethoxy-N-(4-oxo-2-pyrimidin-4-yl-6,7,8,9-tetrahydro-4H-pyrido[1,2-a]pyrimidin-9-yl)-nicotinamide
19. (+/−)N-(4-Oxo-2-pyrimidin-4-yl-6,7,8,9-tetrahydro-4H-pyrido[1,2-a]pyrimidin-9-yl)-6-(2,2,2-trifluoro-ethoxy)-nicotinamide 20. (+/−)2-Fluoro-N-(4-oxo-2-pyrimidin-4-yl-6,7,8,9-tetrahydro-4H-pyrido[1,2-a]pyrimidin-9-yl)-nicotinamide
21. (+/−)N-(4-Oxo-2-pyrimidin-4-yl-6,7,8,9-tetrahydro-4H-pyrido[1,2-a]pyrimidin-9-yl)-2-p-tolyloxy-nicotinamide
22. (+/−)2-(4-Chloro-phenoxy)-N-(4-oxo-2-pyrimidin-4-yl-6,7,8,9-tetrahydro-4H-pyrido[1,2-a]pyrimidin-9-yl)-nicotinamide
23. (+/−)2-Methylsulfanyl-N-(4-oxo-2-pyrimidin-4-yl-6,7,8,9-tetrahydro-4H-pyrido[1,2-a]pyrimidin-9-yl)-nicotinamide
24. (+/−)5-Furan-2-yl-N-(4-oxo-2-pyrimidin-4-yl-6,7,8,9-tetrahydro-4H-pyrido[1,2-a]pyrimidin-9-yl)-nicotinamide
25. (+/−) 5-(2-Methoxy-phenyl)-N-(4-oxo-2-pyrimidin-4-yl-6,7,8,9-tetrahydro-4H-pyrido[1,2-a]pyrimidin-9-yl)-nicotinamide
26. (+/−)5-(3,4-Dimethoxy-phenyl)-N-(4-oxo-2-pyrimidin-4-yl-6,7,8,9-tetrahydro-4H-pyrido[1,2-a]pyrimidin-9-yl)-nicotinamide
27. (+/−)Quinoline-3-carboxylic acid (4-oxo-2-pyrimidin-4-yl-6,7,8,9-tetrahydro-4H-pyrido[1,2-a]pyrimidin-9-yl)-amide
28. (+/−)N-(4-Oxo-2-pyrimidin-4-yl-6,7,8,9-tetrahydro-4H-pyrido[1,2-a]pyrimidin-9-yl)-6-thiophen-2-yl-nicotinamide
29. (+/−)4-[5-(4-Oxo-2-pyrimidin-4-yl-6,7,8,9-tetrahydro-4H-pyrido[1,2-a]pyrimidin-9-ylcarbamoyl)-pyridin-2-yl]-[1,4]diazepane-1-carboxylic acid tert-butyl ester
30. (+/−) 6-Methyl-N-(4-oxo-2-pyrimidin-4-yl-6,7,8,9-tetrahydro-4H-pyrido[1,2-a]pyrimidin-9-yl)-nicotinamide
31. (+/−)N-(4-Oxo-2-pyrimidin-4-yl-6,7,8,9-tetrahydro-4H-pyrido[1,2-a]pyrimidin-9-yl)-2-propylsulfanyl-nicotinamide
32. (+/−)N-(4-Oxo-2-pyrimidin-4-yl-6,7,8,9-tetrahydro-4H-pyrido[1,2-a]pyrimidin-9-yl)-nicotinamide
33. (+/−)6-Chloro-N-(4-oxo-2-pyrimidin-4-yl-6,7,8,9-tetrahydro-4H-pyrido[1,2-a]pyrimidin-9-yl)-nicotinamide
34. (+/−)2-Methoxy-N-(9-methyl-4-oxo-2-pyrimidin-4-yl-6,7,8,9-tetrahydro-4H-pyrido[1,2-a]pyrimidin-9-yl)-nicotinamide
35. (+/−)4-Methoxy-pyridine-2-carboxylic acid (4-oxo-2-pyrimidin-4-yl-6,7,8,9-tetrahydro-4H-pyrido[1,2-a]pyrimidin-9-yl)-amide
36. (+/−)3,6-Dimethoxy-pyridazine-4-carboxylic acid (4-oxo-2-pyrimidin-4-yl-6,7,8,9-tetrahydro-4H-pyrido[1,2-a]pyrimidin-9-yl)-amide
37. (+/−)Pyridine-2-carboxylic acid (4-oxo-2-pyrimidin-4-yl-6,7,8,9-tetrahydro-4H-pyrido[1,2-a]pyrimidin-9-yl)-amide
38. (+/−)6-Methoxy-pyridine-2-carboxylic acid (4-oxo-2-pyrimidin-4-yl-6,7,8,9-tetrahydro-4H-pyrido[1,2-a]pyrimidin-9-yl)-amide
39. (+/−)4-Methoxy-quinoline-2-carboxylic acid (4-oxo-2-pyrimidin-4-yl-6,7,8,9-tetrahydro-4H-pyrido[1,2-a]pyrimidin-9-yl)-amide
40. (+/−)Isoquinoline-1-carboxylic acid (4-oxo-2-pyrimidin-4-yl-6,7,8,9-tetrahydro-4H-pyrido[1,2-a]pyrimidin-9-yl)-amide
41. (+/−)5-Chloro-2-methylsulfanyl-pyrimidine-4-carboxylic acid (9-methyl-4-oxo-2-pyrimidin-4-yl-6,7,8,9-tetrahydro-4H-pyrido[1,2-a]pyrimidin-9-yl)-amide
42. (+/−) [1,6]Naphthyridine-5-carboxylic acid (4-oxo-2-pyrimidin-4-yl-6,7,8,9-tetrahydro-4H-pyrido[1,2-a]pyrimidin-9-yl)-amide
43. (+/−)6-Chloro-pyridine-2-carboxylic acid (4-oxo-2-pyrimidin-4-yl-6,7,8,9-tetrahydro-4H-pyrido[1,2-a]pyrimidin-9-yl)-amide
44. (+/−)[1,5]Naphthyridine-2-carboxylic acid (4-oxo-2-pyrimidin-4-yl-6,7,8,9-tetrahydro-4H-pyrido[1,2-a]pyrimidin-9-yl)-amide
45. (+/−)6-(2,6-Dimethoxy-phenyl)-pyridine-2-carboxylic acid (4-oxo-2-pyrimidin-4-yl-6,7,8,9-tetrahydro-4H-pyrido[1,2-a]pyrimidin-9-yl)-amide
46. (+/−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide
47. (+/−)8-Amino-7-chloro-2,3-dihydro-benzo[1,4]dioxine-5-carboxylic acid (9-methyl-4-oxo-2-pyrimidin-4-yl-6,7,8,9-tetrahydro-4H-pyrido[1,2-a]pyrimidin-9-yl)-amide
48. (+/−)3,6-Dimethoxy-pyridazine-4-carboxylic acid (9-methyl-4-oxo-2-pyrimidin-4-yl-6,7,8,9-tetrahydro-4H-pyrido[1,2-a]pyrimidin-9-yl)-amide
49. (+/−)2,2-Dimethyl-2,3-dihydro-benzofuran-7-carboxylic acid (9-methyl-4-oxo-2-pyrimidin-4-yl-6,7,8,9-tetrahydro-4H-pyrido[1,2-a]pyrimidin-9-yl)-amide
50. (+/−)6-Fluoro-4H-benzo[1,3]dioxine-8-carboxylic acid (9-methyl-4-oxo-2-pyrimidin-4-yl-6,7,8,9-tetrahydro-4H-pyrido[1,2-a]pyrimidin-9-yl)-amide
51. (+/−)[1,5]Naphthyridine-2-carboxylic acid (9-methyl-4-oxo-2-pyrimidin-4-yl-6,7,8,9-tetrahydro-4H-pyrido[1,2-a]pyrimidin-9-yl)-amide
52. (+/−)2,3-Dihydro-benzofuran-7-carboxylic acid (9-methyl-4-oxo-2-pyrimidin-4-yl-6,7,8,9-tetrahydro-4H-pyrido[1,2-a]pyrimidin-9-yl)-amide
53. (+/−)Pyridine-2-carboxylic acid (9-methyl-4-oxo-2-pyrimidin-4-yl-6,7,8,9-tetrahydro-4H-pyrido[1,2-a]pyrimidin-9-yl)-amide
54. (+/−)6-Chloro-pyridine-2-carboxylic acid (9-methyl-4-oxo-2-pyrimidin-4-yl-6,7,8,9-tetrahydro-4H-pyrido[1,2-a]pyrimidin-9-yl)-amide
55. (+/−)[1,6]Naphthyridine-5-carboxylic acid (9-methyl-4-oxo-2-pyrimidin-4-yl-6,7,8,9-tetrahydro-4H-pyrido[1,2-a]pyrimidin-9-yl)-amide
56. (+/−)N-(9-Methyl-4-oxo-2-pyrimidin-4-yl-6,7,8,9-tetrahydro-4H-pyrido[1,2-a]pyrimidin-9-yl)-nicotinamide
57. (+/−)5-Bromo-benzofuran-2-carboxylic acid (9-methyl-4-oxo-2-pyrimidin-4-yl-6,7,8,9-tetrahydro-4H-pyrido[1,2-a]pyrimidin-9-yl)-amide
58. (+)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide
59. (−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide
60. (+)2-Methoxy-N-(9-methyl-4-oxo-2-pyrimidin-4-yl-6,7,8,9-tetrahydro-4H-pyrido[1,2-a]pyrimidin-9-yl)-nicotinamide
61. (−)2-Methoxy-N-(9-methyl-4-oxo-2-pyrimidin-4-yl-6,7,8,9-tetrahydro-4H-pyrido[1,2-a]pyrimidin-9-yl)-nicotinamide
62. (+)[1,5]Naphthyridine-2-carboxylic acid (4-oxo-2-pyrimidin-4-yl-6,7,8,9-tetrahydro-4H-pyrido[1,2-a]pyrimidin-9-yl)-amide
63. (−)[1,5]Naphthyridine-2-carboxylic acid (4-oxo-2-pyrimidin-4-yl-6,7,8,9-tetrahydro-4H-pyrido[1,2-a]pyrimidin-9-yl)-amide A further object of the present invention includes the group of compounds of table 2 of formula as defined hereunder:
1. (+/−)2,2-Dimethyl-2,3-dihydro-benzofuran-7-carboxylic acid (4-oxo-2-pyridin-4-yl-4,6,7,8-tetrahydro-pyrrolo[1,2-a]pyrimidin-8-yl)-amide
2. (+/−)1-Methyl-1H-benzotriazole-5-carboxylic acid (4-oxo-2-pyridin-4-yl-4,6,7,8-tetrahydro-pyrrolo[1,2-a]pyrimidin-8-yl)-amide 3. (+/−)8-Amino-7-chloro-2,3-dihydro-benzo[1,4]dioxine-5-carboxylic acid (4-oxo-2-pyridin-4-yl-4,6,7,8-tetrahydro-pyrrolo[1,2-a]pyrimidin-8-yl)-amide
4. (+/−)6-Fluoro-4H-benzo[1,3]dioxine-8-carboxylic acid (4-oxo-2-pyridin-4-yl-4,6,7,8-tetrahydro-pyrrolo[1,2-a]pyrimidin-8-yl)-amide
5. (+/−)Quinoxaline-6-carboxylic acid (4-oxo-2-pyridin-4-yl-4,6,7,8-tetrahydro-pyrrolo[1,2-a]pyrimidin-8-yl)-amide
6. (+/−)2,3-Dihydro-benzofuran-5-carboxylic acid (4-oxo-2-pyridin-4-yl-4,6,7,8-tetrahydro-pyrrolo[1,2-a]pyrimidin-8-yl)-amide
7. (+/−)1-Methyl-1H-indole-3-carboxylic acid (4-oxo-2-pyridin-4-yl-4,6,7,8-tetrahydro-pyrrolo[1,2-a]pyrimidin-8-yl)-amide
8. (+/−)5-Bromo-2,3-dihydro-benzofuran-7-carboxylic acid (4-oxo-2-pyridin-4-yl-4,6,7,8-tetrahydro-pyrrolo[1,2-a]pyrimidin-8-yl)-amide
9. (+/−)-2,3-Dihydro-benzofuran-2-carboxylic acid (4-oxo-2-pyridin-4-yl-4,6,7,8-tetrahydro-pyrrolo[1,2-a]pyrimidin-8-yl)-amide
10. (+/−)6,7-Dihydro-5H-[1]pyrindine-6-carboxylic acid (4-oxo-2-pyridin-4-yl-4,6,7,8-tetrahydro-pyrrolo[1,2-a]pyrimidin-8-yl)-amide
11. (+/−)Benzofuran-2-carboxylic acid (4-oxo-2-pyridin-4-yl-4,6,7,8-tetrahydro-pyrrolo[1,2-a]pyrimidin-8-yl)-amide
12. (+/−)[1,5]Naphthyridine-2-carboxylic acid (4-oxo-2-pyrimidin-4-yl-4,6,7,8-tetrahydro-pyrrolo[1,2-a]pyrimidin-8-yl)-amide
13. (+/−)2-Methoxy-N-(4-oxo-2-pyrimidin-4-yl-4,6,7,8-tetrahydro-pyrrolo[1,2-a]pyrimidin-8-yl)-nicotinamide
14. (+/−)5-Chloro-2-methylsulfanyl-pyrimidine-4-carboxylic acid (4-oxo-2-pyrimidin-4-yl-4,6,7,8-tetrahydro-pyrrolo[1,2-a]pyrimidin-8-yl)-amide
15. (+/−)Isoquinoline-1-carboxylic acid (4-oxo-2-pyrimidin-4-yl-4,6,7,8-tetrahydro-pyrrolo[1,2-a]pyrimidin-8-yl)-amide
16. (+/−)2-Methoxy-N-(4-oxo-2-pyridin-4-yl-4,6,7,8-tetrahydro-pyrrolo[1,2-a]pyrimidin-8-yl)-nicotinamide
17. (+/−)5-Chloro-2-methylsulfanyl-pyrimidine-4-carboxylic acid (4-oxo-2-pyridin-4-yl-4,6,7,8-tetrahydro-pyrrolo[1,2-a]pyrimidin-8-yl)-amide
18. (+/−)Isoquinoline-1-carboxylic acid (4-oxo-2-pyridin-4-yl-4,6,7,8-tetrahydro-pyrrolo[1,2-a]pyrimidin-8-yl)-amide
19. (+/−)Pyridine-2-carboxylic acid (4-oxo-2-pyrimidin-4-yl-4,6,7,8-tetrahydro-pyrrolo[1,2-a]pyrimidin-8-yl)-amide
20. (+/−)6-Chloro-pyridine-2-carboxylic acid (4-oxo-2-pyridin-4-yl-4,6,7,8-tetrahydro-pyrrolo[1,2-a]pyrimidin-8-yl)-amide
21. (+/−)[1,5]Naphthyridine-2-carboxylic acid (4-oxo-2-pyridin-4-yl-4,6,7,8-tetrahydro-pyrrolo[1,2-a]pyrimidin-8-yl)-amide A further object of the present invention includes the group of compounds of table 3 of formula as defined hereunder:

1. (+/−)8-Amino-7-chloro-2,3-dihydro-benzo[1,4]dioxine-5-carboxylic acid (4-oxo-2-pyrimidin-4-yl-4,6,7,8,9,10-hexahydro-pyrimido[1,2-a]azepin-10-yl)-amide
2. (+/−)2-Methoxy-N-(4-oxo-2-pyrimidin-4-yl-4,6,7,8,9,10-hexahydro-pyrimido[1,2-a]azepin-10-yl)-nicotinamide
3. (+/−)5-Bromo-2,3-dihydro-benzofuran-7-carboxylic acid (4-oxo-2-pyrimidin-4-yl-4,6,7,8,9,10-hexahydro-pyrimido[1,2-a]azepin-10-yl)-amide
4. (+/−)6-Fluoro-4H-benzo[1,3]dioxine-8-carboxylic acid (4-oxo-2-pyrimidin-4-yl-4,6,7,8,9,10-hexahydro-pyrimido[1,2-a]azepin-10-yl)-amide
5. (+/−)5-Chloro-2,3-dihydro-benzofuran-7-carboxylic acid (4-oxo-2-pyrimidin-4-yl-4,6,7,8,9,10-hexahydro-pyrimido[1,2-a]azepin-10-yl)-amide
6. (+/−)2,3-Dihydro-benzofuran-7-carboxylic acid (4-oxo-2-pyrimidin-4-yl-4,6,7,8,9,10-hexahydro-pyrimido[1,2-a]azepin-10-yl)-amide
7. (+/−)2,2-Dimethyl-2,3-dihydro-benzofuran-7-carboxylic acid (4-oxo-2-pyrimidin-4-yl-4,6,7,8,9,10-hexahydro-pyrimido[1,2-a]azepin-10-yl)-amide
8. (+/−)2,2-Dimethyl-2,3-dihydro-benzofuran-7-carboxylic acid (4-oxo-2-pyrimidin-4-yl-4,6,7,8,9,10-hexahydro-pyrimido[1,2-a]azepin-10-yl)-amide
9. (+/−)6-Fluoro-4H-benzo[1,3]dioxine-8-carboxylic acid (4-oxo-2-pyridin-4-yl-4,6,7,8,9,10-hexahydro-pyrimido[1,2-a]azepin-10-yl)-amide
10. (+/−)5-Chloro-2,3-dihydro-benzofuran-7-carboxylic acid (4-oxo-2-pyridin-4-yl-4,6,7,8,9,10-hexahydro-pyrimido[1,2-a]azepin-10-yl)-amide
11. (+/−)2,3-Dihydro-benzofuran-7-carboxylic acid (4-oxo-2-pyridin-4-yl-4,6,7,8,9,10-hexahydro-pyrimido[1,2-a]azepin-10-yl)-amide
12. (+/−)8-Amino-7-chloro-2,3-dihydro-benzo[1,4]dioxine-5-carboxylic acid (4-oxo-2-pyridin-4-yl-4,6,7,8,9,10-hexahydro-pyrimido[1,2-a]azepin-10-yl)-amide
13. (+/−)2-Methoxy-N-(4-oxo-2-pyridin-4-yl-4,6,7,8,9,10-hexahydro-pyrimido[1,2-a]azepin-10-yl)-nicotinamide
14. (+)2-Methoxy-N-(4-oxo-2-pyridin-4-yl-4,6,7,8,9,10-hexahydro-pyrimido[1,2-a]azepin-10-yl)-nicotinamide
15. (−)2-Methoxy-N-(4-oxo-2-pyridin-4-yl-4,6,7,8,9,10-hexahydro-pyrimido[1,2-a]azepin-10-yl)-nicotinamide
16. (+/−)2,6-Dimethoxy-N-(4-oxo-2-pyridin-4-yl-4,6,7,8,9,10-hexahydro-pyrimido[1,2-a]azepin-10-yl)-nicotinamide
17. (+/−)N-(4-Oxo-2-pyridin-4-yl-4,6,7,8,9,10-hexahydro-pyrimido[1,2-a]azepin-10-yl)-6-(2,2,2-trifluoro-ethoxy)-nicotinamide
18. (+/−)2-Fluoro-N-(4-oxo-2-pyridin-4-yl-4,6,7,8,9,10-hexahydro-pyrimido[1,2-a]azepin-10-yl)-nicotinamide
19. (+/−)2-Methylsulfanyl-N-(4-oxo-2-pyridin-4-yl-4,6,7,8,9,10-hexahydro-pyrimido[1,2-a]azepin-10-yl)-nicotinamide
20. (+/−)N-(4-Oxo-2-pyridin-4-yl-4,6,7,8,9,10-hexahydro-pyrimido[1,2-a]azepin-10-yl)-2-p-tolyloxy-nicotinamide
21. (+/−)2-(4-Chloro-phenoxy)-N-(4-oxo-2-pyridin-4-yl-4,6,7,8,9,10-hexahydro-pyrimido[1,2-a]azepin-10-yl)-nicotinamide
22. (+/−)3H-Imidazo[4,5-b]pyridine-6-carboxylic acid (4-oxo-2-pyridin-4-yl-4,6,7,8,9,10-hexahydro-pyrimido[1,2-a]azepin-10-yl)-amide
23. (+/−)N-(4-Oxo-2-pyridin-4-yl-4,6,7,8,9,10-hexahydro-pyrimido[1,2-a]azepin-10-yl)-6-thiophen-2-yl-nicotinamide
24. (+/−)6-Methyl-N-(4-oxo-2-pyridin-4-yl-4,6,7,8,9,10-hexahydro-pyrimido[1,2-a]azepin-10-yl)-nicotinamide
25. (+/−)5-Furan-2-yl-N-(4-oxo-2-pyridin-4-yl-4,6,7,8,9,10-hexahydro-pyrimido[1,2-a]azepin-10-yl)-nicotinamide
26. (+/−)5-(2-Methoxy-phenyl)-N-(4-oxo-2-pyridin-4-yl-4,6,7,8,9,10-hexahydro-pyrimido[1,2-a]azepin-10-yl)-nicotinamide
27. (+/−)5-(3,4-Dimethoxy-phenyl)-N-(4-oxo-2-pyridin-4-yl-4,6,7,8,9,10-hexahydro-pyrimido[1,2-a]azepin-10-yl)-nicotinamide 28. (+/−)Quinoline-3-carboxylic acid (4-oxo-2-pyridin-4-yl-4,6,7,8,9,10-hexahydro-pyrimido[1,2-a]azepin-10-yl)-amide
29. (+/−)4-[5-(4-Oxo-2-pyridin-4-yl-4,6,7,8,9,10-hexahydro-pyrimido[1,2-a]azepin-10-ylcarbamoyl)-pyridin-2-yl]-[1,4]diazepane-1-carboxylic acid tert-butyl ester
30. (+/−)5-(4-Bromo-phenyl)-N-(4-oxo-2-pyridin-4-yl-4,6,7,8,9,10-hexahydro-pyrimido[1,2-a]azepin-10-yl)-nicotinamide
31. (+/−)N-(4-Oxo-2-pyridin-4-yl-4,6,7,8,9,10-hexahydro-pyrimido[1,2-a]azepin-10-yl)-nicotinamide
32. (+/−)6-Chloro-N-(4-oxo-2-pyridin-4-yl-4,6,7,8,9,10-hexahydro-pyrimido[1,2-a]azepin-10-yl)-nicotinamide
33. (+/−)2-Chloro-N-(4-oxo-2-pyridin-4-yl-4,6,7,8,9,10-hexahydro-pyrimido[1,2-a]azepin-10-yl)-nicotinamide
34. (+/−)N-(4-Oxo-2-pyridin-4-yl-4,6,7,8,9,10-hexahydro-pyrimido[1,2-a]azepin-10-yl)-2-phenylsulfanyl-nicotinamide
35. (+/−)N-(4-Oxo-2-pyridin-4-yl-4,6,7,8,9,10-hexahydro-pyrimido[1,2-a]azepin-10-yl)-2-propylsulfanyl-nicotinamide
36. (+/−)2-(4-Chloro-phenylsulfanyl)-N-(4-oxo-2-pyridin-4-yl-4,6,7,8,9,10-hexahydro-pyrimido[1,2-a]azepin-10-yl)-nicotinamide
37. (+/−)4-Methyl-2-phenyl-pyrimidine-5-carboxylic acid (4-oxo-2-pyrimidin-4-yl-4,6,7,8,9,10-hexahydro-pyrimido[1,2-a]azepin-10-yl)-amide
38. (+/−)Pyrimidine-5-carboxylic acid (4-oxo-2-pyrimidin-4-yl-4,6,7,8,9,10-hexahydro-pyrimido[1,2-a]azepin-10-yl)-amide
39. (+/−)5-Chloro-2-methylsulfanyl-pyrimidine-4-carboxylic acid (4-oxo-2-pyrimidin-4-yl-4,6,7,8,9,10-hexahydro-pyrimido[1,2-a]azepin-10-yl)-amide
40. (+/−)Pyridazine-4-carboxylic acid (4-oxo-2-pyrimidin-4-yl-4,6,7,8,9,10-hexahydro-pyrimido[1,2-a]azepin-10-yl)-amide
41. (+/−)6-Phenyl-pyrimidine-4-carboxylic acid (4-oxo-2-pyrimidin-4-yl-4,6,7,8,9,10-hexahydro-pyrimido[1,2-a]azepin-10-yl)-amide
42. (+/−)Cinnoline-4-carboxylic acid (4-oxo-2-pyrimidin-4-yl-4,6,7,8,9,10-hexahydro-pyrimido[1,2-a]azepin-10-yl)-amide
43. (+/−)3,6-Dimethoxy-pyridazine-4-carboxylic acid (4-oxo-2-pyrimidin-4-yl-4,6,7,8,9,10-hexahydro-pyrimido[1,2-a]azepin-10-yl)-amide
44. (+/−)Isoquinoline-1-carboxylic acid (4-oxo-2-pyridin-4-yl-4,6,7,8,9,10-hexahydro-pyrimido[1,2-a]azepin-10-yl)-amide
45. (+/−)3-Phenyl-cinnoline-4-carboxylic acid (4-oxo-2-pyrimidin-4-yl-4,6,7,8,9,10-hexahydro-pyrimido[1,2-a]azepin-10-yl)-amide
46. (+/−)[1,6]Naphthyridine-5-carboxylic acid (4-oxo-2-pyridin-4-yl-4,6,7,8,9,10-hexahydro-pyrimido[1,2-a]azepin-10-yl)-amide
47. (+/−)[1,5]Naphthyridine-2-carboxylic acid (4-oxo-2-pyridin-4-yl-4,6,7,8,9,10-hexahydro-pyrimido[1,2-a]azepin-10-yl)-amide
48. (+/−)[1,6]Naphthyridine-5-carboxylic acid (4-oxo-2-pyrimidin-4-yl-4,6,7,8,9,10-hexahydro-pyrimido[1,2-a]azepin-10-yl)-amide
49. (+/−)[1,5]Naphthyridine-2-carboxylic acid (4-oxo-2-pyrimidin-4-yl-4,6,7,8,9,10-hexahydro-pyrimido[1,2-a]azepin-10-yl)-amide
50. (+/−)4-Methoxy-quinoline-2-carboxylic acid (4-oxo-2-pyrimidin-4-yl-4,6,7,8,9,10-hexahydro-pyrimido[1,2-a]azepin-10-yl)-amide
51. (+/−)Isoquinoline-1-carboxylic acid (4-oxo-2-pyrimidin-4-yl-4,6,7,8,9,10-hexahydro-pyrimido[1,2-a]azepin-10-yl)-amide
52. (+/−)Pyridine-2-carboxylic acid (4-oxo-2-pyrimidin-4-yl-4,6,7,8,9,10-hexahydro-pyrimido[1,2-a]azepin-10-yl)-amide
53. (+/−)6-Chloro-pyridine-2-carboxylic acid (4-oxo-2-pyrimidin-4-yl-4,6,7,8,9,10-hexahydro-pyrimido[1,2-a]azepin-10-yl)-amide
54. (+/−)4-Methoxy-pyridine-2-carboxylic acid (4-oxo-2-pyrimidin-4-yl-4,6,7,8,9,10-hexahydro-pyrimido[1,2-a]azepin-10-yl)-amide
55. (+/−)3,5-Difluoro-pyridine-2-carboxylic acid (4-oxo-2-pyrimidin-4-yl-4,6,7,8,9,10-hexahydro-pyrimido[1,2-a]azepin-10-yl)-amide
56. (+/−)6-(2,6-Dimethoxy-phenyl)-pyridine-2-carboxylic acid (4-oxo-2-pyrimidin-4-yl-4,6,7,8,9,10-hexahydro-pyrimido[1,2-a]azepin-10-yl)-amide
57. (+/−)4-Methyl-2-phenyl-pyrimidine-5-carboxylic acid (4-oxo-2-pyridin-4-yl-4,6,7,8,9,10-hexahydro-pyrimido[1,2-a]azepin-10-yl)-amide
58. (+/−)3-Phenyl-cinnoline-4-carboxylic acid (4-oxo-2-pyridin-4-yl-4,6,7,8,9,10-hexahydro-pyrimido[1,2-a]azepin-10-yl)-amide
59. (+/−)3,6-Dimethoxy-pyridazine-4-carboxylic acid (4-oxo-2-pyridin-4-yl-4,6,7,8,9,10-hexahydro-pyrimido[1,2-a]azepin-10-yl)-amide
60. (+/−)2-Methyl-4-phenyl-pyrimidine-5-carboxylic acid (4-oxo-2-pyridin-4-yl-4,6,7,8,9,10-hexahydro-pyrimido[1,2-a]azepin-10-yl)-amide
61. (+/−)6-Phenyl-pyrimidine-4-carboxylic acid (4-oxo-2-pyridin-4-yl-4,6,7,8,9,10-hexahydro-pyrimido[1,2-a]azepin-10-yl)-amide
62. (+/−)6-(2-Fluoro-phenyl)-pyridine-2-carboxylic acid (4-oxo-2-pyrimidin-4-yl-4,6,7,8,9,10-hexahydro-pyrimido[1,2-a]azepin-10-yl)-amide
63. (+/−)2,6-Dimethoxy-N-(4-oxo-2-pyrimidin-4-yl-4,6,7,8,9,10-hexahydro-pyrimido[1,2-a]azepin-10-yl)-nicotinamide
64. (+/−)N-(4-Oxo-2-pyrimidin-4-yl-4,6,7,8,9,10-hexahydro-pyrimido[1,2-a]azepin-10-yl)-6-(2,2,2-trifluoro-ethoxy)-nicotinamide
65. (+/−)2-Fluoro-N-(4-oxo-2-pyrimidin-4-yl-4,6,7,8,9,10-hexahydro-pyrimido[1,2-a]azepin-10-yl)-nicotinamide
66. (+/−)5-Furan-2-yl-N-(4-oxo-2-pyrimidin-4-yl-4,6,7,8,9,10-hexahydro-pyrimido[1,2-a]azepin-10-yl)-nicotinamide
67. (+/−)6-Methoxy-pyridine-2-carboxylic acid (4-oxo-2-pyrimidin-4-yl-4,6,7,8,9,10-hexahydro-pyrimido[1,2-a]azepin-10-yl)-amide
68. (+/−)Quinoline-3-carboxylic acid (4-oxo-2-pyrimidin-4-yl-4,6,7,8,9,10-hexahydro-pyrimido[1,2-a]azepin-10-yl)-amide
69. (+/−)4-[5-(4-Oxo-2-pyrimidin-4-yl-4,6,7,8,9,10-hexahydro-pyrimido[1,2-a]azepin-10-ylcarbamoyl)-pyridin-2-yl]-[1,4]diazepane-1-carboxylic acid tert-butyl ester
70. (+/−)5-(2-Methoxy-phenyl)-N-(4-oxo-2-pyrimidin-4-yl-4,6,7,8,9,10-hexahydro-pyrimido[1,2-a]azepin-10-yl)-nicotinamide
71. (+/−)5-(3,4-Dimethoxy-phenyl)-N-(4-oxo-2-pyrimidin-4-yl-4,6,7,8,9,10-hexahydro-pyrimido[1,2-a]azepin-10-yl)-nicotinamide
72. (+/−)2,6-Dimethoxy-pyrimidine-4-carboxylic acid (4-oxo-2-pyrimidin-4-yl-4,6,7,8,9,10-hexahydro-pyrimido[1,2-a]azepin-10-yl)-amide 73. (+/−)5-Bromo-2-methylsulfanyl-pyrimidine-4-carboxylic acid (4-oxo-2-pyrimidin-4-yl-4,6,7,8,9,10-hexahydro-pyrimido[1,2-a]azepin-10-yl) -amide
74. (+/−)[1,5]Naphthyridine-2-carboxylic acid (10-methyl-4-oxo-2-pyrimidin-4-yl-4,6,7,8,9,10-hexahydro-pyrimido[1,2-a]azepin-10-yl)-amide
75. (+/−)6-Methoxy-pyridine-2-carboxylic acid (10-methyl-4-oxo-2-pyrimidin-4-yl-4,6,7,8,9,10-hexahydro-pyrimido[1,2-a]azepin-10-yl)-amide
76. (+/−)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl) -amide
77. (+/−)N-(10-Ethyl-4-oxo-2-pyrimidin-4-yl-4,6,7,8,9,10-hexahydro-pyrimido[1,2-a]azepin-10-yl)-2-methoxy-nicotinamide
78. (+/−)2-Methoxy-N-(10-methyl-4-oxo-2-pyridin-4-yl-4,6,7,8,9,10-hexahydro-pyrimido[1,2-a]azepin-10-yl)-nicotinamide
79. (+/−)2,3-Dihydro-benzofuran-7-carboxylic acid (10-methyl-4-oxo-2-pyridin-4-yl-4,6,7,8,9,10-hexahydro-pyrimido[1,2-a]azepin-10-yl)-amide
80. (+/−)2-Methoxy-N-(10-methyl-4-oxo-2-pyrimidin-4-yl-4,6,7,8,9,10-hexahydro-pyrimido[1,2-a]azepin-10-yl)-nicotinamide
81. (+/−)2,3-Dihydro-benzofuran-7-carboxylic acid (10-methyl-4-oxo-2-pyrimidin-4-yl-4,6,7,8,9,10-hexahydro-pyrimido[1,2-a]azepin-10-yl)-amide
82. (+/−)6-Fluoro-4H-benzo[1,3]dioxine-8-carboxylic acid (10-methyl-4-oxo-2-pyrimidin-4-yl-4,6,7,8,9,10-hexahydro-pyrimido[1,2-a]azepin-10-yl) -amide
83. (+/−)2,6-Dimethoxy-N-(10-methyl-4-oxo-2-pyrimidin-4-yl-4,6,7,8,9,10-hexahydro-pyrimido[1,2-a]azepin-10-yl)-nicotinamide
84. (+/−)Pyridine-2-carboxylic acid (10-methyl-4-oxo-2-pyrimidin-4-yl-4,6,7,8,9,10-hexahydro-pyrimido[1,2-a]azepin-10-yl)-amide
85. (+/−)4-Methoxy-pyridine-2-carboxylic acid (10-methyl-4-oxo-2-pyrimidin-4-yl-4,6,7,8,9,10-hexahydro-pyrimido[1,2-a]azepin-10-yl)-amide
86. (+/−)3,6-Dimethoxy-pyridazine-4-carboxylic acid (10-methyl -4-oxo-2-pyrimidin-4-yl-4,6,7,8,9,10-hexahydro-pyrimido[1,2-a]azepin-10-yl)-amide
87. (+/−)6-Chloro-pyridine-2-carboxylic acid (10-methyl-4-oxo-2-pyrimidin-4-yl-4,6,7,8,9,10-hexahydro-pyrimido[1,2-a]azepin-10-yl)-amide
88. (+/−)8-Amino-7-chloro-2,3-dihydro-benzo[1,4]dioxine-5-carboxylic acid (10-methyl-4-oxo-2-pyrimidin-4-yl-4,6,7,8,9,10-hexahydro-pyrimido[1,2-a]azepin-10-yl)-amide
89. (+/−)5-Bromo-2-methylsulfanyl-pyrimidine-4-carboxylic acid (10-methyl-4-oxo-2-pyrimidin-4-yl-4,6,7,8,9,10-hexahydro-pyrimido[1,2-a]azepin-10-yl)-amide
90. (+/−)6-Bromo-pyridine-2-carboxylic acid (10-methyl-4-oxo-2-pyrimidin-4-yl-4,6,7,8,9,10-hexahydro-pyrimido[1,2-a]azepin-10-yl)-amide
91. (+/−)3,5-Difluoro-pyridine-2-carboxylic acid (10-methyl-4-oxo-2-pyrimidin-4-yl-4,6,7,8,9,10-hexahydro-pyrimido[1,2-a]azepin-10-yl)-amide
92. (+/−)2,2-Dimethyl-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide
93. (+/−)4-Methoxy-pyridine-2-carboxylic acid (10-ethyl-4-oxo-2-pyrimidin-4-yl-4,6,7,8,9,10-hexahydro-pyrimido[1,2-a]azepin-10-yl)-amide
94. (+/−)5-Chloro-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl) -amide
95. (+/−)5-Chloro-2-methylsulfanyl-pyrimidine-4-carboxylic acid (10-methyl-4-oxo-2-pyrimidin-4-yl-4,6,7,8,9,10-hexahydro-pyrimido[1,2-a]azepin-10-yl)-amide
96. (+/−)8-Amino-7-chloro-2,3-dihydro-benzo[1,4]dioxine-5-carboxylic acid (10-ethyl-4-oxo-2-pyrimidin-4-yl-4,6,7,8,9,10-hexahydro-pyrimido[1,2-a]azepin-10-yl)-amide
97. (+/−)3,6-Dimethoxy-pyridazine-4-carboxylic acid (10-ethyl -4-oxo-2-pyrimidin-4-yl-4,6,7,8,9,10-hexahydro-pyrimido[1,2-a]azepin-10-yl)-amide
98. (+/−)6-Fluoro-4H-benzo[1,3]dioxine-8-carboxylic acid (10-ethyl-4-oxo-2-pyrimidin-4-yl-4,6,7,8,9,10-hexahydro-pyrimido[1,2-a]azepin-10-yl) -amide
99. (+/−)N-(10-Ethyl-4-oxo-2-pyrimidin-4-yl-4,6,7,8,9,10-hexahydro-pyrimido[1,2-a]azepin-10-yl)-2,6-dimethoxy-nicotinamide
100. (+/−)N-(3-Bromo-4-oxo-2-pyrimidin-4-yl-4,6,7,8,9,10-hexahydro-pyrimido[1,2-a]azepin-10-yl)-2-methoxy-nicotinamide
101. (+/−)6-Chloro-pyridine-2-carboxylic acid (10-ethyl-4-oxo-2-pyrimidin-4-yl-4,6,7,8,9,10-hexahydro-pyrimido[1,2-a]azepin-10-yl)-amide
102. (+)2,6-Dimethoxy-N-(4-oxo-2-pyrimidin-4-yl-4,6,7,8,9,10-hexahydro-pyrimido[1,2-a]azepin-10-yl)-nicotinamide
103. (−)2,6-Dimethoxy-N-(4-oxo-2-pyrimidin-4-yl-4,6,7,8,9,10-hexahydro-pyrimido[1,2-a]azepin-10-yl)-nicotinamide
104. (+)2-Methoxy-N-(10-methyl-4-oxo-2-pyrimidin-4-yl -4,6,7,8,9,10-hexahydro-pyrimido[1,2-a]azepin-10-yl)-nicotinamide
105. (−)2,6-Dimethoxy-N-(10-methyl-4-oxo-2-pyrimidin-4-yl-4,6,7,8,9,10-hexahydro-pyrimido[1,2-a]azepin-10-yl)-nicotinamide
106. (−)2-Methoxy-N-(10-methyl-4-oxo-2-pyrimidin-4-yl -4,6,7,8,9,10-hexahydro-pyrimido[1,2-a]azepin-10-yl)-nicotinamide
107. (+)2,6-Dimethoxy-N-(10-methyl-4-oxo-2-pyrimidin-4-yl-4,6,7,8,9,10-hexahydro-pyrimido[1,2-a]azepin-10-yl)-nicotinamide
108. (−)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl) -amide
109. (+)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl) -amide As a further object, the present invention concerns also methods for preparing the pyrimidone compounds represented by the aforementioned formula (I).

These compounds can be prepared, for example, according to methods explained below.

Preparation Method

Pyrimidone compounds represented by the aforementioned formula (I), may be prepared according to the method described in the scheme 1.

Scheme 1

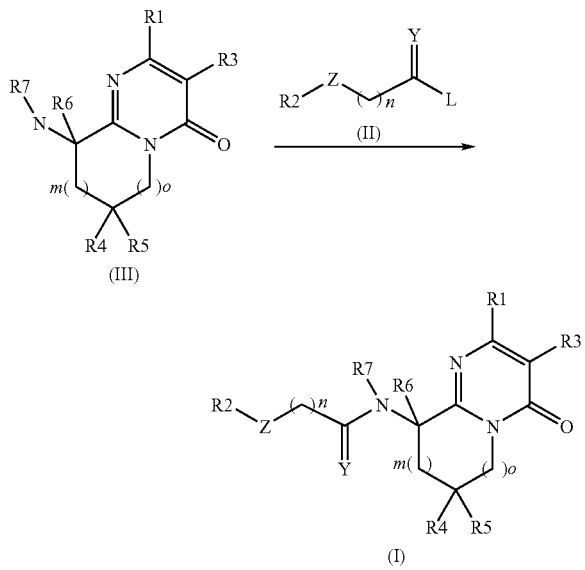

(In the above scheme the definition of R1, R2, R3, R4, R5, R6, R7, m, n, o, Y and Z are the same as those already described for compound of formula (I)).

Following this method, the pyrimidone derivative represented by the above formula (III), wherein R1, R3, R4, R5, R6, R7, m and o are as defined for compound of formula (I), is allowed to react with a base such as triethylamine, sodium carbonate or potassium carbonate in a solvent such as tetrahydrofuran, N-methylpyrrolidone, N,N-dimethylacetamide or chloroform at a suitable temperature ranging from 0 to 130° C. under ordinary air, then with a compound of formula (II), wherein R2, X, Y and n are as defined for compound of formula (I) and L represents a leaving group preferably chlorine, bromide or mesyl group or hydroxyl group, to obtain the compound of the aforementioned formula (I).

Alternatively compounds of formula (I) wherein Y represents two hydrogen atoms may be prepared by reductive amination of a compound of formula (II) wherein Y represents an oxygen atom and L represents a hydrogen atom according to well known methods to one skilled in the art.

Compound of formula (II) is commercially available or may be synthesized according to well-known methods to one skilled in the art.

Compound of formula (III) may be prepared according to the method defined in scheme 2.

Scheme 2

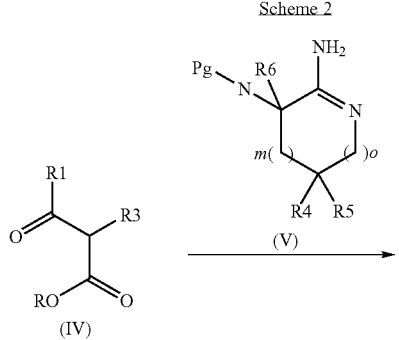

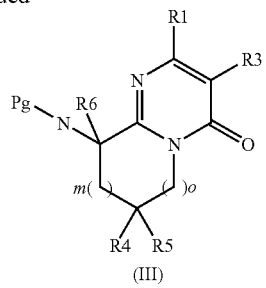

(In the above scheme the definition of R1, R3, R4, R5, R6, m and o are the same as already described.)

According to this method, the 3-ketoester of formula (IV), wherein R1 and R3 are as defined for compound of formula (I), R is an alkyl group such as for example methyl or ethyl and Pg is a suitable protecting group such as for example a phthalimido group, is allowed to react with a compound of formula (V) wherein R4, R5, R6, m and o are as defined for compound of formula (I). The reaction may be carried out in the presence of a base such as potassium carbonate, in an alcoholic solvent such as methanol, ethanol and the like or without, at a suitable temperature ranging from 25° to 140° C. under ordinary air.

Additionally compound of formula (III) wherein R3 represents a hydrogen atom may be halogenated in order to give compounds of formula (III) wherein R3 is a halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (IV) wherein R3 represents a fluorine atom may be obtained by analogy to the method described in Tetrahedron Letters, Vol. 30, No. 45, pp 6113-6116, 1989.

In addition, compounds of formula (IV) wherein R3 represents a hydrogen atom may be obtained by analogy to the method described in patent DE 2705582.

As a further object, the present invention concerns also the compounds of formula (III) as intermediates of compounds of formula (I).

Compound of formula (IV) is commercially available or may be synthesized according to well-known methods to one skilled in the art.

For example compounds of formula (IV), wherein R1 represents a pyridine ring or a pyrimidine ring, optionally substituted by a $C_{1-6}$ alkyl group, $C_{1-6}$ alkoxy group or a halogen atom, can be prepared by reacting respectively an isonicotinic acid or a pyrimidine-carboxylic acid, optionally substituted by a $C_{1-6}$ alkyl group, $C_{1-6}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compound of formula (V) may be synthesized according to well-known methods of one skilled in the art.

For example compound of formula (V), wherein m, o, R4, R5 and R6 are as defined for compound of formula (I) and Pg is a suitable protecting group such as for example a phthalimido group, may be prepared according to the method defined in scheme 3, starting from compound of formula (VI). The conditions which may be used are given in the chemical examples.

Scheme 3

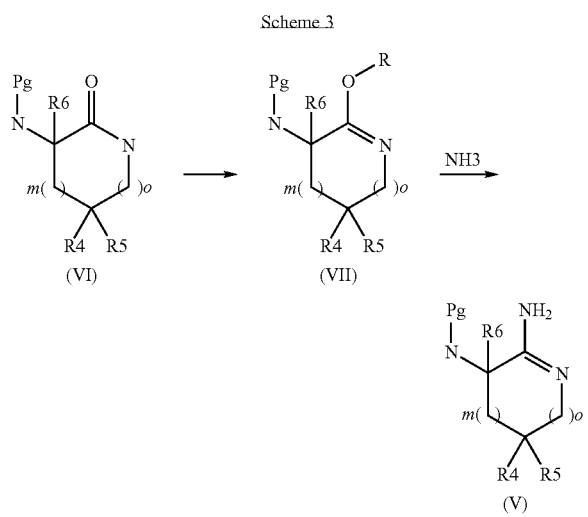

Compound of formula (VI) may be synthesized by analogy to the methods described in Heterocycles (1996), 42 (2), 537-42, Enantiomer (2001), 6 (5), 275-279 and Synthesis (1991), (5), 417-20.

Compound of formula (VII) and formula (V) may be synthesized according to the method described in WO9614844.

Alternatively compounds of formula (III) wherein R1, R3, R4, R5, R7, m and o are as defined for compound of formula (I) and R6 represents a hydrogen atom, a $C_{1-6}$ alkyl group optionally substituted by a halogen atom or a cycloalkyl group, may be prepared according to the method defined in scheme 4, starting from compound of formula (IV).

Scheme 4

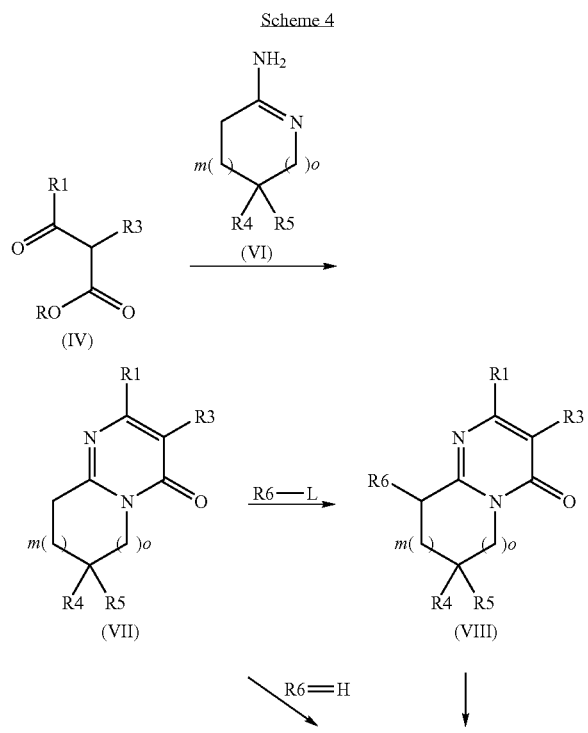

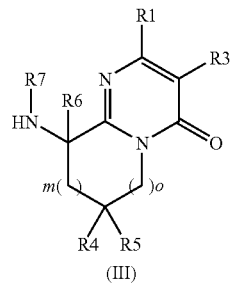

According to this method, the 3-ketoester of formula (IV), wherein R1 and R3 are as defined for compound of formula (I), R is an alkyl group such as for example methyl or ethyl is allowed to react with a compound of formula (VI) wherein R4, R5, m and o are as defined for compound of formula (I) to afford the compound of formula (VII). The reaction may be carried out in the presence of a base such as potassium carbonate, in an alcoholic solvent such as methanol, ethanol and the like or without, at a suitable temperature ranging from 25° to 140° C. under ordinary air.

The compound of formula (VII) wherein R1, R3, R4, R5, m and o are as defined for compound of formula (I) can be deprotonated with strong base (such as lithium bis(trimethylsilyl)amide or lithium diisopropyl amide) and the resultant anion reacted with suitable electrophiles R6-L wherein R6 represents a $C_{1-6}$ alkyl group optionally substituted by a halogen atom or a cycloalkyl group and L represents a leaving group such as bromine, iodine or mesyl group to afford the compound of formula (VIII).

The compound of formula (VIII) wherein R1, R3, R4, R5, m and o are as defined for the compound of formula (I) and R6 represents a $C_{1-6}$ alkyl group optionally substituted by a halogen atom or a cycloalkyl group, can be deprotonated with strong base (such as lithium bis(trimethylsilyl)amide or lithium diisopropyl amide) followed by addition of an electrophilic nitrogen source such as trisyl azide to afford compound of formula (III) wherein R1, R3, R4, R5, R7, m and o are as defined for compound of formula (I) and R6 represents a $C_{1-6}$ alkyl group optionally substituted by a halogen atom or a cycloalkyl group.

The compound of formula (VII) wherein R1, R3, R4, R5, m and o are as defined for the compound of formula (I) can be deprotonated with strong base (such as lithium bis(trimethylsilyl)amide or lithium diisopropyl amide) followed by addition of an electrophilic nitrogen source such as trisyl azide to afford compound of formula (III) wherein R1, R3, R4, R5, R7, m and o are as defined for compound of formula (I) and R6 represents a hydrogen.

The conditions which may be used are given in the chemical examples.

Compound of formula (VI) may be synthesized according to the methods described in WO96/14844 and Journal of Medicinal Chemistry (1998), 41(9), 1361-1366.

In the above reactions protection or deprotection of a functional group may sometimes be necessary. A suitable protecting group Pg can be chosen depending on the type of the functional group, and a method described in the literature may be applied. Examples of protecting groups, of protection and deprotection methods are given for example in Protective groups in Organic Synthesis Greene et al., (John Wiley & Sons, Inc., New York)4th Ed. 2007.

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, taupathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound No. 2 of Table 1

(+/−)1-Methyl-N-(4-oxo-2-pyridin-4-yl-6,7,8,9-tetrahydro-4H-pyrido[1,2-a]pyrimidin-9-yl)-1H-1,2,3-benzotriazole-5-carboxamide 1.1 (+/−)2-(2-Methoxy-3,4,5,6-tetrahydropyridin-3-yl)-1H-isoindole-1,3(2H)-dione To a solution of 13.474 g (91.1 mmol) of trimethyloxonium tetrafluoroborate in 294 mL of anhydrous dichloromethane was added 22.25 g (91.1 mmol) of (+/−)-3-phtalimidopiperidin-2-one (Heterocycles (1996), 42(2), 537-42, Enantiomer (2001), 6(5), 275-279, Synthesis (1991), (5), 417-20) and the resulting mixture was stirred at room temperature for 12 h. The mixture was hydrolyzed with a saturated aqueous solution of sodium hydrogen carbonate, extracted with dichloromethane, dried over sodium sulfate and the solvent was evaporated to afford 23.22 g (99%) of pure product as a yellow oil. The compound was used as such in the next step.

$^1$H NMR (CDCl$_3$; 200 MHz)

δ (ppm): 7.66-7.92 (m, 4H); 4.69-4.87 (m, 1H); 3.60-3.74 (m, 2H); 3.56 (s, 3H); 1.62-2.40 (m, 4H).

1.2 (+/−)2-(2-Amino-3,4,5,6-tetrahydropyridin-3-yl)-1H-isoindole-1,3(2H)-dione hydrochloride (1:1).

To a solution of 23.224 g (89.92 mMol) of (+/−)2-(2-methoxy-3,4,5,6-tetrahydropyridin-3-yl)-1H-isoindole-1,3

(2H)-dione dissolved in 409 mL of methanol was added at room temperature 4.81 g (89.92 mmol) of ammonium chloride. The resulting mixture was stirred under reflux for 12 h. The cooled solution was evaporated to remove solvent. The residue was triturated with diethyl ether and filtered to afford 23.8 g (95%) of the pure product as a white powder.

Mp: 242-244° C.

$^1$H NMR (DMSO-d$^6$; 200 MHz)

δ (ppm): 8.92 (br s, 2H); 7.85-8.02 (m, 4H); 5.28 (t, 1H); 3.12-3.58 (m, 2H); 1.78-2.15 (m, 4H).

1.3 (+/−)2-(4-Oxo-2-pyridin-4-yl-6,7,8,9-tetrahydro-4H-pyrido[1,2-a]pyrimidin-9-yl)-1H-isoindole-1,3(2H)-dione To a suspension of 9.166 g (32.77 mmol) of (+/−)2-(2-Amino-3,4,5,6-tetrahydropyridin-3-yl)-1H-isoindole-1,3(2H)-dione hydrochloride (1:1) in 50 mL of toluene was added sodium methanolate (freshly prepared from 0.754 g (32.77 mmol) of sodium in 10 mL of methanol and the reaction mixture was stirred at room temperature for 1 h. The mixture was evaporated to dryness, dissolved in 50 mL of toluene and 4.87 g (25.21 mmol) of ethyl 3-(pyridin-4-yl)-3-oxopropionate was added. The resulting solution was stirred under reflux for 12 h. The cooled solution was evaporated to remove solvent. The mixture was dissolved in dichloromethane, washed with a saturated aqueous solution of ammonium chloride, saturated aqueous sodium chloride, dried over sodium sulfate and evaporated to dryness. The residue was chromatographed on silica gel eluting with a mixture of dichloromethane/methanol/aqueous ammonia solution (29%) in the proportions 97/3/0.3 led to afford 3.2 g (34%) of the desired compound as a white powder.

Mp: 211-213° C.

$^1$H NMR (DMSO-d$^6$; 200 MHz)

δ (ppm): 8.50 (d, 2H); 7.78-8.09 (m, 4H); 7.60 (d, 2H); 7.08 (s, 1H); 5.39-5.60 (m, 1H); 4.06-4.28 (m, 1H); 3.65-3.3.88 (m, 1H); 2.08-2.55 (m, 4H).

1.4 (+/−)9-Amino-2-pyridin-4-yl-6,7,8,9-tetrahydro-4H-pyrido[1,2-a]pyrimidin-4-one To a solution of 3.2 g (8.59 mmol) of (+/−)2-(4-oxo-2-pyridin-4-yl-6,7,8,9-tetrahydro-4H-pyrido[1,2-a]pyrimidin-9-yl)-1H-isoindole-1,3(2H)-dione dissolved in 24 mL of ethanol was added 2.09 mL (43 mmol) of hydrazine hydrate and the resulting mixture was stirred under reflux for 2 h. The mixture was filtered and the solid obtained was triturated with dichloromethane for 24 h, filtered, and the resulting filtrates were evaporated to dryness. The resulting residue was purified on silica gel eluting with a mixture of dichloromethane/methanol in the proportions 98/2 to 96/4 to give 1.37 g (66%) of the desired compound as a brown powder.

Mp: 144-146° C.

$^1$H NMR (CDCl$_3$; 200 MHz)

δ (ppm): 8.77 (d, 2H); 7.85 (d, 2H); 6.89 (s, 1H); 3.91-4.26 (m, 3H); 1.61-2.48 (m, 6H).

1.5 (+/−)1-Methyl-N-(4-oxo-2-pyridin-4-yl-6,7,8,9-tetrahydro-4H-pyrido[1,2-a]pyrimidin-9-yl)-1H-1,2,3-benzotriazole-5-carboxamide To a solution of 0.050 g (0.21 mmol) of (+/−)9-amino-2-pyridin-4-yl-6,7,8,9-tetrahydro-4H-pyrido[1,2-a]pyrimidin-4-one dissolved in 2.2 mL of tetrahydrofuran was added 30 μl (0.25 mmol) of triethylamine and 0.0484 g (0.25 mmol) of 1-methyl-1H-1,2,3-benzotriazole-5-carbonyl chloride. The resulting mixture was stirred at room temperature for 16 h. Water was added and the mixture extracted with ethyl acetate. The extracts were washed with a saturated aqueous solution of ammonium chloride, dried and evaporated. The residue was purified by silica gel chromatography, eluting with dichloromethane/methanol/ammonia in the proportions 95/5/0.5 to give 0.041 g of pure product obtained in the form of free base.

Mp: 267-269° C.

$^1$H NMR (DMSO-d$^6$; 200 MHz)

δ (ppm): 9.15 (d, 1H); 8.55 (m, 3H); 8.20-7.80 (m, 4H); 7.10 (s, 1H); 5.20 (m, 1H); 4.45 (s, 3H); 3.90 (m, 2H); 2.20-1.80 (m, 4H).

Example 2

Compound No. 4 of Table 1

(+/−)N-(4-Oxo-2-pyrimidin-4-yl-6,7,8,9-tetrahydro-4H-pyrido[1,2-a]pyrimidin-9-yl)-2,3-dihydro-1-benzofuran-7-carboxamide

2.1 (+/−)2-(4-Oxo-2-pyrimidin-4-yl-6,7,8,9-tetrahydro-4H-pyrido[1,2-a]pyrimidin-9-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate, the compound was obtained as a white powder.

Mp.: 279.9-280.9° C.

$^1$H NMR (DMSO-d$^6$; 200 MHz)

δ (ppm): 9.21 (s, 1H); 8.75 (d, 1H); 8.01-7.81 (m, 4H); 7.52 (d, 1H); 7.19 (s, 1H); 5.58-5.40 (m, 1H); 4.26-4.09 (m, 1H); 3.89-3.68 (m, 1H); 2.48-2.02 (m, 4H.).

2.2 (+/−)9-Amino-2-pyrimidin-4-yl-6,7,8,9-tetrahydro-4H-pyrido[1,2-a]pyrimidin-4-one By analogy with the method described in example 1 (step 1.4), using (+/−)2-(4-oxo-2-pyrimidin-4-yl-6,7,8,9-tetrahydro-4H-pyrido[1,2-a]pyrimidin-9-yl)-1H-isoindole-1,3(2H)-dione in place of (+/−)2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 111-113° C.

$^1$H NMR (DMSO-d$^6$; 200 MHz)

δ (ppm): 9.29 (s, 1H); 8.99 (d, 1H); 8.43 (d, 1H); 7.18 (s, 1H); 4.02-3.75(m, 3H); 2.25 (br s; 2H); 2.23-1.75 (m, 3H); 1.74-1.48 (m, 1H).

2.3 (+/−)N-(4-Oxo-2-pyrimidin-4-yl-6,7,8,9-tetrahydro-4H-pyrido[1,2-a]pyrimidin-9-yl)-2,3-dihydro-1-benzofuran-7-carboxamide By analogy with the method described in example 1 (step 1.5), using (+/−) 9-amino-2-pyrimidin-4-yl-6,7,8,9-tetrahydro-4H-pyrido[1,2-a]pyrimidin-4-one in place of (+/−)9-amino-2-pyridin-4-yl-6,7,8,9-tetrahydro-4H-pyrido[1,2-a]pyrimidin-4-one, the compound was obtained as a white powder.

Mp: 294-296° C.

$^1$H NMR (DMSO-d$^6$; 200 MHz)

δ (ppm): 9.30 (s, 1H); 9.10 (d, 1H); 8.90 (d, 1H); 8.25 (d, 1H); 7.55 (d, 1H); 7.40 (d, 1H); 7.25 (s, 1H); 6.90 (t, 1H); 5.10

(m, 1H); 4.75 (m, 2H); 4.20 (m, 1H); 3.75 (m, 1H); 3.25 (m, 2H); 2.55(m, 1H); 2.10-1.80 (m, 2H); 1.60 (m, 1H).

Example 3

Compound No. 14 of Table 3

(+)2-Methoxy-N-(4-oxo-2-pyrimidin-4-yl-4,6,7,8,9, 10-hexahydro-pyrimido[1,2-a]azepin-10-yl)-nicotinamide 3.1 2-(7-methoxy-3,4,5,6-tetrahydro-2H-azepin-6-yl)-1H-isoindole-1,3(2H)-dione By analogy with the method described in example 1 (step 1.1), using α-amino-ε-caprolactam monohydrochloride (commercially available) in place of 3-phthalimidopiperidin-2-one, the compound was obtained as a yellow oil.

$^1$H NMR ((CDCl3; 200 MHz)

δ (ppm): 7.92-7.66 (m, 4H); 5.10 (d, 1H); 3.90-3.70 (m, 1H); 3.50 (s, 3H); 3.40-3.30 (m, 1H); 2.70-2.50 (m, 1H); 2.10 (m, 1H) 1.90-1.20 (m, 4H).

3.2 2-(2-iminoazepan-3-yl)-1H-isoindole-1,3(2H)-dione hydrochloride (1:1)

By analogy with the method described in example 1 (step 1.2), using 2-(7-methoxy-3,4,5,6-tetrahydro-2H-azepin-6-yl)-1H-isoindole-1,3(2H)-dione in place of 2-(2-methoxy-3,4,5,6-tetrahydropyridin-3-yl)-1H-isoindole-1,3(2H)-dione, the compound was obtained as a white powder.

Mp.: 120-122° C.

$^1$H NMR (CDCl3; 200 MHz)

δ (ppm): 9.40 (br s, 1H); 8.70 (br s, 1H); 8.20-7.60 (m, 4H); 5.28 (br t, 1H); 3.90-3.40 (m, 3H); 2.30-1.30 (m, 5H).

3.3 (+/−)2-(4-oxo-2-pyrimidin-4-yl-4,6,7,8,9,10-hexahydropyrimido[1,2-a]azepin-10-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate and using 2-(2-iminoazepan-3-yl)-1H-isoindole-1,3(2H)-dione hydrochloride (1:1), the compound was obtained as a white powder.

Mp.: 250-252° C.

$^1$H NMR (DMSO-d$^6$; 200 MHz)

δ (ppm): 9.30 (s, 1H); 8.60 (d, 1H); 8.00 (m, 3H); 7.40 (m, 1H); 7.20 (m, 2H); 4.70 (d, 2H); 3.50 (m, 2H); 2.00-1.50 (m, 4H); 1.30 (m, 1H).

3.4 (+/−) 10-amino-2-pyrimidin-4-yl-7,8,9,10-tetrahydropyrimido[1,2-a]azepin-4(6H)-one By analogy with the method described in example 1 (step 1.4), using (+/−)2-(4-oxo-2-pyrimidin-4-yl-4,6,7,8,9,10-hexahydropyrimido[1,2-a]azepin-10-yl)-1H-isoindole-1,3(2H)-dione in place of (+/−)2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 157-159° C.

$^1$H NMR (DMSO-d$^6$; 200 MHz)

δ (ppm): 9.30 (s, 1H); 9.00 (d, 1H); 8.40 (d, 1H); 7.20 (s, 1H); 5.00-4.80 (m, 1H); 4.25 (d, 1H); 3.80-3.60 (dd, 1H); 2.00-1.20 (m, 6H).

3.5 (+)10-amino-2-pyrimidin-4-yl-7,8,9,10-tetrahydropyrimido[1,2-a]azepin-4(6H)-one 20 g (77.73 mmol) of (+/−)10-amino-2-pyrimidin-4-yl-7,8,9,10-tetrahydropyrimido[1,2-a]azepin-4(6H)-one was separated by chiral preparative HPLC (Daicel CHIRAL-PACK AD 20 µm 50×220) eluting with ethanol to give 9.17 g of pure product obtained in the form of free base. $t_R$: 12.0 min.

Mp.: 118° C. $[α]_D^{20}$=+59.97° (c=0.691, DMSO).

$^1$H NMR (DMSO-d$^6$; 200 MHz)

δ (ppm): 9.30 (s, 1H); 9.0 (d, 1H); 8.4 (d, 1H); 7.2 (s, 1H); 5.0-4.8 (m, 1H); 4.25 (d, 1H); 3.8-3.6 (dd, 1H); 2.0-1.2 (m, 6H).

3.6 (−)10-amino-2-pyrimidin-4-yl-7,8,9,10-tetrahydropyrimido[1,2-a]azepin-4(6H)-one 20 g (77.73 mmol) of (+/−)10-amino-2-pyrimidin-4-yl-7,8,9,10-tetrahydropyrimido[1,2-a]azepin-4(6H)-one was separated by chiral preparative HPLC (Daicel CHIRAL-PACK AD 20 µm 50×220) eluting with ethanol to give 9.05 g of pure product obtained in the form of free base. $t_R$: 41.0 min.

Mp.: 117.8° C. $[α]_D^{20}$=−59.76° (c=0.619, DMSO).

$^1$H NMR (DMSO-d$^6$; 200 MHz)

δ (ppm): 9.30 (s, 1H); 9.00 (d, 1H); 8.40 (d, 1H); 7.20 (s, 1H); 5.00-4.80 (m, 1H); 4.25 (d, 1H); 3.80-3.60 (dd, 1H); 2.00-1.20 (m, 6H).

3.7 (+)2-Methoxy-N-(4-oxo-2-pyrimidin-4-yl-4,6,7,8,9,10-hexahydro-pyrimido[1,2-a]azepin-10-yl)-nicotinamide To a solution of 3.50 g (13.60 mmol) of (+)10-amino-2-pyrimidin-4-yl-7,8,9,10-tetrahydropyrimido[1,2-a]azepin-4(6H)-one dissolved in 113 mL of dimethylformamide were added at 0° C. 2.083 g (13.60 mmol) of 2-methoxy nicotinic acid, 2.86 g (13.60 mmol) of diethylcyanophosphonate and 1.9 mL (13.60 mmol) of triethylamine. The resulting mixture was stirred at room temperature for 16 h.

Water and ethyl acetate were added and the mixture stirred for 8 h. The precipitate was filtered and refluxed with isopropanol. The residue was triturated with diisopropylether to give 3.745 g (70%) of pure product obtained in the form of free base.

Mp: 214-216° C. $[α]_D^{20}$=+5.04° (c=0.963, DMSO).

$^1$H NMR (DMSO-d$^6$; 200 MHz)

δ (ppm): 9.40 (d, 1H); 9.30 (s, 1H); 9.10 (d, 1H); 8.40-8.20 (m, 3H); 7.30-7.15 (m, 2H); 5.40 (dd, 1H); 5.00 (dd, 1H); 4.10 (s, 3H); 3.70 (dd, 1H); 2.25-2.10 (m, 1H); 2.09-1.80 (m, 3H); 1.80-1.60 (m, 1H); 1.40-1.20 (m, 1H).

Example 4

Compound No. 15 of Table 3

(−)2-Methoxy-N-(4-oxo-2-pyrimidin-4-yl-4,6,7,8,9, 10-hexahydro-pyrimido[1,2-a]azepin-10-yl)-nicotinamide By analogy with the method described in example 3 (step 3.7), using (−)10-amino-2-pyrimidin-4-yl-7,8,9,10-tetrahydropyrimido[1,2-a]azepin-4(6H)-one (step 3.6) in place of (+)10-amino-2-pyrimidin-4-yl-7,8,9,10-tetrahydropyrimido[1,2-a]azepin-4(6H)-one, the compound, 3.22 g (60%), was obtained as a white powder.

Mp: 212-214° C. $[\alpha]_D^{20}$=−6.41° (c=0.751, DMSO).

$^1$H NMR (DMSO-d$^6$; 200 MHz)

δ (ppm): δ (ppm): 9.40 (d, 1H); 9.30 (s, 1H); 9.10 (d, 1H); 8.40-8.20 (m, 3H); 7.30-7.15 (m, 2H); 5.40 (dd, 1H); 5.00 (dd, 1H); 4.10 (s, 3H); 3.70 (dd, 1H); 2.25-2.10 (m, 1H); 2.09-1.80 (m, 3H); 1.80-1.60 (m, 1H); 1.40-1.20 (m, 1H).

Example 5

Compound No. 2 of Table 2

(+/−)1-Methyl-1H-benzotriazole-5-carboxylic acid (4-oxo-2-pyridin-4-yl-4,6,7,8-tetrahydro-pyrrolo[1,2-a]pyrimidin-8-yl)-amide 5.1 2-(2-Methoxy-4,5-dihydro-3H-pyrrol-3-yl)-isoindole-1,3-dione By analogy with the method described in example 1 (step 1.1), using 2-(2-Oxo-pyrrolidin-3-yl)-isoindole-1,3-dione (prepared by analogy to the method described in (Heterocycles (1996), 42(2), 537-42, Enantiomer (2001), 6(5), 275-279, Synthesis (1991), (5), 417-20)) in place of 3-phtalimidopiperidin -2-one, the compound was obtained as a white powder.

Mp.: 139-141° C.

$^1$H NMR (DMSO-d$^6$; 200 MHz)

δ (ppm): 7.95-7.70 (m, 4H); 5.20 (dd, 1H); 3.90-3.50 (m, 5H); 2.50-2.10 (m, 2H).

5.2 2-(2-Amino-4,5-dihydro-3H-pyrrol-3-yl)-isoindole-1,3-dione hydrochloride (1:1)

By analogy with the method described in example 1 (step 1.2), using 2-(2-methoxy-4,5-dihydro-3H-pyrrol-3-yl)-isoindole-1,3-dione in place of 2-(2-methoxy-3,4,5,6-tetrahydropyridin-3-yl)-1H-isoindole-1,3(2H)-dione, the compound was obtained as a white powder.

Mp.: 121-123° C.

$^1$H NMR (DMSO-d$^6$; 200 MHz)

δ (ppm): 9.25-8.80 (br s, 3H); 7.95-7.70 (m, 4H); 5.65 (dd, 1H); 3.90-3.50 (m, 2H); 2.50-2.20 (m, 2H).

5.3 (+/−)2-(4-Oxo-2-pyridin-4-yl-4,6,7,8-tetrahydro-pyrrolo[1,2-a]pyrimidin-8-yl)-isoindole-1,3-dione By analogy with the method described in example 1 (step 1.3), using ethyl 3-(4-pyridinyl)-3-oxopropionate (prepared by analogy to the method described in patent DE 2705582) and using 2-(2-amino-4,5-dihydro-3H-pyrrol-3-yl)-isoindole-1,3-dione, the compound was obtained as a white powder.

Mp.: 224-226° C.

$^1$H NMR (DMSO-d$^6$; 200 MHz)

δ (ppm): 8.60 (d, 2H); 8.00-7.70 (m, 6H); 7.05 (s, 1H); 5.90 (t, 1H); 4.40-4.20 (m, 1H); 3.80-4.10 (m, 1H); 2.70-2.40 (m, 2H).

5.4 (+/−)8-Amino-2-pyridin-4-yl-7,8-dihydro-6H-pyrrolo[1,2-a]pyrimidin-4-one

By analogy with the method described in example 1 (step 1.4), using 2-(4-oxo-2-pyridin-4-yl-4,6,7,8-tetrahydro-pyrrolo[1,2-a]pyrimidin-8-yl) -isoindole-1,3-dione in place of (+/−)2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 187-189° C.

$^1$H NMR (DMSO-d$^6$; 200 MHz)

δ (ppm): 9.40 (s, 1H); 9.10 (d, 1H); 8.40 (d, 1H); 7.30 (s, 1H); 4.30(dd, 1H); 4.20-3.70 (m, 2H); 2.00-1.70 (m, 2H).

5.5 (+/−)1-Methyl-1H-benzotriazole-5-carboxylic acid (4-oxo-2-pyridin-4-yl-4,6,7,8-tetrahydro-pyrrolo[1,2-a]pyrimidin-8-yl)-amide By analogy with the method described in example 1 (step 1.5), using (+/−) 8-amino-2-pyrimidin-4-yl-7,8-dihydro-6H-pyrrolo[1,2-a]pyrimidin -4-one in place of (+/−)9-amino-2-pyridin-4-yl-6,7,8,9-tetrahydro-4H-pyrido[1,2-a]pyrimidin-4-one, the compound was obtained as a white powder.

Mp.: 393-395° C.

$^1$H NMR (DMSO-d$^6$; 200 MHz)

δ (ppm): 9.35 (d, 1H); 8.70-8.50 (m, 3H); 8.15-8.00 (m, 1H); 7.95-7.85 (m, 3H); 7.05 (s, 1H); 5.50 (dd, 1H); 4.35 (s, 3H); 4.30-4.10 (m, 1H); 4.05-3.85 (m, 1H); 2.75-2.50 (m, 1H); 2.35-2.10 (m, 1H).

Example 6

Compound No. 34 of Table 1

(+/−)2-Methoxy-N-(9-methyl-4-oxo-2-pyrimidin-4-yl-6,7,8,9-tetrahydro-4H-pyrido[1,2-a]pyrimidin-9-yl)-nicotinamide 6.1 (+/−)2-(2-methoxy-3-methyl-3,4,5,6-tetrahydropyridin -3-yl)-1H-isoindole-1,3(2H)-dione By analogy with the method described in example 1 (step 1.1), using 2-(3-methyl-2-oxopiperidin-3-yl)-1H-isoindole-1,3(2H)-dione (prepared by analogy to the method described in Liebigs Annalen der Chemie (1987), (7), 647-8. Archiv der Pharmazie (Weinheim, Germany) (1989), 322(8), 499-505, (Heterocycles (1996), 42(2), 537-42, Enantiomer (2001), 6(5), 275-279, Synthesis (1991), (5), 417-20)) in place of 3-phtalimidopiperidin-2-one, the compound was obtained as a yellow oil.

$^1$H NMR (DMSO-d$^6$; 200 MHz)

δ (ppm): 7.80 (m, 4H); 3.40 (m, 4H); 2.30-2.10 (m, 1H); 1.90-1.70 (m, 5H) 1.65-1.40 (m, 2H).

6.2 (+/−)2-(2-amino-3-methyl-3,4,5,6-tetrahydropyridin-3-yl)-1H-isoindole-1,3(2H)-dione hydrochloride (1:1)

By analogy with the method described in example 1 (step 1.2), using (+/−)2-(2-methoxy-3-methyl-3,4,5,6-tetrahydropyridin-3-yl)-1H-isoindole-1,3(2H)-dione in place of 2-(2-methoxy-3,4,5,6-tetrahydropyridin-3-yl)-1H-isoindole -1,3(2H)-dione, the compound was obtained as a white powder.

Mp.: 165-167° C.

$^1$H NMR (DMSO-d$^6$; 200 MHz)

δ (ppm): 7.70-7.10 (m, 4H); 3.20-3.00 (m, 2H); 2.40-2.20 (m, 1H); 1.80-1.60 (m, 3H), 1.20 (s, 3H).

6.3 (+/−)2-(1-methyl-5-oxo-7-pyrimidin-4-yl-1,2,3,4,4a,5-hexahydronaphthalen-1-yl)-1H-isoindole-1,3(2H)-dione By analogy with the method described in example 1 (step 1.3), using ethyl 3-(4-pyrimidinyl)-3-oxopropionate (prepared by analogy to the method described in patent DE 2705582) in place of ethyl 3-(pyridin-4-yl)-3-oxopropionate and using 2-(2-amino-3-methyl-3,4,5,6-tetrahydropyridin-3-yl)-1H-isoindole-1,3(2H)-dione hydrochloride (1:1) the compound was obtained as a white powder.

Mp.: 184-186° C.

$^1$H NMR (DMSO-d$^6$; 200 MHz)

δ (ppm): 9.25 (s, 1H); 8.80 (d, 1H); 8.00 (d, 2H); 7.80 (m, 4H); 7.20 (s, 1H); 4.30-4.10 (dt, 1H); 3.80-3.60(m, 1H); 2.50 (m, 1H); 2.15 (s, 3H), 2.10-1.80 (m, 2H).

6.4 (+/−)5-amino-5-methyl-3-pyrimidin-4-yl-6,7,8,8a-tetrahydronaphthalen-1(5H)-one By analogy with the method described in example 1 (step 1.4), using (+/−)2-(1-methyl-5-oxo-7-pyrimidin-4-yl-1,2,3,4,4a,5-hexahydronaphthalen-1-yl)-1H-isoindole-1,3(2H)-dione in place of (+/−)2-(4-oxo-2-pyridin-4-yl-6,7,8,9-tetrahydro-4H-pyrido[1,2-a]pyrimidin-9-yl)-1H-isoindole-1,3(2H)-dione, the compound was obtained as a brown powder.

Mp.: 138-140° C.

$^1$H NMR (DMSO-d$^6$; 200 MHz)

δ (ppm): 9.25 (s, 1H); 9.00 (d, 1H); 8.40 (d, 2H); 7.15 (s, 1H); 4.00-3.70 (m, 2H); 2.30 (br s, 2H); 2.10-1.70 (m, 3H); 1.45 (s, 3H).

6.5 (+/−)2-Methoxy-N-(9-methyl-4-oxo-2-pyrimidin-4-yl-6,7,8,9-tetrahydro-4H-pyrido[1,2-a]pyrimidin-9-yl)-nicotinamide By analogy with the method described in example 1 (step 1.5), using (+/−) 5-amino-5-methyl-3-pyrimidin-4-yl-6,7,8,8a-tetrahydronaphthalen-1(5H)-one in place of (+/−)9-amino-2-pyridin-4-yl-6,7,8,9-tetrahydro-4H-pyrido[1,2-a]pyrimidin-4-one, the compound was obtained as a white powder.

Mp: 193-195° C.

$^1$H NMR (DMSO-d$^6$; 200 MHz)

δ (ppm): 9.25 (s, 1H); 8.80 (s, 1H); 8.75 (d, 1H); 8.40-8.25 (m, 2H); 8.10 (dd, 1H); 7.50 (s, 1H); 7.15 (t, 1H); 4.55 (dd, 1H); 4.15 (s, 3H); 3.90-3.70 (m, 1H); 2.80-2.60 (m, 1H); 2.40-2.15 (m, 2H); 2.14-1.90 (m, 1H); 1.85 (s, 3H).

Example 7

Compound No. 58 of Table 1

(+)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide 0.115 g (0.26 mmol) of (+/−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide (compound 46 of table 1) was separated by chiral preparative HPLC (Daicel CHIRALCELL OD-H 20 μm 50×220) eluting with ethanol to give 0.046 g of pure product obtained in the form of free base. $t_R$: 12.7 min.

Mp.: 200-202° C. $[α]_D^{20}$=+94.25° (c=0.257, DMSO).

$^1$H NMR (DMSO-d$^6$; 200 MHz)

δ (ppm): 9.45 (d, 1H); 9.35 (s, 1H); 8.6 (d, 1H); 8.20-7.90 (m, 5H); 7.60-7.10 (m, 4H); 5.30-5.10 (m, 1H); 4.00 (t, 2H); 2.40-2.20 (m, 1H); 2.10-1.80 (m, 3H).

Example 8

Compound No. 59 of Table 1

(−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide 0.115 g (0.26 mmol) of (+/−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide (compound 46 of table 1) was separated by chiral preparative HPLC (Daicel CHIRALCELL OD-H 20 μm 50×220) eluting with ethanol to give 0.042 g of pure product obtained in the form of free base. $t_R$: 10.9 min.

Mp.: 199-200° C. $[α]_D^{20}$=−105.3° (c=0.243, DMSO).

$^1$H NMR (DMSO-d$^6$; 200 MHz)

δ (ppm): 9.45 (d, 1H); 9.35 (s, 1H); 8.6 (d, 1H); 8.20-7.90 (m, 5H); 7.60-7.10 (m, 4H); 5.30-5.10 (m, 1H); 4.00 (t, 2H); 2.40-2.20 (m, 1H); 2.10-1.80 (m, 3H).

Example 9

Compound No. 60 of Table 1

(+)2-Methoxy-N-(9-methyl-4-oxo-2-pyrimidin-4-yl-6,7,8,9-tetrahydro-4H-pyrido[1,2-a]pyrimidin-9-yl)-nicotinamide

9.1. (+)5-amino-5-methyl-3-pyrimidin-4-yl-6,7,8,8a-tetrahydronaphthalen-1(5H)-one 9.05 g (35.17 mmol) of (+/−)5-amino-5-methyl-3-pyrimidin-4-yl-6,7,8,8a-tetrahydronaphthalen-1(5H)-one (compound 6.4 of example 6) was separated by chiral preparative HPLC (Daicel CHIRALCELL OD-I 20 μm 50×220) eluting with a mixture of heptane/dichloromethane/methanol/diisopropylamine in the proportion 65/30/5/3 to give 3.64 g of pure product obtained in the form of free base. $t_R$: 22.0 min.

Mp.: 162-163° C. $[α]_D^{20}$=+63.66° (c=0.386, DMSO).

$^1$H NMR (DMSO-d$^6$; 200 MHz)

δ (ppm): 9.25 (s, 1H); 9.00 (d, 1H); 8.40 (d, 2H); 7.15 (s, 1H); 4.00-3.70 (m, 2H); 2.30 (br s, 2H); 2.10-1.70 (m, 3H); 1.45 (s, 3H).

9.2 (+)2-Methoxy-N-(9-methyl-4-oxo-2-pyrimidin-4-yl-6,7,8,9-tetrahydro-4H-pyrido[1,2-a]pyrimidin-9-yl)-nicotinamide By analogy with the method described in example 3 (step 3.7), using (+)5-amino-5-methyl-3-pyrimidin-4-yl-6,7,8,8a-tetrahydronaphthalen-1(5H)one (step 9.1) and 2-methoxynicotinic acid, the compound, 0.167 g (55%), was obtained as a white powder.

Mp.: 150-152° C. $[α]_D^{20}$=+102.5° (c=0.727, DMSO).

$^1$H NMR (DMSO-d$^6$; 200 MHz)

δ (ppm): 9.25 (s, 1H); 8.80 (s, 1H); 8.75 (d, 1H); 8.40-8.25 (m, 2H); 8.10 (dd, 1H); 7.50 (s, 1H); 7.15 (t, 1H); 4.55 (dd, 1H); 4.15 (s, 3H); 3.90-3.70 (m, 1H); 2.80-2.60 (m, 1H); 2.40-2.15 (m, 2H); 2.14-1.90 (m, 1H); 1.85 (s, 3H).

Example 10

Compound No. 61 of Table 1

(−)2-Methoxy-N-(9-methyl-4-oxo-2-pyrimidin-4-yl-6,7,8,9-tetrahydro-4H-pyrido[1,2-a]pyrimidin-9-yl)-nicotinamide

10.1 (−)5-amino-5-methyl-3-pyrimidin-4-yl-6,7,8,8a-tetrahydronaphthalen-1(5H)-one 9.05 g (35.17 mmol) of (+/−)5-amino-5-methyl-3-pyrimidin -4-yl-6,7,8,8a-tetrahydronaphthalen-1(5H)-one (compound 6.4 of example 6) was separated by chiral preparative HPLC (Daicel CHIRALCELL OD-I 20 μm 50×220) eluting with a mixture of heptane/dichloromethane/methanol/diisopropylamine in the proportion 65/30/5/3 to give 4.18 g of pure product obtained in the form of free base. $t_R$: 8.0 min.

Mp.: 150-151° C. $[\alpha]_D^{20}$=−57.71° (c=0.322, DMSO).

$^1$H NMR (DMSO-d$^6$; 200 MHz)

δ (ppm): 9.25 (s, 1H); 9.00 (d, 1H); 8.40 (d, 2H); 7.15 (s, 1H); 4.00-3.70 (m, 2H); 2.30 (br s, 2H); 2.10-1.70 (m, 3H); 1.45 (s, 3H).

10.2 (−)2-Methoxy-N-(9-methyl-4-oxo-2-pyrimidin-4-yl -6,7,8,9-tetrahydro-4H-pyrido[1,2-a]pyrimidin-9-yl)-nicotinamide By analogy with the method described in example 3 (step 3.7), using (−)5-amino-5-methyl-3-pyrimidin-4-yl-6,7,8,8a-tetrahydronaphthalen-1(5H) -one (step 10.1) and 2-methoxynicotinic acid, the compound, 0.130 g (43%), was obtained as a white powder.

Mp.: 139-141° C. $[\alpha]_D^{20}$=−102.7° (c=0.823, DMSO).

$^1$H NMR (DMSO-d$^6$; 200 MHz)

δ (ppm): 9.25 (s, 1H); 8.80 (s, 1H); 8.75 (d, 1H); 8.40-8.25 (m, 2H); 8.10 (dd, 1H); 7.50 (s, 1H); 7.15 (t, 1H); 4.55 (dd, 1H); 4.15 (s, 3H); 3.90-3.70 (m, 1H); 2.80-2.60 (m, 1H); 2.40-2.15 (m, 2H); 2.14-1.90 (m, 1H); 1.85 (s, 3H).

Example 11

Compound No. 62 of Table 1

(+)[1,5]Naphthyridine-2-carboxylic acid (4-oxo-2-pyrimidin-4-yl-6,7,8,9-tetrahydro-4H-pyrido[1,2-a]pyrimidin-9-yl)-amide 0.098 g (0.25 mmol) of (+/−) [1,5]naphthyridine-2-carboxylic acid (4-oxo-2-pyrimidin-4-yl-6,7,8,9-tetrahydro-4H-pyrido[1,2-a]pyrimidin-9-yl)-amide (compound 44 of table 1) was separated by chiral preparative HPLC (Daicel CHIRALCELL OD-H 20 μm 50×220) eluting with ethanol to give 0.025 g of pure product obtained in the form of free base. $t_R$: 14.35 min.

Mp.: 282-284° C. $[\alpha]_D^{20}$=+33.13° (c=0.154, DMSO).

$^1$H NMR (DMSO-d$^6$; 200 MHz)

δ (ppm): 9.60 (d, 1H); 9.30 (s, 1H); 9.10 (s, 1H); 8.90 (d, 1H); 8.60 (d, 1H); 8.50-8.40 (m, 2H); 8.10 (d, 1H); 7.90 (m, 1H); 7.25 (s, 1H); 5.25 (m, 1H); 4.00 (t, 2H); 2.40 (m, 1H); 2.10 (m, 3H).

Example 12

Compound No. 63 of Table 1

(−)[1,5]Naphthyridine-2-carboxylic acid (4-oxo-2-pyrimidin-4-yl-6,7,8,9-tetrahydro-4H-pyrido[1,2-a]pyrimidin-9-yl)-amide 0.098 g (0.25 mmol) of (+/−)[1,5]naphthyridine-2-carboxylic acid (4-oxo-2-pyrimidin-4-yl-6,7,8,9-tetrahydro-4H-pyrido[1,2-a]pyrimidin-9-yl)-amide (compound 44 of table 1) was separated by chiral preparative HPLC (Daicel CHIRALCELL OD-H 20 μm 50×220) eluting with ethanol to give 0.023 g of pure product obtained in the form of free base. $t_R$: 12.52 min.

Mp.: 272-274° C. $[\alpha]_D^{20}$=−26.84° (c=0.211, DMSO).

$^1$H NMR (DMSO-d$^6$; 200 MHz)

δ (ppm): 9.60 (d, 1H); 9.30 (s, 1H); 9.10 (s, 1H); 8.90 (d, 1H); 8.60 (d, 1H); 8.50-8.40 (m, 2H); 8.10 (d, 1H); 7.90 (m, 1H); 7.25 (s, 1H); 5.25 (m, 1H); 4.00 (t, 2H); 2.40 (m, 1H); 2.10 (m, 3H).

Example 13

Compound No. 104 of Table 3

(+)2-Methoxy-N-(1 0-methyl-4-oxo-2-pyrimidin-4-yl-4,6,7,8,9,10-hexahydro-pyrimido[1,2-a]azepin-10-yl)-nicotinamide

13.1 2-Pyrimidin-4-yl-7,8,9,10-tetrahydro-6H-pyrimido[1,2-a]azepin-4-one

To a suspension of 77.9 g (524.1 mmol) of 2H-azepin-7-amine, 3,4,5,6-tetrahydro, monohydrochloride (synthesis as described in WO96/14844 or Journal of Medicinal Chemistry (1998), 41(9), 1361-1366 or by analogy with the method described in example 1, step 1.1. and 1.2 using ε-caprolactam instead of (+/−)-3-phthalimidopiperidin-2-one) in 390 mL of ethanol was added 72.4 g (524.1 mmol) of potassium carbonate. The reaction mixture was stirred at room temperature for 10 min, 101.7 g (524.1 mmol) of ethyl 3-(4-pyrimidinyl)-3-oxopropionate was added and the resulting mixture was stirred under reflux for 16 h. The cooled solution was evaporated to remove solvent. The mixture was dissolved in dichloromethane, washed with a saturated aqueous solution of sodium chloride, dried over sodium sulfate and evaporated to dryness. The residue was filtrate through a pad of silica, rinsing with dichloromethane and then ethyl acetate. After evaporation, the resulting solid was triturated with diethyl ether to afford 36.4 g (28%) of pure product as a white-brown powder.

Mp: 148-150° C.

$^1$H NMR (DMSO-d$^6$; 400 MHz)

δ (ppm): 9.32 (s, 1H), 9.01 (d, 1H), 8.24 (d, 1H), 7.21 (s, 1H), 4.32 (m, 2H), 3.11 (m, 2H), 1.66-1.83 (m, 6H).

13.2 (+/−)10-Methyl-2-pyrimidin-4-yl-7,8,9,10-tetrahydro -6H-pyrimido[1,2-a]azepin-4-one To a solution of 26.1 g (107.73 mmol) of 2-pyrimidin-4-yl-7,8,9,10-tetrahydro-6H-pyrimido[1,2-a]azepin-4-one in dry tetrahydrofuran (450 mL) under argon at −78° C. was added 82.5 mL (82.5 mmol) of lithium bis(trimethylsilyl) amide (1M in tetrahydrofuran). The solution was stirred at −78° C. for 10 min and 25.7 mL of methyl iodide (412.7 mmol) was added. The reaction was stirred at −78° C. for 1 h and then at 0° C. for 2 h. The mixture was quenched with the addition of a saturated solution of ammonium chloride and extracted with ethyl acetate. The organic phase was dried over sodium sulfate and concentrated. The residue was chromatographed on silica gel eluting with a mixture of dichloromethane/methanol in the proportions 99/1 to afford 11.0 g (40%) of the desired compound as a white solid.

Mp: 184-186° C.

$^1$H NMR (DMSO-d$^6$; 400 MHz)

δ (ppm): 9.31 (s, 1H), 9.03 (d, 1H), 8.30 (d, 1H), 7.22 (s, 1H), 5.02 (m, 1H), 3.70 (m, 1H), 3.40 (m, 1H), 2.00 (m, 1H), 1.78-1.90 (m, 3H), 1.30-1.48 (m, 5H).

13.3 (+/−)10-Amino-10-methyl-2-pyrimidin-4-yl-7,8,9,10-tetrahydro-6H-pyrimido[1,2-a]azepin-4-one To a solution of 10.0 g (39.0 mmol) (+/−)10-methyl-2-pyrimidin -4-yl-7,8,9,10-tetrahydro-6H-pyrimido[1,2-a]azepin-4-one in a mixture of dry tetrahydrofuran/dimethyltetrahydropyrimidinone (150/20 mL) under argon at −78° C. was added 81.9 mL (81.9 mmol) of lithium bis(trimethylsilyl) amide (1M in tetrahydrofuran). The solution was stirred at −78° C. for 5 min. The solution was warmed to 0° C. by changing the cold bath and 13.3 g (42.9 mmol) of 2,4,6-triisopropylbenzene -sulfonyl azide in 30 mL of dry tetrahydrofuran was added. The reaction was stirred at 0° C. for 1 h, at room temperature for 1 h and 10.0 mL (175.6 mmol) of acetic acid was added. The mixture was stirred at room temperature for 1 h and then diluted with ethyl acetate. The organic phase was washed with water and a saturated solution of sodium chloride, dried over sodium sulfate and concentrated to afford 10-azido-10-methyl-2-pyrimidin-4-yl-7,8,9,10-tetrahydro-6H-pyrimido[1,2-a]azepin-4-one as an orange oil. The compound was used as such in the next step.

A mixture of 23.9 mL (234.1 mmol) of thiophenol, 11.1 g (58.5 mmol) of tin (II) chloride and 24.5 mL (175.6 mmol) triethylamine in acetonitrile (300 mL) was stirred for 5 min at room temperature. 10-Azido-10-methyl-2-pyrimidin-4-yl-7,8,9,10-tetrahydro-6H-pyrimido[1,2-a]azepin-4-one residue diluted in 90 mL of acetonitrile was added to this solution and the mixture was stirred for 1 h. A solution of sodium hydroxide (1M) was added and the mixture extracted with dichloromethane. After an acid-basic work-up, the residue was chromatographed on silica gel eluting with a mixture of dichloromethane/methanol in the proportions 95/5 to afford 6.3 g (58%) of a yellow solid.

Mp: 139-141° C.

$^1$H NMR (DMSO-d$^6$; 400 MHz)

δ (ppm): 9.40 (s, 1H), 9.18 (d, 1H), 8.85 (br s, 2H), 8.68 (d, 1H), 7.38 (s, 1H), 5.18 (m, 1H), 3.62 (m, 1H), 3.20 (m, 1H), 2.23-1.75 (m, 4H), 1.83 (s, 3H), 1.50 (m, 1H).

13.4 (+)10-Amino-10-methyl-2-pyrimidin-4-yl-7,8,9,10-tetrahydro-6H-pyrimido[1,2-a]azepin-4-one 0.797 g (2.94 mmol) of (+/−)10-amino-10-methyl-2-pyrimidin-4-yl-7,8,9,10-tetrahydro-6H-pyrimido[1,2-a]azepin-4-one was separated by chiral preparative HPLC (Daicel Chiralcel AD 20 μm) eluting with ethanol to give 0.390 g of pure product obtained in the form of free base. $t_R$: 19 min.

Mp.: 117-119° C. $[α]_D^{20}$=+42.50° (c=0.188, DMSO).

$^1$H NMR (DMSO-d$^6$; 400 MHz)

δ (ppm): 9.32 (s, 1H), 9.08 (d, 1H), 8.31 (d, 1H), 7.25 (s, 1H), 4.80 (m, 2H), 2.30 (br s, 2H), 2.03 (m, 1H), 1.89 (m, 2H), 1.79 (m, 2H), 1.68 (s, 3H), 1.38 (m, 1H).

13.5 (+)2-Methoxy-N-(10-methyl-4-oxo-2-pyrimidin-4-yl -4,6,7,8,9,10-hexahydro-pyrimido[1,2-a]azepin-10-yl)-nicotinamide To a solution of 0.100 g (0.37 mmol) of (+)10-amino-10-methyl-2-pyrimidin-4-yl-7,8,9,10-tetrahydro-6H-pyrimido[1,2-a]azepin-4-one dissolved in 3 mL of dimethylformamide were added at 0° C., 0.056 g (0.37 mmol) of 2-methoxy nicotinic acid, 0.070 mL (0.44 mmol) of diethylcyanophosphonate and 0.05 mL (0.37 mmol) of triethylamine. The resulting mixture was stirred at room temperature for 20 h. Water and ethyl acetate were added, the mixture was extracted with ethyl acetate and the organic phase was washed with water and a saturated solution of ammonium chloride, dried over sodium sulfate and concentrated. After purification on silica gel, the residue was triturated with petroleum ether to give 0.056 g (37%) of pure product obtained in the form of free base as a yellow solid.

Mp: 109-111° C. $[α]_D^{20}$=+137.0° (c=0.428, DMSO).

$^1$H NMR (DMSO-d$^6$; 400 MHz)

δ (ppm): 9.36 (d, 1H), 9.09 (d, 1H), 8.80 (s, 1H), 8.35 (m, 2H), 7.96 (m, 1H), 7.28 (s, 1H), 7.11 (m, 1H), 5.10 (m, 1H), 4.02 (s, 3H), 3.98 (m, 1H), 2.32 (m, 1H), 2.18 (m, 1H), 2.01 (m, 1H), 1.85 (s, 5H), 1.35 (m, 1H).

Example 14

Compound No. 106 of Table 3

14.1 (−)10-Amino-10-methyl-2-pyrimidin-4-yl-7,8,9,10-tetrahydro-6H-pyrimido[1,2-a]azepin-4-one 0.797 g (2.94 mmol) of (+/−)10-amino-10-methyl-2-pyrimidin-4-yl-7,8,9,10-tetrahydro-6H-pyrimido[1,2-a]azepin-4-one (step 13.3) was separated by chiral preparative HPLC (Daicel Chiralcel AD 20 μm) eluting with ethanol to give 0.384 g of pure product obtained in the form of free base. $t_R$: 38 min.

Mp.: 117-119° C. $[α]_D^{20}$=−45.11° (c=0.235, DMSO).

$^1$H NMR (DMSO-d$^6$; 400 MHz)

δ (ppm): 9.32 (s, 1H), 9.08 (d, 1H), 8.31 (d, 1H), 7.25 (s, 1H), 4.80 (m, 2H), 2.30 (br s, 2H), 2.03 (m, 1H), 1.89 (m, 2H), 1.79 (m, 2H), 1.68 (s, 3H), 1.38 (m, 1H).

14.2 (−)2-Methoxy-N-(10-methyl-4-oxo-2-pyrimidin-4-yl -4,6,7,8,9,10-hexahydro-pyrimido[1,2-a]azepin-10-yl)-nicotinamide By analogy with the method described in example 13 (step 13.5), using (−) 10-amino-10-methyl-2-pyrimidin-4-yl-7,8,9,10-tetrahydro-6H -pyrimido[1,2-a]azepin-4-one in place of (+)10-amino-10-methyl-2-pyrimidin-4-yl-7,8,9,10-tetrahydro-6H-pyrimido[1,2-a]azepin-4-one, the compound, 0.048 g (32%), was obtained as a white powder.

Mp: 111° C. (decomposition). $[α]_D^{20}$=−139.7° (c=0.373, DMSO).

$^1$H NMR (DMSO-d$^6$; 400 MHz)

δ (ppm): 9.36 (d, 1H), 9.09 (d, 1H), 8.80 (s, 1H), 8.35 (m, 2H), 7.96 (m, 1H), 7.28 (s, 1H), 7.11 (m, 1H), 5.10 (m, 1H), 4.02 (s, 3H), 3.98 (m, 1H), 2.32 (m, 1H), 2.18 (m, 1H), 2.01 (m, 1H), 1.85 (s, 5H), 1.35 (m, 1H).

Example 15

Compound No. 79 of Table 3

(+/−)2,3-Dihydro-benzofuran-7-carboxylic acid (10-methyl-4-oxo -2-pyridin-4-yl-4,6,7,8,9,10-hexahydro-pyrimido[1,2-a]azepin-10-yl)-amide 15.1 2-Pyridin-4-yl-7,8,9,10-tetrahydro-6H-pyrimido [1,2-a]azepin-4-one By analogy with the method described in example 13 (step 13.1), using ethyl 3-(pyridin-4-yl)-3-oxopropionate in place of ethyl 3-(4-pyrimidinyl)-3-oxopropionate, 20.0 g of the compound (54%) was obtained as a white powder.
Mp: 148-150° C.
$^1$H NMR (DMSO-d$^6$; 400 MHz)
δ (ppm): 8.79 (d, 2H), 8.01 (d, 2H), 7.08 (s, 1H), 4.31 (m, 2H), 3.11 (m, 2H), 1.80 (m, 4H), 1.78 (m, 2H).

15.2 (+/−)10-Methyl-2-pyridin-4-yl-7,8,9,10-tetrahydro-6H-pyrimido[1,2-a]azepin-4-one By analogy with the method described in example 13 (step 13.2), using 2-pyridin-4-yl-7,8,9,10-tetrahydro-6H-pyrimido[1,2-a]azepin-4-one in place of 2-pyrimidin-4-yl-7,8, 9,10-tetrahydro-6H-pyrimido[1,2-a]azepin-4-one, 1.13 g of the compound (21%) was obtained as a orange powder.
Mp: 137-139° C.
$^1$H NMR (DMSO-d$^6$; 400 MHz)
δ (ppm): 8.72 (d, 2H), 8.08 (d, 2H), 7.09 (s, 1H), 5.01 (m, 1H), 3.68 (m, 1H), 3.37 (m, 2H), 1.98 (m, 1H), 1.83 (m, 2H), 1.49-1.25 (m, 5H).

15.3 (+/−)2,3-Dihydro-benzofuran-7-carboxylic acid (10-methyl -4-oxo-2-pyridin-4-yl-4,6,7,8,9,10-hexahydro-pyrimido[1,2-a]azepin-10-yl)-amide By analogy with the method described in example 13 (step 13.3), using (+/−)10-methyl-2-pyridin-4-yl-7,8,9,10-tetrahydro-6H-pyrimido[1,2-a]azepin-4-one in place of (+/−)10-methyl-2-pyrimidin-4-yl-7,8,9,10-tetrahydro-6H-pyrimido [1,2-a]azepin-4-one, 10-azido-1 0-methyl-2-pyridin-4-yl-7, 8,9,10-tetrahydro-pyrimido[1,2-a]azepin-4-one was obtained.
The compound was used as such in the next step.
10-azido-10-methyl-2-pyridin-4-yl-7,8,9,10-tetrahydro-6H -pyrimido[1,2-a]azepin-4-one was reduced by using H-Cube™ technology (from THALES Nanotechnology, full H$_2$, Pd/C as catalyst, 1 mL/min and 50° C.). After an acid-basic work-up, (+/−)10-amino-1 0-methyl-2-pyridin-4-yl-7, 8,9,10-tetrahydro-6H-pyrimido[1,2-a]azepin-4-one was obtained and the compound was used as such in the next step.
By analogy with the method described in example 13 (step 13.5) by using 2,3-dihydrobenzofuran-7-carboxylic acid and (+/−)10-amino-10-methyl-2-pyridin-4-yl-7,8,9,10-tetrahydro-6H-pyrimido[1,2-a]azepin-4-one instead of 2-methoxy nicotinic acid and (+)10-amino-1 0-methyl-2-pyrimidin-4-yl-7,8,9,10-tetrahydro-6H-pyrimido[1,2-a]azepin-4-one, 76 mg (39%) of a white compound was obtained.
Mp: 213-214° C.
$^1$H NMR (DMSO-d$^6$; 400 MHz)
δ (ppm): 8.75 (d, 2H), 8.38 (br s, 1H), 8.08 (d, 2H), 7.52 (d, 1H), 7.45 (d, 1H), 7.15 (s, 1H), 6.95 (t, 1H), 5.02 (m, 1H), 4.80 (m, 2H), 3.80 (m, 1H), 3.30 (m, 4H), 2.32 (m, 1H), 2.13-1.80 (m, 2H), 1.88 (s, 3H), 1.35 (m, 1H).

Example 16

Compound No. 93 of Table 3

(+/−)4-Methoxy-pyridine-2-carboxylic acid (10-ethyl-4-oxo-2-pyrimidin-4-yl-4,6,7,8,9,10-hexahydro-pyrimido[1,2-a]azepin-10-yl)-amide 16.1 (+/−)10-Ethyl-2-pyrimidin-4-yl-7,8,9,10-tetrahydro -6H-pyrimido[1,2-a]azepin-4-one By analogy with the method described in example 13 (step 13.2), using ethyl iodide instead of methyl iodide, 0.46 g of the compound (21%) was obtained as a white powder.
Mp: 128-130° C.
$^1$H NMR (DMSO-d$^6$; 400 MHz)
δ (ppm): 9.32 (s, 1H), 9.08 (d, 1H), 8.27 (d, 1H), 7.22 (s, 1H), 4.98 (m, 1H), 3.78 (m, 1H), 3.12 (m, 1H), 2.15 (m, 1H), 1.95 (m, 2H), 1.80 (m, 2H), 1.60 (m, 1H), 1.35 (m, 2H), 1.08 (t, 3H).

16.2 (+/−)10-Amino-10-ethyl-2-pyrimidin-4-yl-7,8, 9,10-tetrahydro-6H-pyrimido[1,2-a]azepin-4-one By analogy with the method described in example 13 (step 13.3), using 10-ethyl-2-pyrimidin-4-yl-7,8,9,10-tetrahydro-6H-pyrimido[1,2-a]azepin-4-one in place of 1 0-methyl-2-pyrimidin-4-yl-7,8,9,10-tetrahydro-6H-pyrimido[1,2-a] azepin-4-one, 0.83 g of the compound (46%) was obtained as a orange oil.
$^1$H NMR (DMSO-d$^6$; 400 MHz)
δ (ppm): 9.32 (s, 1H), 9.08 (d, 1H), 8.32 (d, 1H), 7.28 (s, 1H), 4.91 (m, 1H), 4.40 (m, 1H), 2.01 (m, 2H), 1.85-1.50 (m, 6H), 0.98 (t, 3H)

16.3 (+/−)4-Methoxy-pyridine-2-carboxylic acid (10-ethyl-4-oxo-2-pyrimidin-4-yl-4,6,7,8,9,10-hexahydro-pyrimido[1,2-a]azepin-10-yl)-amide By analogy with the method described in example 13 (step 13.5), using (+/−) 10-amino-1 0-ethyl-2-pyrimidin-4-yl-7,8, 9,10-tetrahydro-6H-pyrimido[1,2-a]azepin-4-one and 4-methoxy-pyridine-2-carboxylic acid in place of (+)10-amino-10-methyl-2-pyrimidin-4-yl-7,8,9,10-tetrahydro-6H-pyrimido[1,2-a]azepin-4-one and 2-methoxy nicotinic acid, 37 mg (31%) of the compound was obtained as a white solid.
Mp: 200-202° C.
$^1$H NMR (DMSO-d$^6$; 400 MHz)
δ (ppm): 10.20 (br s, 1H), 9.38 (s, 1H), 9.25 (d, 1H), 8.68 (d, 1H), 8.61 (m, 1H), 7.58 (s, 1H), 7.34 (s, 1H), 7.22 (m, 1H), 4.50 (m, 1H), 4.32 (m, 1H), 3.92 (s, 3H), 2.58 (m, 2H), 2.32 (m, 2H), 1.90 (m, 2H), 1.71 (m, 2H), 0.81 (t, 3H).

Example 17

Compound No. 100 of Table 3

(+/−)N-(3-Bromo-4-oxo-2-pyrimidin-4-yl-4,6,7,8,9, 10-hexahydro-pyrimido[1,2-a]azepin-10-yl)-2-methoxy-nicotinamide 17.1 (+/−)(3-Bromo-4-oxo-2-pyrimidin-4-yl-4,6,7,8, 9,10-hexahydro-pyrimido[1,2-a]azepin-10-yl)-carbamic acid ethyl ester 0.3 g (1.17 mmol) of (+/−)10-amino-2-pyrimidin-4-yl-7,8, 9,10-tetrahydropyrimido[1,2-a]azepin-4(6H)-one (compound 3.4 of example 3) was diluted in 8 mL of tetrahydrofuran. 0.18 mL (1.28 mmol) of triethylamine was added at 0° C. and the mixture was stirred for 10 min and 0.12 mL (1.28 mmol) of ethyl chloroformate was added. The resulting mixture was stirred at room temperature for 1 h and quenched by adding a saturated solution of ammonium chloride. The product was extracted with dichloromethane, dried over sodium sulfate and the solvent was evaporated. The residue was triturated with diethyl ether and filtered to afford 0.28 g (72%) of (4-oxo-2-pyrimidin-4-yl-4,6,7,8,9,10-hexahydro-pyrimido[1,2-a]azepin-10-yl)-carbamic acid ethyl ester as a yellow solid (Mp.: 168-170° C.). The compound was used as such in the next step.

To a solution of 0.080 g (0.24 mmol) of (4-oxo-2-pyrimidin-4-yl -4,6,7,8,9,10-hexahydro-pyrimido[1,2-a]azepin-10-yl)-carbamic acid ethyl ester in dimethylformamide (4 mL) were added 0.21 g (1.21 mmol) of N-bromosuccinimide and 0.03 g (0.12 mmol) of benzoyl peroxide. The solution was stirred at room temperature for 10 min and at 50° C. for 20 min. The reaction was quenched by adding a saturated solution of ammonium chloride. The product was extracted with dichloromethane, the organic phase was washed with a saturated solution of sodium chloride, dried over sodium sulfate, filtered and the solvent was evaporated. The residue was chromatographed on silica gel eluting with a mixture of dichloromethane/methanol in the proportions 95/5 to afford 58 mg of a solid.

Mp: 72-74° C.

$^1$H NMR (DMSO-d$^6$; 400 MHz)

δ (ppm): 9.42 (s, 1H), 9.12 (d, 1H), 7.92 (d, 1H), 7.51 (m, 1H), 5.01 (m, 2H), 4.08 (m, 2H), 3.92 (m, 1H), 2.08-1.71 (m, 5H), 1.52 (m, 1H), 1.20 (m, 3H)

17.2 (+/−)N-(3-Bromo-4-oxo-2-pyrimidin-4-yl-4,6,7,8,9,10-hexahydro-pyrimido[1,2-a]azepin-10-yl)-2-methoxy-nicotinamide To a solution of 0.34 g (0.84 mmol) of (+/−)(3-bromo-4-oxo-2-pyrimidin-4-yl-4,6,7,8,9,10-hexahydro-pyrimido[1,2-a]azepin-10-yl)-carbamic acid ethyl ester in 2 mL of acetic acid was added 0.78 mL (4.21 mmol) of a solution of hydrobromic acid (5.7N in acetic acid). The reaction was stirred at 100° C. for 3 h. The solvent was evaporated and an acid-basic work-up gave 65 mg (33%) of 10-amino-3-bromo-2-pyrimidin-4-yl-7,8,9,10-tetrahydro-6H-pyrimido[1,2-a]azepin-4-one as an orange oil. The compound was used as such in the next step.

By analogy with the method described in example 13 (step 13.5), using (+/−)10-amino-3-bromo-2-pyrimidin-4-yl-7,8,9,10-tetrahydro-6H-pyrimido[1,2-a]azepin-4-one in place of (+)10-amino-10-methyl-2-pyrimidin-4-yl-7,8,9,10-tetrahydro-6H-pyrimido[1,2-a]azepin-4-one; 40 mg (49%) of the titled compound was obtained as a white solid.

Mp: 190-192° C.

$^1$H NMR (DMSO-d$^6$; 400 MHz)

δ (ppm): 9.58 (m, 1H), 9.48 (s, 1H), 9.12 (d, 1H), 8.38 (m, 2H), 7.95 (d, 1H), 7.21 (m, 1H), 5.41 (m, 1H), 5.08 (m, 1H), 3.90 (m, 1H), 3.62 (s, 3H), 2.20 (m, 2H), 2.08-1.95 (m, 3H), 1.75 (m, 1H), 1.48 (m, 1H).

Example 18

Compound No. 105 of Table 3

(−)2,6-Dimethoxy-N-(10-methyl-4-oxo-2-pyrimidin-4-yl-4,6,7,8,9,10-hexahydro-pyrimido[1,2-a]azepin-10-yl)-nicotinamide By analogy with the method described in example 14 (step 14.2), using 2,4-dimethoxy nicotinic acid in place of 2-methoxy nicotinic acid, the compound, 0.082 g (51%), was obtained as a white powder.

Mp: 114° C. decomposition. $[\alpha]_D^{20}$=−197.2° (c=0.460, DMSO).

$^1$H NMR (DMSO-d$^6$; 400 MHz)

δ (ppm): 9.32 (s, 1H), 9.08 (d, 1H), 8.48 (s, 1H), 8.30 (m, 1H), 8.00 (d, 1H), 7.25 (s, 1H), 6.50 (d, 1H), 5.08 (m, 1H), 4.10 (s, 3H), 3.98 (s, 3H), 3.85 (m, 1H), 2.32 (m, 1H), 2.20-1.88 (m, 2H), 1.88 (m, 5H), 1.32 (m, 1H).

Example 19

Compound No. 107 of Table 3

(+)2,6-Dimethoxy-N-(10-methyl-4-oxo-2-pyrimidin-4-yl-4,6,7,8,9,10-hexahydro-pyrimido[1,2-a]azepin-10-yl)-nicotinamide By analogy with the method described in example 13 (step 13.5), using 2,4-dimethoxy nicotinic acid in place of 2-methoxy nicotinic acid, the compound, 0.066 g (41%), was obtained as a white powder.

Mp: 89-91° C. $[\alpha]_D^{20}$=+196.6° (c=0.405, DMSO).

$^1$H NMR (DMSO-d$^6$; 400 MHz)

δ (ppm): 9.32 (s, 1H), 9.08 (d, 1H), 8.48 (s, 1H), 8.30 (m, 1H), 8.00 (d, 1H), 7.25 (s, 1H), 6.50 (d, 1H), 5.08 (m, 1H), 4.10 (s, 3H), 3.98 (s, 3H), 3.85 (m, 1H), 2.32 (m, 1H), 2.20-1.88 (m, 2H), 1.88 (m, 5H), 1.32 (m, 1H).

Example 20

Compound No. 102 of Table 3

(+)2,6-Dimethoxy-pyrimidine-4-carboxylic acid (4-oxo-2-pyrimidin -4-yl-4,6,7,8,9,10-hexahydro-pyrimido[1,2-a]azepin-10-yl)-amide By analogy with the method described in example 13 (step 13.5), using (+) 10-amino-2-pyrimidin-4-yl-7,8,9,10-tetrahydropyrimido[1,2-a]azepin-4(6H)-one (step 3.5 of example 3) and 2,4-dimethoxy nicotinic acid in place of (+)10-amino-10-methyl-2-pyrimidin-4-yl-7,8,9,10-tetrahydro-6H-pyrimido[1,2-a]azepin-4-one and 2-methoxy nicotinic acid. The compound, 0.903 g (69%), was obtained as a powder.

Mp: 199-200° C. $[\alpha]_D^{20}$=+25.34° (c=0.266, DMSO).

$^1$H NMR (DMSO-d$^6$; 400 MHz)

δ (ppm): 9.48 (s, 1H), 9.35 (m, 1H), 9.22 (d, 1H), 8.38 (m, 2H), 7.35 (s, 1H), 6.62 (d, 1H), 5.51 (m, 1H), 5.10 (m, 1H), 4.20 (s, 3H), 4.02 (s, 3H), 3.78 (m, 1H), 2.25 (m, 1H), 2.12-1.95 (m, 3H), 1.75 (m, 1H), 1.41 (m, 1H).

Example 21

Compound No. 103 of Table 3

(−)2,6-Dimethoxy-pyrimidine-4-carboxylic acid (4-oxo-2-pyrimidin-4-yl-4,6,7,8,9,10-hexahydro-pyrimido[1,2-a]azepin-10-yl)-amide By analogy with the method described in example 13 (step 13.5), using (−)10-amino-2-pyrimidin-4-yl-7,8,9,10-tetrahydropyrimido[1,2-a]azepin-4(6H)-one (step 3.6 of example 3) and 2,4-dimethoxy nicotinic acid in place of (+)10-amino-10-methyl-2-pyrimidin-4-yl-7,8,9,10-tetrahydro-6H-pyrimido[1,2-a]azepin-4-one and 2-methoxy nicotinic acid, the compound, 0.85 g (64%), was obtained as a powder.

Mp: 200-202° C. $[\alpha]_D^{20}$=−29.93° (c=0.426, DMSO).
$^1$H NMR (DMSO-d$^6$; 400 MHz)
δ (ppm): 9.48 (s, 1H), 9.35 (m, 1H), 9.22 (d, 1H), 8.38 (m, 2H), 7.35 (s, 1H), 6.62 (d, 1H), 5.51 (m, 1H), 5.10 (m, 1H), 4.20 (s, 3H), 4.02 (s, 3H), 3.78 (m, 1H), 2.25 (m, 1H), 2.12-1.95 (m, 3H), 1.75 (m, 1H), 1.41 (m, 1H).

Example 22

Compound No. 108 of Table 3

(−)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide By analogy with the method described in example 14 (step 14.2), using 5-bromo-2,3-dihydro-benzofuran-7-carboxylic acid in place of 2-methoxy nicotinic acid, the compound, 0.075 g (35%), was obtained as a white powder.

Mp: 126° C. (decomposition). $[\alpha]_D^{20}$=−144.2° (c=0.449, DMSO).
$^1$H NMR (DMSO-d$^6$; 400 MHz)
δ (ppm): 9.35 (d, 1H), 9.10 (d, 1H), 8.45 (m, 1H), 8.32 (d, 1H), 7.65 (s, 1H), 7.55 (s, 1H), 7.30 (s, 1H), 5.02 (m, 1H), 4.85 (m, 2H), 3.81 (m, 1H), 3.81 (m, 1H), 2.31 (m, 1H), 2.15-1.82 (m, 5H), 1.90 (s, 3H), 1.35 (m, 1H).

Example 23

Compound No. 109 of Table 3

(+)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide By analogy with the method described in example 13 (step 13.5), using 5-bromo-2,3-dihydro-benzofuran-7-carboxylic acid in place of 2-methoxy nicotinic acid, the compound, 0.022 g (8%), was obtained as a white powder.

Mp: 176-178° C. $[\alpha]_D^{20}$=+146.3° (c=0.330, DMSO).
$^1$H NMR (DMSO-d$^6$; 400 MHz)
δ (ppm): 9.35 (d, 1H), 9.10 (d, 1H), 8.45 (m, 1H), 8.32 (d, 1H), 7.65 (s, 1H), 7.55 (s, 1H), 7.30 (s, 1H), 5.02 (m, 1H), 4.85 (m, 2H), 3.81 (m, 1H), 3.81 (m, 1H), 2.31 (m, 1H), 2.15-1.82 (m, 5H), 1.90 (s, 3H), 1.35 (m, 1H).

A list of chemical structures and physical data for compounds of the aforementioned formula (I), illustrating the present invention, is given in table 1. The compounds have been prepared according to the methods of the examples. In the table, m and o represent 1, Ph represents a phenyl group, (dec.) indicates the decomposition of the compound, (Rot.) indicates the levorotatory or dextrorotatory properties of the enantiomeric compound.

The nomenclature is given according to IUPAC recommendations.

TABLE 1

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 1 | (+/−) | 2,2-dimethyl-7-methyl-2,3-dihydrobenzofuran | bond | 4-pyridyl | H | H | H | H | O | H | 0 | 200-202 | Free base |
| 2 | (+/−) | 1-methyl-5-methyl-benzotriazole | bond | 4-pyridyl | H | H | H | H | O | H | 0 | 267-269 | Free base |

TABLE 1-continued

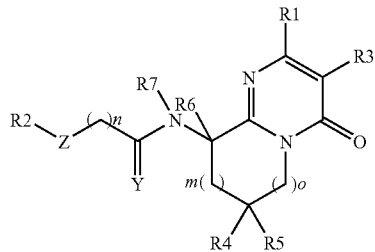

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 3 | (+/−) | quinoxalinyl-methyl | bond | 4-pyridyl | H | H | H | H | O | H | 0 | 253-255 | Free base |
| 4 | (+/−) | 2,3-dihydrobenzofuran-7-yl | bond | 4-pyrimidinyl | H | H | H | H | O | H | 0 | 294-296 | Free base |
| 5 | (+/−) | 2,2-difluoro-benzodioxol-4-yl | bond | 4-pyridyl | H | H | H | H | O | H | 0 | 228-230 | Free base |
| 6 | (+/−) | 3,4-dihydro-2H-1,5-benzodioxepin-6-yl | bond | 4-pyridyl | H | H | H | H | O | H | 0 | 194-196 | Free base |
| 7 | (+/−) | benzofuran-2-yl | bond | 4-pyridyl | H | H | H | H | O | H | 0 | 260-262 | Free base |
| 8 | (+/−) | 2,2-dimethyl-2,3-dihydrobenzofuran-7-yl | bond | 4-pyrimidinyl | H | H | H | H | O | H | 0 | 216-218 | Free base |
| 9 | (+/−) | 8-amino-7-chloro-2,3-dihydro-benzodioxin-5-yl | bond | 4-pyrimidinyl | H | H | H | H | O | H | 0 | 263-265 | Free base |

TABLE 1-continued

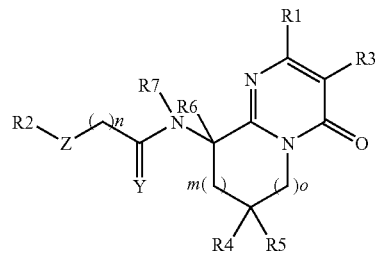

| No. | Rot | R2 | Z | R1 | R4 | R5 | R6 | R7 | Y | R3 | n | Mp ° C. | salt |
|---|---|---|---|---|---|---|---|---|---|---|---|---|---|
| 10 | (+/−) | 5-fluoro-8-methyl-4H-benzo[1,3]dioxine | bond | pyrimidin-4-yl-methyl | H | H | H | H | O | H | 0 | 253-255 | Free base |
| 11 | (+/−) | 5-fluoro-8-methyl-4H-benzo[1,3]dioxine | bond | 4-methylpyridinyl | H | H | H | H | O | H | 0 | 240-242 | Free base |
| 12 | (+/−) | 5-methyl-2,3-dihydrobenzofuran | bond | 4-methylpyridinyl | H | H | H | H | O | H | 0 | 112-114 | Free base |
| 13 | (+/−) | 5-amino-6-chloro-8-methyl-2,3-dihydro-1,4-benzodioxine | bond | 4-methylpyridinyl | H | H | H | H | O | H | 0 | 293-295 | Free base |
| 14 | (+/−) | 1,3-dimethyl-1H-indol-2-yl | bond | 4-methylpyrazinyl | H | H | H | H | O | H | 0 | 225-227 | Free base |
| 15 | (+/−) | 2-methoxy-3-methylpyridinyl | bond | 4-methylpyridinyl | H | H | H | H | O | H | 0 | 177-179 | Free base |
| 16 | (+/−) | 6-methyl-6,7-dihydro-5H-cyclopenta[b]pyridine | bond | 4-methylpyridinyl | H | H | H | H | O | H | 0 | 196-198 | Free base |

TABLE 1-continued

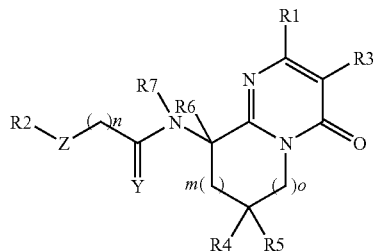

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 17 | (+/−) | 2-methoxy-3-methylpyridin-yl | bond | 4-methylpyrimidin-yl | H | H | H | H | O | H | 0 | 264-266 | Free base |
| 18 | (+/−) | 2,6-dimethoxy-3-methylpyridin-yl | bond | 4-methylpyrimidin-yl | H | H | H | H | O | H | 0 | 262-264 | Free base |
| 19 | (+/−) | 5-methyl-2-(2,2,2-trifluoroethoxy)pyridin-yl | bond | 4-methylpyrimidin-yl | H | H | H | H | O | H | 0 | 251-254 | Free base |
| 20 | (+/−) | 2-fluoro-3-methylpyridin-yl | bond | 4-methylpyrimidin-yl | H | H | H | H | O | H | 0 | 259-262 | Free base |
| 21 | (+/−) | 2-(4-methylphenoxy)-3-methylpyridin-yl | bond | 4-methylpyrimidin-yl | H | H | H | H | O | H | 0 | 220-223 | Free base |
| 22 | (+/−) | 2-(4-chlorophenoxy)-3-methylpyridin-yl | bond | 4-methylpyrimidin-yl | H | H | H | H | O | H | 0 | 217-220 | Free base |

TABLE 1-continued
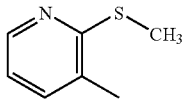
| No. | Rot | R2 | Z | R1 | R4 | R5 | R6 | R7 | Y | R3 | n | Mp °C. | salt |
|---|---|---|---|---|---|---|---|---|---|---|---|---|---|
| 23 | (+/−) | 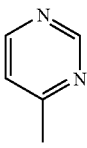 | bond | 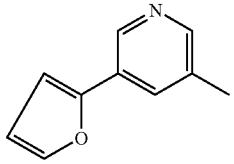 | H | H | H | H | O | H | 0 | 225-228 | Free base |
| 24 | (+/−) | 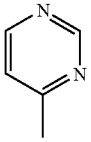 | bond | 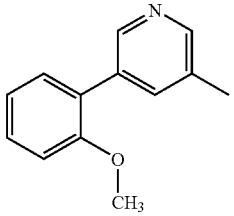 | H | H | H | H | O | H | 0 | 210-213 | Free base |
| 25 | (+/−) | 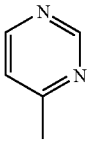 | bond | 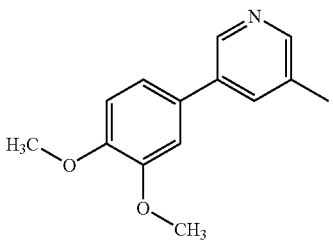 | H | H | H | H | O | H | 0 | 126-129 | Free base |
| 26 | (+/−) | 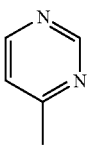 | bond | 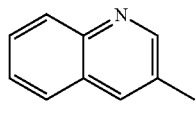 | H | H | H | H | O | H | 0 | 251-253 | Free base |
| 27 | (+/−) | 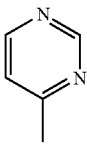 | bond | 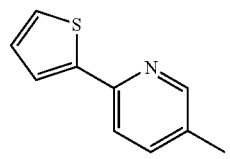 | H | H | H | H | O | H | 0 | 207-210 | Free base |
| 28 | (+/−) | 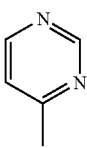 | bond |  | H | H | H | H | O | H | 0 | 256-259 | Free base |

TABLE 1-continued

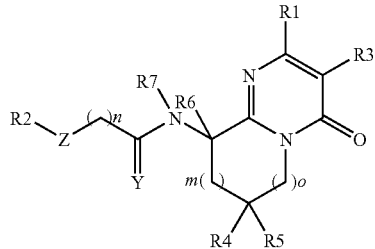

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 29 | (+/−) | tert-butyl 4-(5-methylpyridin-2-yl)-1,4-diazepane-1-carboxylate | bond | 4-methylpyrimidin-2-yl | H | H | H | H | O | H | 0 | 168-172 | Free base |
| 30 | (+/−) | 2,5-dimethylpyridine | bond | 4-methylpyrimidin-2-yl | H | H | H | H | O | H | 0 | 226-228 | Free base |
| 31 | (+/−) | 3-methyl-2-(propylthio)pyridine | bond | 4-methylpyrimidin-2-yl | H | H | H | H | O | H | 0 | 203-205 | Free base |
| 32 | (+/−) | 3-methylpyridine | bond | 4-methylpyrimidin-2-yl | H | H | H | H | O | H | 0 | 207-209 | Free base |
| 33 | (+/−) | 2-chloro-5-methylpyridine | bond | 4-methylpyrimidin-2-yl | H | H | H | H | O | H | 0 | 256-259 | Free base |
| 34 | (+/−) | 2-methoxy-3-methylpyridine | bond | 4-methylpyrimidin-2-yl | H | H | CH₃ | H | O | H | 0 | 193-195 | Free base |
| 35 | (+/−) | 4-methoxy-2-methylpyridine | bond | 4-methylpyrimidin-2-yl | H | H | H | H | O | H | 0 | 237-239 | Free base |

TABLE 1-continued

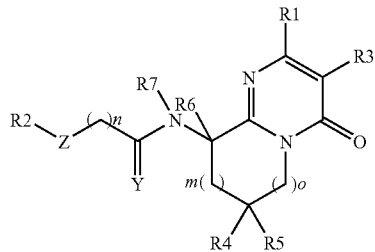

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 36 | (+/−) | 3,6-dimethoxy-4-methyl-pyridazinyl | bond | 4-methylpyrimidinyl | H | H | H | H | O | H | 0 | 244-246 | Free base |
| 37 | (+/−) | 2-methylpyridinyl | bond | 4-methylpyrimidinyl | H | H | H | H | O | H | 0 | 260-262 | Free base |
| 38 | (+/−) | 6-methoxy-2-methylpyridinyl | bond | 4-methylpyrimidinyl | H | H | H | H | O | H | 0 | 262 (dec.) | Free base |
| 39 | (+/−) | 4-methoxy-2-methylquinolinyl | bond | 4-methylpyrimidinyl | H | H | H | H | O | H | 0 | 288-290 | Free base |
| 40 | (+/−) | 1-methylisoquinolinyl | bond | 4-methylpyrimidinyl | H | H | H | H | O | H | 0 | 266-268 | Free base |
| 41 | (+/−) | 5-chloro-2-methylthio-4-methylpyrimidinyl | bond | 4-methylpyrimidinyl | H | H | CH₃ | H | O | H | 0 | 238-240 | Free base |
| 42 | (+/−) | 4-methylpyrido[3,4-d]pyridazinyl | bond | 4-methylpyrimidinyl | H | H | H | H | O | H | 0 | 283-285 | Free base |

TABLE 1-continued
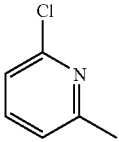
(I)
| No. | Rot | R2 | Z | R1 | R4 | R5 | R6 | R7 | Y | R3 | n | Mp °C. | salt |
|---|---|---|---|---|---|---|---|---|---|---|---|---|---|
| 43 | (+/−) | 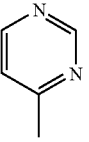 | bond | 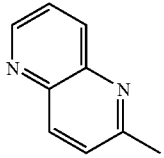 | H | H | H | H | O | H | 0 | 300 (dec.) | Free base |
| 44 | (+/−) | 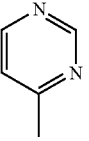 | bond | 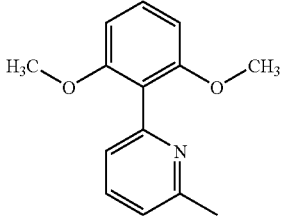 | H | H | H | H | O | H | 0 | 287 (dec.) | Free base |
| 45 | (+/−) | 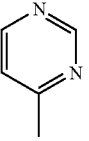 | bond | 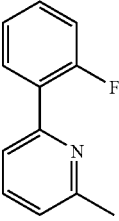 | H | H | H | H | O | H | 0 | 279 (dec.) | Free base |
| 46 | (+/−) | 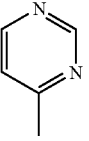 | bond | 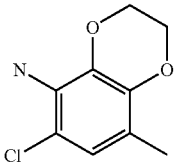 | H | H | H | H | O | H | 0 | 210-212 | Free base |
| 47 | (+/−) | 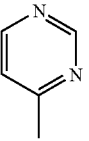 | bond | 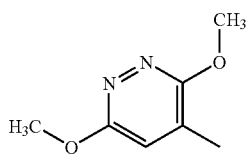 | H | H | CH$_3$ | H | O | H | 0 | 283-285 | Free base |
| 48 | (+/−) | 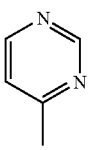 | bond | 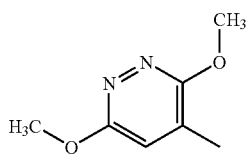 | H | H | CH$_3$ | H | O | H | 0 | 218-220 | Free base |

TABLE 1-continued

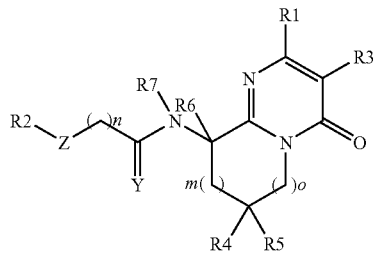

(I)

| No. | Rot | R2 | Z | R1 | R4 | R5 | R6 | R7 | Y | R3 | n | Mp °C. | salt |
|-----|-----|----|----|----|----|----|----|----|----|----|----|--------|------|
| 49 | (+/−) | 2,2-dimethyl-7-methyl-2,3-dihydrobenzofuran | bond | 4-methylpyrimidin-2-yl | H | H | CH₃ | H | O | H | 0 | 191-193 | Free base |
| 50 | (+/−) | 6-fluoro-8-methyl-4H-benzo[d][1,3]dioxine | bond | 4-methylpyrimidin-2-yl | H | H | CH₃ | H | O | H | 0 | 198-200 | Free base |
| 51 | (+/−) | 2-methyl-1,5-naphthyridine | bond | 4-methylpyrimidin-2-yl | H | H | CH₃ | H | O | H | 0 | 289-291 | Free base |
| 52 | (+/−) | 7-methyl-2,3-dihydrobenzofuran | bond | 4-methylpyrimidin-2-yl | H | H | CH₃ | H | O | H | 0 | 276-278 | Free base |
| 53 | (+/−) | 2-methylpyridine | bond | 4-methylpyrimidin-2-yl | H | H | CH₃ | H | O | H | 0 | 251-253 | Free base |
| 54 | (+/−) | 2-chloro-6-methylpyridine | bond | 4-methylpyrimidin-2-yl | H | H | CH₃ | H | O | H | 0 | 270-272 | Free base |
| 55 | (+/−) | 8-methyl-1,6-naphthyridine | bond | 4-methylpyrimidin-2-yl | H | H | CH₃ | H | O | H | 0 | 235-237 | Free base |

TABLE 1-continued

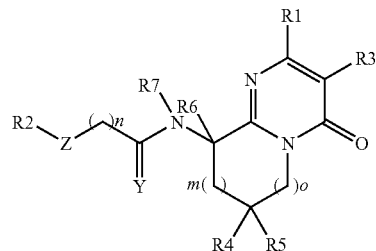

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 56 | (+/−) | 3-methylpyridin-yl | bond | 4-methylpyrimidin-yl | H | H | CH₃ | H | O | H | 0 | 236-238 | Free base |
| 57 | (+/−) | 5-bromo-2-methylbenzofuran-yl | bond | 4-methylpyrimidin-yl | H | H | CH₃ | H | O | H | 0 | 278-280 | Free base |
| 58 | (+) | 2-(2-fluorophenyl)-6-methylpyridin-yl | bond | 4-methylpyrimidin-yl | H | H | H | H | O | H | 0 | 200-202 | Free base |
| 59 | (−) | 2-(2-fluorophenyl)-6-methylpyridin-yl | bond | 4-methylpyrimidin-yl | H | H | H | H | O | H | 0 | 199-200 | Free base |
| 60 | (+) | 2-methoxy-3-methylpyridin-yl | bond | 4-methylpyrimidin-yl | H | H | CH₃ | H | O | H | 0 | 150-152 | Free base |
| 61 | (−) | 2-methoxy-3-methylpyridin-yl | bond | 4-methylpyrimidin-yl | H | H | CH₃ | H | O | H | 0 | 139-141 | Free base |
| 62 | (+) | 2-methyl-1,5-naphthyridin-yl | bond | 4-methylpyrimidin-yl | H | H | H | H | O | H | 0 | 282-284 | Free base |

TABLE 1-continued

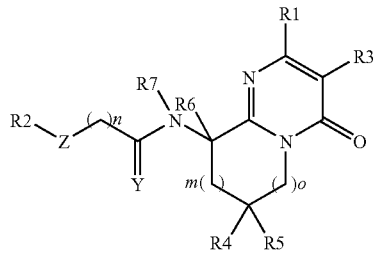

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 63 | (−) | (1,5-naphthyridin-2-yl methyl) | bond | (pyrimidin-4-yl) | H | H | H | H | O | H | 0 | 272-274 | Free base |

A list of chemical structures and physical data for compounds of the aforementioned formula (I), illustrating the present invention, is given in table 2. The compounds have been prepared according to the methods of the examples.

In the table, m represents 0 and o represents 1, (Rot.) indicates the levorotatory or dextrorotatory properties of the enantiomeric compound.

TABLE 2

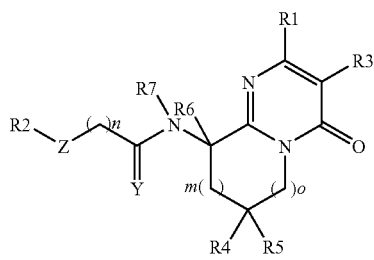

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 1 | (+/−) | 2,2,7-trimethyl-2,3-dihydrobenzofuran | bond | (pyridin-4-yl) | H | H | H | H | O | H | 0 | 206-208 | Free base |
| 2 | (+/−) | 1,5-dimethyl-1H-benzotriazole | bond | (pyridin-4-yl) | H | H | H | H | O | H | 0 | 393-395 | Free base |
| 3 | (+/−) | 8-amino-7-chloro-5-methyl-2,3-dihydro-1,4-benzodioxine | bond | (pyridin-4-yl) | H | H | H | H | O | H | 0 | 291-293 | Free base |

TABLE 2-continued (I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 4 | (+/−) | 5-fluoro-8-methyl-4H-benzo[d][1,3]dioxine | bond | 4-pyridyl | H | H | H | H | O | H | 0 | 183-185 | Free base |
| 5 | (+/−) | 6-methylquinoxaline | bond | 4-pyridyl | H | H | H | H | O | H | 0 | 238-240 | Free base |
| 6 | (+/−) | 5-methyl-2,3-dihydrobenzofuran | bond | 4-pyridyl | H | H | H | H | O | H | 0 | 149-151 | Free base |
| 7 | (+/−) | 1,3-dimethyl-1H-indole | bond | 4-pyridyl | H | H | H | H | O | H | 0 | 170-172 | Free base |
| 8 | (+/−) | 5-bromo-7-methyl-2,3-dihydrobenzofuran | bond | 4-pyridyl | H | H | H | H | O | H | 0 | 240-242 | Free base |
| 9 | (+/−) | 2-methyl-2,3-dihydrobenzofuran | bond | 4-pyridyl | H | H | H | H | O | H | 0 | 110-112 | Free base |
| 10 | (+/−) | 6-methyl-6,7-dihydro-5H-cyclopenta[b]pyridine | bond | 4-pyridyl | H | H | H | H | O | H | 0 | 101-103 | Free base |

TABLE 2-continued (I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 11 | (+/−) | benzofuran-2-yl | bond | pyridin-4-yl | H | H | H | H | O | H | 0 | 233-235 | Free base |
| 12 | (+/−) | 1,5-naphthyridin-2-yl | bond | pyrimidin-4-yl | H | H | H | H | O | H | 0 | 283 (dec.) | Free base |
| 13 | (+/−) | 2-methoxy-3-methylpyridin-yl | bond | pyrimidin-4-yl | H | H | H | H | O | H | 0 | 264-266 | Free base |
| 14 | (+/−) | 5-chloro-4-methyl-2-(methylthio)pyrimidin-yl | bond | pyrimidin-4-yl | H | H | H | H | O | H | 0 | 232-234 | Free base |
| 15 | (+/−) | isoquinolin-1-yl | bond | pyrimidin-4-yl | H | H | H | H | O | H | 0 | 226-228 | Free base |
| 16 | (+/−) | 2-methoxy-3-methylpyridin-yl | bond | pyridin-4-yl | H | H | H | H | O | H | 0 | 244 (dec.) | Free base |
| 17 | (+/−) | 5-chloro-4-methyl-2-(methylthio)pyrimidin-yl | bond | pyridin-4-yl | H | H | H | H | O | H | 0 | 260-263 | Free base |

TABLE 2-continued

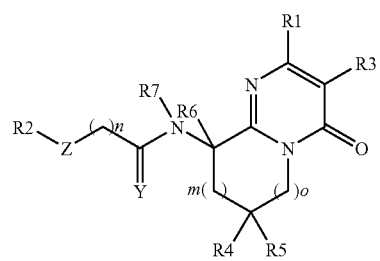

| No. | Rot | R2 | Z | R1 | R4 | R5 | R6 | R7 | Y | R3 | n | Mp °C. | salt |
|-----|-----|----|----|----|----|----|----|----|----|----|---|--------|------|
| 18 | (+/−) | (isoquinolinyl-methyl) | bond | (4-pyridyl) | H | H | H | H | O | H | 0 | 230-232 | Free base |
| 19 | (+/−) | (2-pyridyl-methyl) | bond | (4-pyrimidinyl) | H | H | H | H | O | H | 0 | 187-190 | Free base |
| 20 | (+/−) | (6-chloro-2-pyridyl-methyl) | bond | (4-pyridyl) | H | H | H | H | O | H | 0 | 201 (dec.) | Free base |
| 21 | (+/−) | (1,5-naphthyridinyl-methyl) | bond | (4-pyridyl) | H | H | H | H | O | H | 0 | 242-244 | Free base |

A list of chemical structures and physical data for compounds of the aforementioned formula (I), illustrating the present invention, is given in table 3. The compounds have been prepared according to the methods of the examples.

In the table 3, m represents 1 and o represents 2, (dec.) indicates the decomposition of the compound, (Rot.) indicates the levorotatory or dextrorotatory properties of the enantiomeric compound.

TABLE 3

(I)

[Structure of formula (I) shown with substituents R1, R2, R3, R4, R5, R6, R7, Y, Z, n, m, o]

| No. | Rot | R2 | Z | R1 | R4 | R5 | R6 | R7 | Y | R3 | n | Mp ° C. | salt |
|---|---|---|---|---|---|---|---|---|---|---|---|---|---|
| 1 | (+/−) | 4-amino-6-chloro-8-methyl-2,3-dihydro-1,4-benzodioxine | bond | 4-methylpyrimidin-2-yl | H | H | H | H | O | H | 0 | 286-288 | Free base |
| 2 | (+/−) | 2-methoxy-3-methylpyridin-4-yl | bond | 4-methylpyrimidin-2-yl | H | H | H | H | O | H | 0 | 202-204 | Free base |
| 3 | (+/−) | 5-bromo-7-methyl-2,3-dihydrobenzofuran-4-yl | bond | 4-methylpyrimidin-2-yl | H | H | H | H | O | H | 0 | 287-289 | Free base |
| 4 | (+/−) | 6-fluoro-8-methyl-4H-benzo[d][1,3]dioxin-5-yl | bond | 4-methylpyrimidin-2-yl | H | H | H | H | O | H | 0 | 269-271 | Free base |
| 5 | (+/−) | 5-chloro-7-methyl-2,3-dihydrobenzofuran-4-yl | bond | 4-methylpyrimidin-2-yl | H | H | H | H | O | H | 0 | 259-261 | Free base |
| 6 | (+/−) | 7-methyl-2,3-dihydrobenzofuran-4-yl | bond | 4-methylpyrimidin-2-yl | H | H | H | H | O | H | 0 | 260-262 | Free base |

TABLE 3-continued
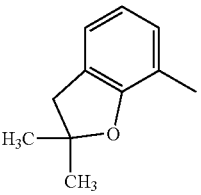
(I)
| No. | Rot | R2 | Z | R1 | R4 | R5 | R6 | R7 | Y | R3 | n | Mp ° C. | salt |
|---|---|---|---|---|---|---|---|---|---|---|---|---|---|
| 7 | (+/−) | 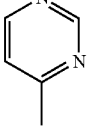 | bond | 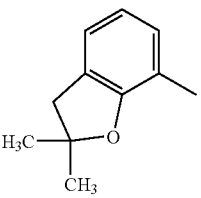 | H | H | H | H | O | H | 0 | 230-232 | Free base |
| 8 | (+/−) | 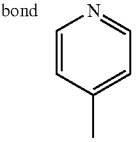 | bond | 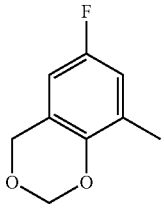 | H | H | H | H | O | H | 0 | 193-195 | Free base |
| 9 | (+/−) | 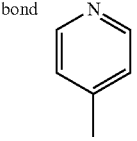 | bond | 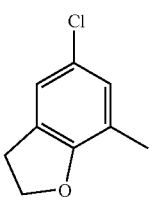 | H | H | H | H | O | H | 0 | 213-215 | Free base |
| 10 | (+/−) | 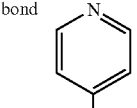 | bond | 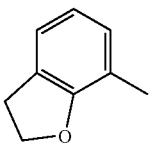 | H | H | H | H | O | H | 0 | 284-285 | Free base |
| 11 | (+/−) | 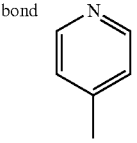 | bond | 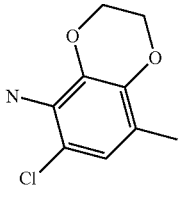 | H | H | H | H | O | H | 0 | 250-252 | Free base |
| 12 | (+/−) | 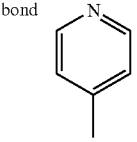 | bond |  | H | H | H | H | O | H | 0 | 309-311 | Free base |

TABLE 3-continued

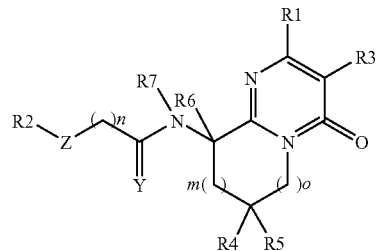

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 13 | (+/−) | 3-methyl-2-methoxypyridine | bond | 4-pyridyl | H | H | H | H | O | H | 0 | 198-200 | Free base |
| 14 | (+) | 3-methyl-2-methoxypyridine | bond | 4-methylpyrimidine | H | H | H | H | O | H | 0 | 214-216 | Free base |
| 15 | (−) | 3-methyl-2-methoxypyridine | bond | 4-methylpyrimidine | H | H | H | H | O | H | 0 | 212-214 | Free base |
| 16 | (+/−) | 2,6-dimethoxy-3-methylpyridine | bond | 4-pyridyl | H | H | H | H | O | H | 0 | 216-218 | Free base |
| 17 | (+/−) | 5-methyl-2-(2,2,2-trifluoroethoxy)pyridine | bond | 4-pyridyl | H | H | H | H | O | H | 0 | 248-250 | Free base |
| 18 | (+/−) | 2-fluoro-3-methylpyridine | bond | 4-pyridyl | H | H | H | H | O | H | 0 | 258-260 | Free base |
| 19 | (+/−) | 3-methyl-2-(methylthio)pyridine | bond | 4-pyridyl | H | H | H | H | O | H | 0 | 217-219 | Free base |

TABLE 3-continued

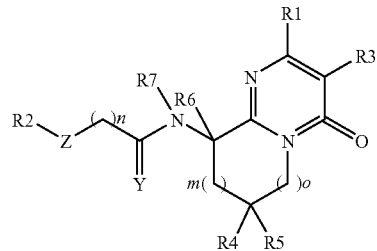

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 20 | (+/−) | 3-methyl-2-(4-methylphenoxy)pyridine | bond | 4-methylpyridine | H | H | H | H | O | H | 0 | 256-258 | Free base |
| 21 | (+/−) | 2-(4-chlorophenoxy)-3-methylpyridine | bond | 4-methylpyridine | H | H | H | H | O | H | 0 | 243-245 | Free base |
| 22 | (+/−) | 6-methyl-imidazo[4,5-b]pyridine | bond | 4-methylpyridine | H | H | H | H | O | H | 0 | 300-302 | Free base |
| 23 | (+/−) | 5-methyl-2-(thiophen-2-yl)pyridine | bond | 4-methylpyridine | H | H | H | H | O | H | 0 | 276-278 | Free base |
| 24 | (+/−) | 2,5-dimethylpyridine | bond | 4-methylpyridine | H | H | H | H | O | H | 0 | 212-214 | Free base |
| 25 | (+/−) | 5-(furan-2-yl)-3-methylpyridine | bond | 4-methylpyridine | H | H | H | H | O | H | 0 | >210 (dec.) | Free base |

TABLE 3-continued

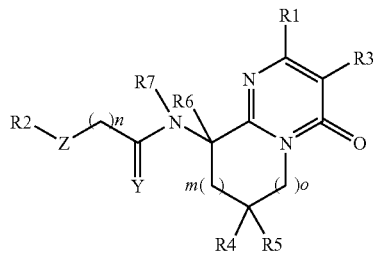

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 26 | (+/−) | 2-methoxyphenyl-5-(5-methylpyridin-3-yl) | bond | 4-methylpyridin-2-yl | H | H | H | H | O | H | 0 | >125 | Free base |
| 27 | (+/−) | 3,4-dimethoxyphenyl-5-(5-methylpyridin-3-yl) | bond | 4-methylpyridin-2-yl | H | H | H | H | O | H | 0 | 215-217 | Free base |
| 28 | (+/−) | 3-(5-methyl)-quinoline | bond | 4-methylpyridin-2-yl | H | H | H | H | O | H | 0 | 253-255 | Free base |
| 29 | (+/−) | tert-butyl 4-(5-methylpyridin-2-yl)-1,4-diazepane-1-carboxylate | bond | 4-methylpyridin-2-yl | H | H | H | H | O | H | 0 | 247-249 | Free base |
| 30 | (+/−) | 4-bromophenyl-3-(5-methylpyridin-3-yl) | bond | 4-methylpyridin-2-yl | H | H | H | H | O | H | 0 | 242-244 | Free base |

TABLE 3-continued

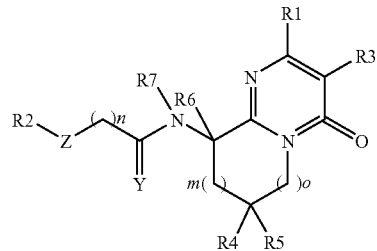

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 31 | (+/−) | 3-methylpyridine | bond | 4-methylpyridine | H | H | H | H | O | H | 0 | 301-303 | Free base |
| 32 | (+/−) | 2-Cl-5-methylpyridine | bond | 4-methylpyridine | H | H | H | H | O | H | 0 | 265-267 | Free base |
| 33 | (+/−) | 2-Cl-3-methylpyridine | bond | 4-methylpyridine | H | H | H | H | O | H | 0 | 238-240 | Free base |
| 34 | (+/−) | 2-(phenylthio)-3-methylpyridine | bond | 4-methylpyridine | H | H | H | H | O | H | 0 | >233 (dec.) | Free base |
| 35 | (+/−) | 2-(propylthio)-3-methylpyridine | bond | 4-methylpyridine | H | H | H | H | O | H | 0 | 159-161 | Free base |
| 36 | (+/−) | 2-(4-chlorophenylthio)-3-methylpyridine | bond | 4-methylpyridine | H | H | H | H | O | H | 0 | 244-246 | Free base |

TABLE 3-continued

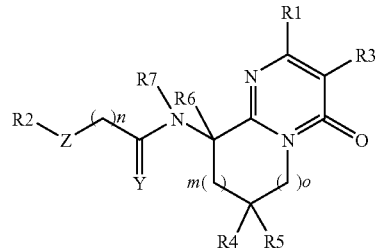

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 37 | (+/−) | 2-phenyl-4,5-dimethyl-pyrimidine | bond | 4-methyl-pyrimidine | H | H | H | H | O | H | 0 | 258-260 | Free base |
| 38 | (+/−) | 5-methyl-pyrimidine | bond | 4-methyl-pyrimidine | H | H | H | H | O | H | 0 | 279-282 | Free base |
| 39 | (+/−) | 2-methylthio-4-methyl-5-chloro-pyrimidine | bond | 4-methyl-pyrimidine | H | H | H | H | O | H | 0 | 250-253 | Free base |
| 40 | (+/−) | 4-methyl-pyridazine | bond | 4-methyl-pyrimidine | H | H | H | H | O | H | 0 | 255-258 | Free base |
| 41 | (+/−) | 6-phenyl-4-methyl-pyrimidine | bond | 4-methyl-pyrimidine | H | H | H | H | O | H | 0 | 264-267 | Free base |
| 42 | (+/−) | 4-methyl-cinnoline | bond | 4-methyl-pyrimidine | H | H | H | H | O | H | 0 | 277-281 | Free base |
| 43 | (+/−) | 3,6-dimethoxy-4-methyl-pyridazine | bond | 4-methyl-pyrimidine | H | H | H | H | O | H | 0 | 250-254 | Free base |
| 44 | (+/−) | 1-methyl-isoquinoline | bond | 4-methyl-pyridine | H | H | H | H | O | H | 0 | 265-267 | Free base |

TABLE 3-continued
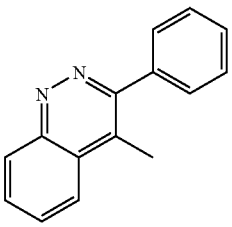
(I)
| No. | Rot | R2 | Z | R1 | R4 | R5 | R6 | R7 | Y | R3 | n | Mp ° C. | salt |
|---|---|---|---|---|---|---|---|---|---|---|---|---|---|
| 45 | (+/−) | 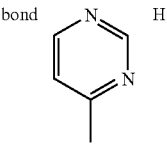 | bond | 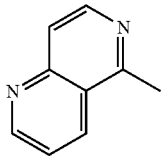 | H | H | H | H | O | H | 0 | 252-254 | Free base |
| 46 | (+/−) | 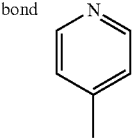 | bond | 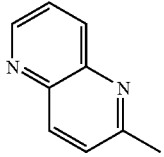 | H | H | H | H | O | H | 0 | >270 (dec.) | Free base |
| 47 | (+/−) | 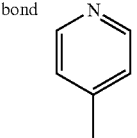 | bond | 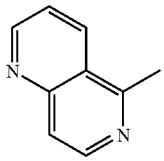 | H | H | H | H | O | H | 0 | 297-299 | Free base |
| 48 | (+/−) | 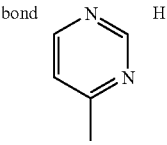 | bond | 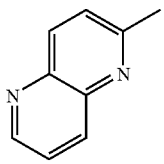 | H | H | H | H | O | H | 0 | 301-304 | Free base |
| 49 | (+/−) | 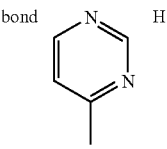 | bond | 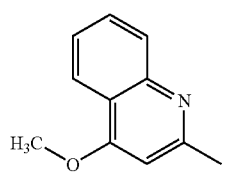 | H | H | H | H | O | H | 0 | 298-301 | Free base |
| 50 | (+/−) | 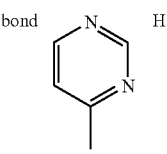 | bond | 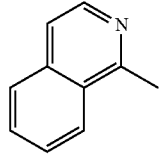 | H | H | H | H | O | H | 0 | 300-302 | Free base |
| 51 | (+/−) | 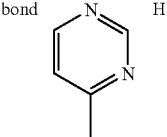 | bond |  | H | H | H | H | O | H | 0 | 287-290 | Free base |

TABLE 3-continued

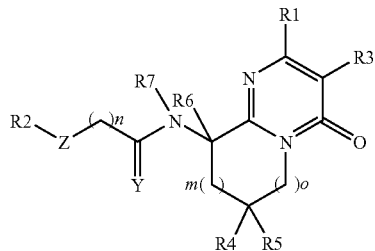

| No. | Rot | R2 | Z | R1 | R4 | R5 | R6 | R7 | Y | R3 | n | Mp ° C. | salt |
|---|---|---|---|---|---|---|---|---|---|---|---|---|---|
| 52 | (+/−) | 3-methylpyridin-2-yl | bond | 4-methylpyrimidin-2-yl | H | H | H | H | O | H | 0 | 282-285 | Free base |
| 53 | (+/−) | 6-chloro-2-methylpyridin-3-yl | bond | 4-methylpyrimidin-2-yl | H | H | H | H | O | H | 0 | 303-305 | Free base |
| 54 | (+/−) | 4-methoxy-2-methylpyridin-3-yl | bond | 4-methylpyrimidin-2-yl | H | H | H | H | O | H | 0 | 282-286 | Free base |
| 55 | (+/−) | 3,5-difluoro-2-methylpyridin-? | bond | 4-methylpyrimidin-2-yl | H | H | H | H | O | H | 0 | 271-274 | Free base |
| 56 | (+/−) | 2,6-dimethoxy-6'-methyl-bipyridinyl | bond | 4-methylpyrimidin-2-yl | H | H | H | H | O | H | 0 | 293-296 | Free base |
| 57 | (+/−) | 4,5-dimethyl-2-phenylpyrimidin-? | bond | 4-methylpyridin-2-yl | H | H | H | H | O | H | 0 | 125-127 | Free base |
| 58 | (+/−) | 4-methyl-3-phenylcinnolin-? | bond | 4-methylpyridin-2-yl | H | H | H | H | O | H | 0 | >288 (dec.) | Free base |

TABLE 3-continued

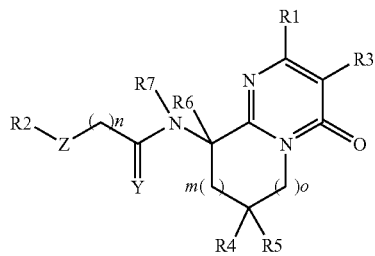

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 59 | (+/−) | 3,6-dimethoxy-4-methylpyridazine | bond | 4-pyridyl | H | H | H | H | O | H | 0 | 277-279 | Free base |
| 60 | (+/−) | 2-methyl-4-phenyl-5-methylpyrimidine | bond | 4-pyridyl | H | H | H | H | O | H | 0 | 232-234 | Free base |
| 61 | (+/−) | 6-phenyl-4-methylpyrimidine | bond | 4-pyridyl | H | H | H | H | O | H | 0 | >247 (dec.) | Free base |
| 62 | (+/−) | 2-(2-fluorophenyl)-6-methylpyridine | bond | 4-pyrimidyl | H | H | H | H | O | H | 0 | 250-253 | Free base |
| 63 | (+/−) | 2,6-dimethoxy-3-methylpyridine | bond | 4-pyrimidyl | H | H | H | H | O | H | 0 | 246-249 | Free base |
| 64 | (+/−) | 2-(2,2,2-trifluoroethoxy)-5-methylpyridine | bond | 4-pyrimidyl | H | H | H | H | O | H | 0 | 270-273 | Free base |
| 65 | (+/−) | 2-fluoro-3-methylpyridine | bond | 4-pyrimidyl | H | H | H | H | O | H | 0 | 275-279 | Free base |

TABLE 3-continued

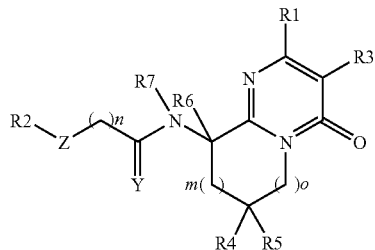

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 66 | (+/−) | 5-(furan-2-yl)-3-methylpyridine | bond | 4-methylpyrimidine | H | H | H | H | O | H | 0 | 265-268 | Free base |
| 67 | (+/−) | 2-methoxy-6-methylpyridine | bond | 4-methylpyrimidine | H | H | H | H | O | H | 0 | 251-254 | Free base |
| 68 | (+/−) | 3-methylquinoline | bond | 4-methylpyrimidine | H | H | H | H | O | H | 0 | 260-263 | Free base |
| 69 | (+/−) | tert-butyl 4-(5-methylpyridin-2-yl)-1,4-diazepane-1-carboxylate | bond | 4-methylpyrimidine | H | H | H | H | O | H | 0 | 234-236 | Free base |
| 70 | (+/−) | 5-(2-methoxyphenyl)-3-methylpyridine | bond | 4-methylpyrimidine | H | H | H | H | O | H | 0 | 188-190 | Free base |
| 71 | (+/−) | 5-(3,4-dimethoxyphenyl)-3-methylpyridine | bond | 4-methylpyrimidine | H | H | H | H | O | H | 0 | 234-237 | Free base |

TABLE 3-continued

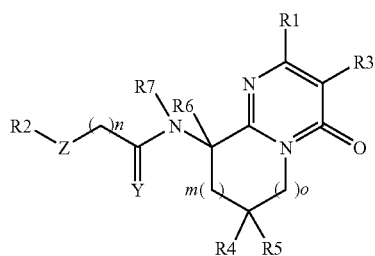

| No. | Rot | R2 | Z | R1 | R4 | R5 | R6 | R7 | Y | R3 | n | Mp °C. | salt |
|---|---|---|---|---|---|---|---|---|---|---|---|---|---|
| 72 | (+/−) | 2,4-dimethoxy-6-methylpyrimidinyl | bond | pyrimidinyl | H | H | H | H | O | H | 0 | 259-261 | Free base |
| 73 | (+/−) | 5-bromo-2-methylthio-4-methylpyrimidinyl | bond | pyrimidinyl | H | H | H | H | O | H | 0 | 260-262 | Free base |
| 74 | (+/−) | 2-methyl-1,5-naphthyridinyl | bond | pyrimidinyl | H | H | CH₃ | H | O | H | 0 | 261-263 | Free base |
| 75 | (+/−) | 6-methoxy-2-methylpyridinyl | bond | pyrimidinyl | H | H | CH₃ | H | O | H | 0 | 195-197 | Free base |
| 76 | (+/−) | 5-bromo-7-methyl-2,3-dihydrobenzofuranyl | bond | pyrimidinyl | H | H | CH₃ | H | O | H | 0 | 169-171 | Free base |
| 77 | (+/−) | 2-methoxy-3-methylpyridinyl | bond | pyrimidinyl | H | H | CH₂CH₃ | H | O | H | 0 | 120-122 | Free base |
| 78 | (+/−) | 2-methoxy-3-methylpyridinyl | bond | pyridinyl | H | H | CH₃ | H | O | H | 0 | 180-182 | Free base |

TABLE 3-continued

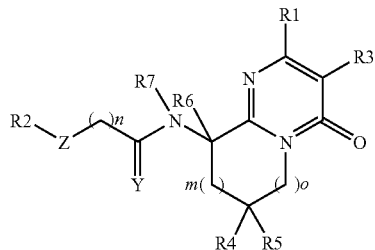

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 79 | (+/−) | 7-methyl-2,3-dihydrobenzofuran | bond | 4-pyridyl | H | H | CH₃ | H | O | H | 0 | 213-215 | Free base |
| 80 | (+/−) | 2-methoxy-3-methylpyridine | bond | 4-pyrimidinyl | H | H | CH₃ | H | O | H | 0 | 194-196 | Free base |
| 81 | (+/−) | 7-methyl-2,3-dihydrobenzofuran | bond | 4-pyrimidinyl | H | H | CH₃ | H | O | H | 0 | 193-195 | Free base |
| 82 | (+/−) | 6-fluoro-8-methyl-4H-benzo[d][1,3]dioxine | bond | 4-pyrimidinyl | H | H | CH₃ | H | O | H | 0 | 140 (dec.) | Free base |
| 83 | (+/−) | 2,6-dimethoxy-3-methylpyridine | bond | 4-pyrimidinyl | H | H | CH₃ | H | O | H | 0 | 179-181 | Free base |
| 84 | (+/−) | 2-methylpyridine | bond | 4-pyrimidinyl | H | H | CH₃ | H | O | H | 0 | 229-231 | Free base |
| 85 | (+/−) | 3-methoxy-6-methylpyridine | bond | 4-pyrimidinyl | H | H | CH₃ | H | O | H | 0 | 212-214 | Free base |

TABLE 3-continued

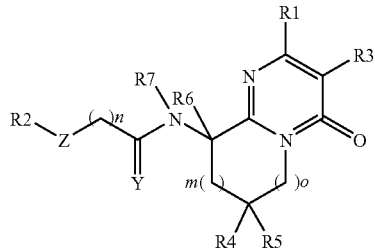

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 86 | (+/−) | (3,6-dimethoxy-4-methylpyridazinyl) | bond | (4-methylpyrimidinyl) | H | H | CH₃ | H | O | H | 0 | 217-219 | Free base |
| 87 | (+/−) | (6-chloro-2-methylpyridinyl) | bond | (4-methylpyrimidinyl) | H | H | CH₃ | H | O | H | 0 | 231-233 | Free base |
| 88 | (+/−) | (5-amino-6-chloro-8-methyl-benzodioxinyl) | bond | (4-methylpyrimidinyl) | H | H | CH₃ | H | O | H | 0 | 318-320 | Free base |
| 89 | (+/−) | (5-bromo-4-methyl-2-methylthiopyrimidinyl) | bond | (4-methylpyrimidinyl) | H | H | CH₃ | H | O | H | 0 | 201-203 | Free base |
| 90 | (+/−) | (6-bromo-2-methylpyridinyl) | bond | (4-methylpyrimidinyl) | H | H | CH₃ | H | O | H | 0 | 224-226 | Free base |
| 91 | (+/−) | (3,5-difluoro-2-methylpyridinyl) | bond | (4-methylpyrimidinyl) | H | H | CH₃ | H | O | H | 0 | 250-252 | Free base |
| 92 | (+/−) | (2,2,7-trimethyl-2,3-dihydrobenzofuranyl) | bond | (4-methylpyrimidinyl) | H | H | CH₃ | H | O | H | 0 | 171-173 | Free base |

TABLE 3-continued

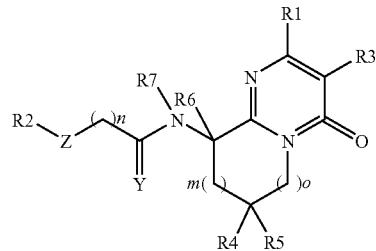

(I)

| No. | Rot | R2 | Z | R1 | R4 | R5 | R6 | R7 | Y | R3 | n | Mp ° C. | salt |
|---|---|---|---|---|---|---|---|---|---|---|---|---|---|
| 93 | (+/−) | 2-methyl-4-methoxypyridinyl | bond | 4-methylpyrimidinyl | H | H | CH₂CH₃ | H | O | H | 0 | 200-202 | Free base |
| 94 | (+/−) | 5-chloro-7-methyl-2,3-dihydrobenzofuranyl | bond | 4-methylpyrimidinyl | H | H | CH₃ | H | O | H | 0 | 205-207 | Free base |
| 95 | (+/−) | 5-chloro-4-methyl-2-methylthiopyrimidinyl | bond | 4-methylpyrimidinyl | H | H | CH₃ | H | O | H | 0 | 198-200 | Free base |
| 96 | (+/−) | 5-amino-6-chloro-8-methyl-4H-benzo[d][1,3]dioxinyl | bond | 4-methylpyrimidinyl | H | H | CH₂CH₃ | H | O | H | 0 | 296-299 | Free base |
| 97 | (+/−) | 3,6-dimethoxy-4-methylpyridazinyl | bond | 4-methylpyrimidinyl | H | H | CH₂CH₃ | H | O | H | 0 | 211-213 | Free base |
| 98 | (+/−) | 6-fluoro-8-methyl-4H-benzo[d][1,3]dioxinyl | bond | 4-methylpyrimidinyl | H | H | CH₂CH₃ | H | O | H | 0 | 204-206 | Free base |

TABLE 3-continued

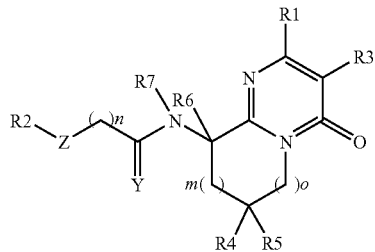

(I)

| No. | Rot | R2 | Z | R1 | R4 | R5 | R6 | R7 | Y | R3 | n | Mp °C. | salt |
|---|---|---|---|---|---|---|---|---|---|---|---|---|---|
| 99 | (+/−) | 2,6-dimethoxy-3-methylpyridin-4-yl | bond | pyrimidin-4-yl | H | H | CH₂CH₃ | H | O | H | 0 | 146-148 | Free base |
| 100 | (+/−) | 2-methoxy-3-methylpyridin-4-yl | bond | pyrimidin-4-yl | H | H | H | H | O | Br | 0 | 190-192 | Free base |
| 101 | (+/−) | 6-chloro-2-methylpyridin-4-yl | bond | pyrimidin-4-yl | H | H | CH₂CH₃ | H | O | H | 0 | 194-196 | Free base |
| 102 | (+/−) | 2,4-dimethoxy-6-methylpyrimidin-5-yl | bond | pyrimidin-4-yl | H | H | H | H | O | H | 0 | 199-200 | Free base |
| 103 | (−) | 2,4-dimethoxy-6-methylpyrimidin-5-yl | bond | pyrimidin-4-yl | H | H | H | H | O | H | 0 | 200-202 | Free base |
| 104 | (+) | 2-methoxy-3-methylpyridin-4-yl | bond | pyrimidin-4-yl | H | H | CH₃ | H | O | H | 0 | 109-111 | Free base |
| 105 | (−) | 2,6-dimethoxy-3-methylpyridin-4-yl | bond | pyrimidin-4-yl | H | H | CH₃ | H | O | H | 0 | 114 (dec) | Free base |

TABLE 3-continued

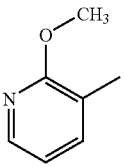

| No. | Rot | R2 | Z | R1 | R4 | R5 | R6 | R7 | Y | R3 | n | Mp °C. | salt |
|---|---|---|---|---|---|---|---|---|---|---|---|---|---|
| 106 | (−) | 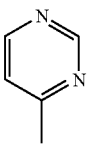 | bond | 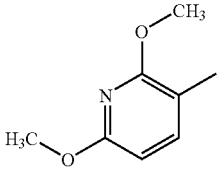 | H | H | $CH_3$ | H | O | H | 0 | 111 (dec) | Free base |
| 107 | (+) | 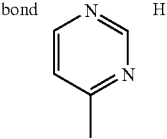 | bond | 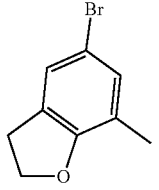 | H | H | $CH_3$ | H | O | H | 0 | 89-91 | Free base |
| 108 | (−) | 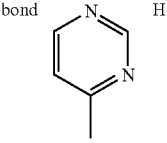 | bond | 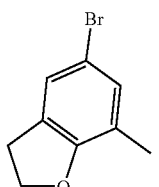 | H | H | $CH_3$ | H | O | H | 0 | 126 (dec) | Free base |
| 109 | (+) | 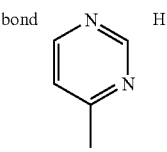 | bond | | H | H | $CH_3$ | H | O | H | 0 | 176-178 | Free base |

Test Example

Inhibitory Activity of the Medicament of the Present Invention Against GSK3β

Two different protocols can be used.

In a first protocol: 7.5 μM of prephosphorylated GS1 peptide and 10 μM ATP (containing 300,000 cpm of $^{33}$P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3beta (total reaction volume: 100 microliters).

In a second protocol: 4.1 μM of prephosphorylated GS1 peptide and 42 μM ATP (containing 260,000 cpm $^{33}$P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta.

Inhibitors were solubilized in DMSO (final solvent concentration in the reaction medium, 1%).

The reaction was stopped with 100 microliters of a solution made of 25 g polyphosphoric acid (85% $P_2O_5$), 126 ml 85% $H_3PO_4$, $H_2O$ to 500 ml and then diluted to 1:100 before use. An aliquot of the reaction mixture was then transferred to Whatman P81 cation exchange filters and rinsed with the solution described above. Incorporated $^{33}$P radioactivity was determined by liquid scintillation spectrometry.

The phosphorylated GS-1 peptide had the following sequence:

$NH_2$—YRRAAVPPSPSLSRHSSPHQS(P)EDEE-COOH. (Woodgett, J. R. (1989) Analytical Biochemistry 180, 237-241.

The GSK3β inhibitory activity of the compounds of the present invention are expressed in $IC_{50}$, and as an illustration the range of $IC_{50}$'s of the compounds in table 1 is between 0.01 nanomolar to 3 micromolar concentrations.

For example compound No. 13 of table 1 shows an $IC_{50}$ of 0.014 μM, compound 14 of table 2 shows an IC50 of 0.004 μM and compound 53 of table 3 shows an IC50 of 0.005 μM.

Formulation Example (1) Tablets

The ingredients below were mixed by an ordinary method and compressed by using a conventional apparatus.

| Compound of Example 1 | 30 mg |
|---|---|
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| Compound of Example 1 | 30 mg |
|---|---|
| Olive oil | 300 mg |
| Lecithin | 20 mg |

(1) Parenteral Preparations

The ingredients below were mixed by an ordinary method to prepare injections contained in a 1 ml ampoule.

| Compound of Example 1 | 3 mg |
|---|---|
| Sodium chloride | 4 mg |
| Distilled water for injection | 1 ml |

Industrial Applicability

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:

1. A compound of formula (I) or a salt thereof:

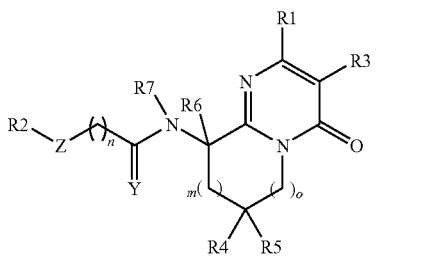

wherein:
Y represents a sulfur atom or an oxygen atom;
Z represents a bond;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a 4-15 membered heterocyclic group, which is being optionally substituted by 1 to 4 substituents selected from a $C_{1-6}$ alkyl group, a halogen atom, a $C_{1-2}$ perhalogenated alkyl group, a $C_{1-6}$ halogenated alkyl group, a hydroxyl group, a $C_{1-6}$ alkoxy group, a $C_{1-2}$ perhalogenated alkoxy group, a $C_{1-6}$ halogenated alkoxy group, a nitro, a cyano, an amino, a $C_{1-6}$ monoalkylamino group, a $C_{2-12}$ dialkylamino group, a S—($C_{1-6}$-alkyl) group, an 4-15 membered heterocyclic group, an aryl group, a O-aryl group and a S-aryl group, the above-mentioned groups being optionally substituted by 1 to 4 substituents selected from a $C_{1-6}$ alkyl group, a halogen atom, a ($C_{1-6}$) alkoxy group, a $C(O)O(C_{1-6}$-alkyl) and a C(O)O(aryl) group;
R3 represents a hydrogen atom, a $C_{1-6}$ alkyl group or a halogen atom;
R4 and R5 represent, each independently, a hydrogen atom, a $C_{1-6}$ alkyl group, optionally substituted by 1 to 4 substituents selected from a halogen atom, a phenyl group, a hydroxyl group and a $C_{1-6}$ alkoxy group;
R6 represents a hydrogen atom, a $C_{1-6}$ alkyl group optionally substituted by a halogen atom or a cycloalkyl group, or a halogen atom;
R7 represents a hydrogen atom or a $C_{1-6}$ alkyl group;
n represents 0; m represents 0 to 1; and o represents 0 to 2.

2. The compound according to claim 1, wherein R1 represents an unsubstituted 4-pyridine ring or unsubstituted 4-pyrimidine ring.

3. The compound according to claim 1, wherein R2 represents a benzotriazole group, quinoxaline group, benzodioxepine group, benzodioxane group, benzodioxine group, benzodioxole group, indole group, pyridine group, pyrindine group, quinoline group, pyridazine group, isoquinoline group, pyrimidine group, naphthyridine group, imidazopyridine group, cinnoline group or benzofuran group and wherein the above-mentioned groups are being optionally substituted by 1 to 4 substituents selected from a $C_{1-6}$ alkyl group, a halogen atom, a $C_{1-6}$ alkoxy group, a $C_{1-2}$ perhalogenated alkoxy group, an amino, a S—$C_{1-6}$-alkyl group, a furan group, a thiophene group, a [1,4]diazepane, a phenyl group, a O-phenyl group and a S-phenyl group, the above -mentioned groups being optionally substituted by 1 to 4 substituents selected from a $C_{1-6}$ alkyl group, a halogen atom, a $C_{1-6}$ alkoxy group, and a C(O)O $C_{1-6}$-alkyl.

4. The compound according to claim 1, wherein R4 and R5 represent a hydrogen atom;
(m+o) represents 2 or 3;
R2 represents a benzotriazole group, quinoxaline group, benzodioxepine group, benzodioxane group, benzodioxine group, benzodioxole group, indole group, pyridine group, pyrindine group, quinoline group, pyridazine group, isoquinoline group, pyrimidine group, naphthyridine group, imidazopyridine group, cinnoline group or benzofuran group and wherein the above-mentioned groups are being optionally substituted by 1 to 4 substituents selected from a $C_{1-6}$ alkyl group, a halogen atom, a $C_{1-6}$ alkoxy group, a $C_{1-2}$ perhalogenated alkoxy group, an amino, a S—$C_{1-6}$-alkyl group, a furan group, a thiophene group, a [1,4]diazepane, a phenyl group, a O-phenyl group and a S-phenyl group, and wherein the above-mentioned groups are being optionally substituted by 1 to 4 substituents selected from a $C_{1-6}$ alkyl group, a halogen atom, a $C_{1-6}$ alkoxy group, and a C(O)O $C_{1-6}$-alkyl;
R6 represents a hydrogen atom, a methyl or an ethyl group;
n represents 0;
Z represents a bond, and
Y represents an oxygen atom.

5. The compound according to claim 1 which is selected from the group consisting of:
(+/−)2,2-Dimethyl-2,3-dihydro-benzofuran-7-carboxylic acid (4-oxo-2-pyridin-4-yl-6,7,8,9-tetrahydro-4H-pyrido[1,2-a]pyrimidin-9-yl)-amide;

(+/−)1-Methyl-1H-benzotriazole-5-carboxylic acid (4-oxo-2-pyridin-4-yl-6,7,8,9-tetrahydro-4H-pyrido[1,2-a]pyrimidin-9-yl)-amide;

(+/−)Quinoxaline-6-carboxylic acid (4-oxo-2-pyridin-4-yl-6,7,8,9-tetrahydro-4H-pyrido[1,2-a]pyrimidin-9-yl)-amide;

(+/−)2,3-Dihydro-benzofuran-7-carboxylic acid (4-oxo-2-pyrimidin-4-yl-6,7,8,9-tetrahydro-4H-pyrido[1,2-a]pyrimidin-9-yl)-amide;

(+/−)2,2-Difluoro-benzo[1,3]dioxole-4-carboxylic acid (4-oxo-2-pyridin-4-yl-6,7,8,9-tetrahydro-4H-pyrido[1,2-a]pyrimidin-9-yl)-amide;

(+/−)3,4-Dihydro-2H-benzo[b][1,4]dioxepine-6-carboxylic acid (4-oxo-2-pyridin-4-yl-6,7,8,9-tetrahydro-4H-pyrido[1,2-a]pyrimidin-9-yl)-amide;

(+/−)Benzofuran-2-carboxylic acid (4-oxo-2-pyridin-4-yl-6,7,8,9-tetrahydro-4H-pyrido[1,2-a]pyrimidin-9-yl)-amide;

(+/−)2,2-Dimethyl-2,3-dihydro-benzofuran-7-carboxylic acid (4-oxo-2-pyrimidin-4-yl-6,7,8,9-tetrahydro-4H-pyrido[1,2-a]pyrimidin-9-yl)-amide;

(+/−)8-Amino-7-chloro-2,3-dihydro-benzo[1,4]dioxine-5-carboxylic acid (4-oxo-2-pyrimidin-4-yl-6,7,8,9-tetrahydro-4H-pyrido[1,2-a]pyrimidin-9-yl)-amide;

(+/−)6-Fluoro-4H-benzo[1,3]dioxine-8-carboxylic acid (4-oxo-2-pyrimidin-4-yl-6,7,8,9-tetrahydro-4H-pyrido[1,2-a]pyrimidin-9-yl)-amide;

(+/−)6-Fluoro-4H-benzo[1,3]dioxine-8-carboxylic acid (4-oxo-2-pyridin-4-yl-6,7,8,9-tetrahydro-4H-pyrido[1,2-a]pyrimidin-9-yl)-amide;

(+/−)2,3-Dihydro-benzofuran-5-carboxylic acid (4-oxo-2-pyridin-4-yl-6,7,8,9-tetrahydro-4H-pyrido[1,2-a]pyrimidin-9-yl)-amide;

(+/−)8-Amino-7-chloro-2,3-dihydro-benzo[1,4]dioxine-5-carboxylic acid (4-oxo-2-pyridin-4-yl-6,7,8,9-tetrahydro-4H-pyrido[1,2-a]pyrimidin-9-yl)-amide;

(+/−)1-Methyl-1H-indole-3-carboxylic acid (4-oxo-2-pyridin-4-yl-6,7,8,9-tetrahydro-4H-pyrido[1,2-a]pyrimidin-9-yl)-amide;

(+/−)2-Methoxy-N-(4-oxo-2-pyridin-4-yl-6,7,8,9-tetrahydro-4H-pyrido[1,2-a]pyrimidin-9-yl)-nicotinamide;

(+/−)6,7-Dihydro-5H-[1]pyrindine-6-carboxylic acid (4-oxo-2-pyridin-4-yl-6,7,8,9-tetrahydro-4H-pyrido[1,2-a]pyrimidin-9-yl)-amide;

(+/−)2-Methoxy-N-(4-oxo-2-pyrimidin-4-yl-6,7,8,9-tetrahydro-4H-pyrido[1,2-a]pyrimidin-9-yl)-nicotinamide;

(+/−)2,6-Dimethoxy-N-(4-oxo-2-pyrimidin-4-yl-6,7,8,9-tetrahydro-4H-pyrido[1,2-a]pyrimidin-9-yl)-nicotinamide;

(+/−)N-(4-Oxo-2-pyrimidin-4-yl-6,7,8,9-tetrahydro-4H-pyrido[1,2-a]pyrimidin-9-yl)-6-(2,2,2-trifluoro-ethoxy)-nicotinamide;

(+/−)2-Fluoro-N-(4-oxo-2-pyrimidin-4-yl-6,7,8,9-tetrahydro-4H-pyrido[1,2-a]pyrimidin-9-yl)-nicotinamide;

(+/−)N-(4-Oxo-2-pyrimidin-4-yl-6,7,8,9-tetrahydro-4H-pyrido[1,2-a]pyrimidin-9-yl)-2-p-tolyloxy-nicotinamide;

(+/−)2-(4-Chloro-phenoxy)-N-(4-oxo-2-pyrimidin-4-yl-6,7,8,9-tetrahydro-4H-pyrido[1,2-a]pyrimidin-9-yl)-nicotinamide;

(+/−)2-Methylsulfanyl-N-(4-oxo-2-pyrimidin-4-yl-6,7,8,9-tetrahydro-4H-pyrido[1,2-a]pyrimidin-9-yl)-nicotinamide;

(+/−)5-Furan-2-yl-N-(4-oxo-2-pyrimidin-4-yl-6,7,8,9-tetrahydro-4H-pyrido[1,2-a]pyrimidin-9-yl)-nicotinamide;

(+/−)5-(2-Methoxy-phenyl)-N-(4-oxo-2-pyrimidin-4-yl-6,7,8,9-tetrahydro-4H-pyrido[1,2-a]pyrimidin-9-yl)-nicotinamide;

(+/−)5-(3,4-Dimethoxy-phenyl)-N-(4-oxo-2-pyrimidin-4-yl-6,7,8,9-tetrahydro-4H-pyrido[1,2-a]pyrimidin-9-yl)-nicotinamide;

(+/−)Quinoline-3-carboxylic acid (4-oxo-2-pyrimidin-4-yl-6,7,8,9-tetrahydro-4H-pyrido[1,2-a]pyrimidin-9-yl)-amide;

(+/−)N-(4-Oxo-2-pyrimidin-4-yl-6,7,8,9-tetrahydro-4H-pyrido[1,2-a]pyrimidin-9-yl)-6-thiophen-2-yl-nicotinamide;

(+/−)4-[5-(4-Oxo-2-pyrimidin-4-yl-6,7,8,9-tetrahydro-4H-pyrido[1,2-a]pyrimidin-9-ylcarbamoyl)-pyridin-2-yl]-[1,4]diazepane-1-carboxylic acid tert-butyl ester;

(+/−)6-Methyl-N-(4-oxo-2-pyrimidin-4-yl-6,7,8,9-tetrahydro-4H-pyrido[1,2-a]pyrimidin-9-yl)-nicotinamide;

(+/−)N-(4-Oxo-2-pyrimidin-4-yl-6,7,8,9-tetrahydro-4H-pyrido[1,2-a]pyrimidin-9-yl)-2-propylsulfanyl-nicotinamide;

(+/−)N-(4-Oxo-2-pyrimidin-4-yl-6,7,8,9-tetrahydro-4H-pyrido[1,2-a]pyrimidin-9-yl)-nicotinamide;

(+/−)6-Chloro-N-(4-oxo-2-pyrimidin-4-yl-6,7,8,9-tetrahydro-4H-pyrido[1,2-a]pyrimidin-9-yl)-nicotinamide;

(+/−)2-Methoxy-N-(9-methyl-4-oxo-2-pyrimidin-4-yl-6,7,8,9-tetrahydro-4H-pyrido[1,2-a]pyrimidin-9-yl)-nicotinamide;

(+/−)4-Methoxy-pyridine-2-carboxylic acid (4-oxo-2-pyrimidin-4-yl-6,7,8,9-tetrahydro-4H-pyrido[1,2-a]pyrimidin-9-yl)-amide;

(+/−)3,6-Dimethoxy-pyridazine-4-carboxylic acid (4-oxo-2-pyrimidin-4-yl-6,7,8,9-tetrahydro-4H-pyrido[1,2-a]pyrimidin-9-yl)-amide;

(+/−)Pyridine-2-carboxylic acid (4-oxo-2-pyrimidin-4-yl-6,7,8,9-tetrahydro-4H-pyrido[1,2-a]pyrimidin-9-yl)-amide;

(+/−)6-Methoxy-pyridine-2-carboxylic acid (4-oxo-2-pyrimidin-4-yl-6,7,8,9-tetrahydro-4H-pyrido[1,2-a]pyrimidin-9-yl)-amide;

(+/−)4-Methoxy-quinoline-2-carboxylic acid (4-oxo-2-pyrimidin-4-yl-6,7,8,9-tetrahydro-4H-pyrido[1,2-a]pyrimidin-9-yl)-amide;

(+/−)Isoquinoline-1-carboxylic acid (4-oxo-2-pyrimidin-4-yl-6,7,8,9-tetrahydro-4H-pyrido[1,2-a]pyrimidin-9-yl)-amide;

(+/−)5-Chloro-2-methylsulfanyl-pyrimidine-4-carboxylic acid (9-methyl-4-oxo-2-pyrimidin-4-yl-6,7,8,9-tetrahydro-4H-pyrido[1,2-a]pyrimidin-9-yl)-amide;

(+/−)[1,6]Naphthyridine-5-carboxylic acid (4-oxo-2-pyrimidin-4-yl-6,7,8,9-tetrahydro-4H-pyrido[1,2-a]pyrimidin-9-yl)-amide;

(+/−)6-Chloro-pyridine-2-carboxylic acid (4-oxo-2-pyrimidin-4-yl-6,7,8,9-tetrahydro-4H-pyrido[1,2-a]pyrimidin-9-yl)-amide;

(+/−)[1,5]Naphthyridine-2-carboxylic acid (4-oxo-2-pyrimidin-4-yl-6,7,8,9-tetrahydro-4H-pyrido[1,2-a]pyrimidin-9-yl)-amide;

(+/−)6-(2,6-Dimethoxy-phenyl)-pyridine-2-carboxylic acid (4-oxo-2-pyrimidin-4-yl-6,7,8,9-tetrahydro-4H-pyrido[1,2-a]pyrimidin-9-yl)-amide;

(+/−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide;

(+/−)8-Amino-7-chloro-2,3-dihydro-benzo[1,4]dioxine-5-carboxylic acid (9-methyl-4-oxo-2-pyrimidin-4-yl-6,7,8,9-tetrahydro-4H-pyrido[1,2-a]pyrimidin-9-yl)-amide;

(+/−)3,6-Dimethoxy-pyridazine-4-carboxylic acid (9-methyl-4-oxo-2-pyrimidin-4-yl-6,7,8,9-tetrahydro-4H-pyrido[1,2-a]pyrimidin-9-yl)-amide;

(+/−)2,2-Dimethyl-2,3-dihydro-benzofuran-7-carboxylic acid (9-methyl-4-oxo-2-pyrimidin-4-yl-6,7,8,9-tetrahydro-4H-pyrido[1,2-a]pyrimidin-9-yl)-amide;

(+/−)6-Fluoro-4H-benzo[1,3]dioxine-8-carboxylic acid (9-methyl-4-oxo-2-pyrimidin-4-yl-6,7,8,9-tetrahydro-4H-pyrido[1,2-a]pyrimidin-9-yl)-amide;

(+/−)[1,5]Naphthyridine-2-carboxylic acid (9-methyl-4-oxo-2-pyrimidin-4-yl-6,7,8,9-tetrahydro-4H-pyrido[1,2-a]pyrimidin-9-yl)-amide;

(+/−)2,3-Dihydro-benzofuran-7-carboxylic acid (9-methyl-4-oxo-2-pyrimidin-4-yl-6,7,8,9-tetrahydro-4H-pyrido[1,2-a]pyrimidin-9-yl)-amide;

(+/−)Pyridine-2-carboxylic acid (9-methyl-4-oxo-2-pyrimidin-4-yl-6,7,8,9-tetrahydro-4H-pyrido[1,2-a]pyrimidin-9-yl)-amide;

(+/−)6-Chloro-pyridine-2-carboxylic acid (9-methyl-4-oxo-2-pyrimidin-4-yl-6,7,8,9-tetrahydro-4H-pyrido[1,2-a]pyrimidin-9-yl)-amide;

(+/−)[1,6]Naphthyridine-5-carboxylic acid (9-methyl-4-oxo-2-pyrimidin-4-yl-6,7,8,9-tetrahydro-4H-pyrido[1,2-a]pyrimidin-9-yl)-amide;

(+/−)N-(9-Methyl-4-oxo-2-pyrimidin-4-yl-6,7,8,9-tetrahydro-4H-pyrido[1,2-a]pyrimidin-9-yl)-nicotinamide;

(+/−)5-Bromo-benzofuran-2-carboxylic acid (9-methyl-4-oxo-2-pyrimidin-4-yl-6,7,8,9-tetrahydro-4H-pyrido[1,2-a]pyrimidin-9-yl)-amide;

(+)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide;

(−)6-(2-Fluoro-phenyl)-pyridine-2-carboxylic acid (4-oxo-2-pyrimidin-4-yl-6,7,8,9-tetrahydro-4H-pyrido[1,2-a]pyrimidin-9-yl)-amide;

(+)2-Methoxy-N-(9-methyl-4-oxo-2-pyrimidin-4-yl-6,7,8,9-tetrahydro-4H-pyrido[1,2-a]pyrimidin-9-yl)-nicotinamide;

(−)2-Methoxy-N-(9-methyl-4-oxo-2-pyrimidin-4-yl-6,7,8,9-tetrahydro-4H-pyrido[1,2-a]pyrimidin-9-yl)-nicotinamide;

(+)[1,5]Naphthyridine-2-carboxylic acid (4-oxo-2-pyrimidin-4-yl-6,7,8,9-tetrahydro-4H-pyrido[1,2-a]pyrimidin-9-yl)-amide;

(−)[1,5]Naphthyridine-2-carboxylic acid (4-oxo-2-pyrimidin-4-yl-6,7,8,9-tetrahydro-4H-pyrido[1,2-a]pyrimidin-9-yl)-amide;

(+/−)2,2-Dimethyl-2,3-dihydro-benzofuran-7-carboxylic acid (4-oxo-2-pyridin-4-yl-4,6,7,8-tetrahydro-pyrrolo[1,2-a]pyrimidin-8-yl)-amide;

(+/−)1-Methyl-1H-benzotriazole-5-carboxylic acid (4-oxo-2-pyridin-4-yl-4,6,7,8-tetrahydro-pyrrolo[1,2-a]pyrimidin-8-yl)-amide;

(+/−)8-Amino-7-chloro-2,3-dihydro-benzo[1,4]dioxine-5-carboxylic acid (4-oxo-2-pyridin-4-yl-4,6,7,8-tetrahydro-pyrrolo[1,2-a]pyrimidin-8-yl)-amide;

(+/−)6-Fluoro-4H-benzo[1,3]dioxine-8-carboxylic acid (4-oxo-2-pyridin-4-yl-4,6,7,8-tetrahydro-pyrrolo[1,2-a]pyrimidin-8-yl)-amide;

(+/−)Quinoxaline-6-carboxylic acid (4-oxo-2-pyridin-4-yl-4,6,7,8-tetrahydro-pyrrolo[1,2-a]pyrimidin-8-yl)-amide;

(+/−)2,3-Dihydro-benzofuran-5-carboxylic acid (4-oxo-2-pyridin-4-yl-4,6,7,8-tetrahydro-pyrrolo[1,2-a]pyrimidin-8-yl)-amide;

(+/−)1-Methyl-1H-indole-3-carboxylic acid (4-oxo-2-pyridin-4-yl-4,6,7,8-tetrahydro-pyrrolo[1,2-a]pyrimidin-8-yl)-amide;

(+/−)5-Bromo-2,3-dihydro-benzofuran-7-carboxylic acid (4-oxo-2-pyridin-4-yl-4,6,7,8-tetrahydro-pyrrolo[1,2-a]pyrimidin-8-yl)-amide;

(+/−)-2,3-Dihydro-benzofuran-2-carboxylic acid (4-oxo-2-pyridin-4-yl-4,6,7,8-tetrahydro-pyrrolo[1,2-a]pyrimidin-8-yl)-amide;

(+/−)6,7-Dihydro-5H-[1]pyrindine-6-carboxylic acid (4-oxo-2-pyridin-4-yl-4,6,7,8-tetrahydro-pyrrolo[1,2-a]pyrimidin-8-yl)-amide;

(+/−)Benzofuran-2-carboxylic acid (4-oxo-2-pyridin-4-yl-4,6,7,8-tetrahydro-pyrrolo[1,2-a]pyrimidin-8-yl)-amide;

(+/−)[1,5]Naphthyridine-2-carboxylic acid (4-oxo-2-pyrimidin-4-yl-4,6,7,8-tetrahydro-pyrrolo[1,2-a]pyrimidin-8-yl)-amide;

(+/−)2-Methoxy-N-(4-oxo-2-pyrimidin-4-yl-4,6,7,8-tetrahydro-pyrrolo[1,2-a]pyrimidin-8-yl)-nicotinamide;

(+/−)5-Chloro-2-methylsulfanyl-pyrimidine-4-carboxylic acid (4-oxo-2-pyrimidin-4-yl-4,6,7,8-tetrahydro-pyrrolo[1,2-a]pyrimidin-8-yl)-amide;

(+/−)Isoquinoline-1-carboxylic acid (4-oxo-2-pyrimidin-4-yl-4,6,7,8-tetrahydro-pyrrolo[1,2-a]pyrimidin-8-yl)-amide;

(+/−)2-Methoxy-N-(4-oxo-2-pyridin-4-yl-4,6,7,8-tetrahydro-pyrrolo[1,2-a]pyrimidin-8-yl)-nicotinamide;

(+/−)5-Chloro-2-methylsulfanyl-pyrimidine-4-carboxylic acid (4-oxo-2-pyridin-4-yl-4,6,7,8-tetrahydro-pyrrolo[1,2-a]pyrimidin-8-yl)-amide;

(+/−)Isoquinoline-1-carboxylic acid (4-oxo-2-pyridin-4-yl-4,6,7,8-tetrahydro-pyrrolo[1,2-a]pyrimidin-8-yl)-amide;

(+/−)Pyridine-2-carboxylic acid (4-oxo-2-pyrimidin-4-yl-4,6,7,8-tetrahydro-pyrrolo[1,2-a]pyrimidin-8-yl)-amide;

(+/−)6-Chloro-pyridine-2-carboxylic acid (4-oxo-2-pyridin-4-yl-4,6,7,8-tetrahydro-pyrrolo[1,2-a]pyrimidin-8-yl)-amide;

(+/−)[1,5]Naphthyridine-2-carboxylic acid (4-oxo-2-pyridin-4-yl-4,6,7,8-tetrahydro-pyrrolo[1,2-a]pyrimidin-8-yl)-amide;

(+/−)8-Amino-7-chloro-2,3-dihydro-benzo[1,4]dioxine-5-carboxylic acid (4-oxo-2-pyrimidin-4-yl-4,6,7,8,9,10-hexahydro-pyrimido[1,2-a]azepin-10-yl)-amide;

(+/−)2-Methoxy-N-(4-oxo-2-pyrimidin-4-yl-4,6,7,8,9,10-hexahydro-pyrimido[1,2-a]azepin-0-yl)-nicotinamide;

(+/−)5-Bromo-2,3-dihydro-benzofuran-7-carboxylic acid (4-oxo-2-pyrimidin-4-yl-4,6,7,8,9,10-hexahydro-pyrimido[1,2-a]azepin-10-yl)-amide;

(+/−)6-Fluoro-4H-benzo[1,3]dioxine-8-carboxylic acid (4-oxo-2-pyrimidin-4-yl-4,6,7,8,9,10-hexahydro-pyrimido[1,2-a]azepin-10-yl)-amide;

(+/−)5-Chloro-2,3-dihydro-benzofuran-7-carboxylic acid (4-oxo-2-pyrimidin-4-yl-4,6,7,8,9,10-hexahydro-pyrimido[1,2-a]azepin-10-yl)-amide;

(+/−)2,3-Dihydro-benzofuran-7-carboxylic acid (4-oxo-2-pyrimidin-4-yl-4,6,7,8,9,10-hexahydro-pyrimido[1,2-a]azepin-10-yl)-amide;

(+/−)2,2-Dimethyl-2,3-dihydro-benzofuran-7-carboxylic acid (4-oxo-2-pyrimidin-4-yl-4,6,7,8,9,10-hexahydro-pyrimido[1,2-a]azepin-10-yl)-amide;
(+/−)2,2-Dimethyl-2,3-dihydro-benzofuran-7-carboxylic acid (4-oxo-2-pyridin-4-yl-4,6,7,8,9,10-hexahydro-pyrimido[1,2-a]azepin-10-yl)-amide;
(+/−)6-Fluoro-4H-benzo[1,3]dioxine-8-carboxylic acid (4-oxo-2-pyridin-4-yl-4,6,7,8,9,10-hexahydro-pyrimido[1,2-a]azepin-10-yl)-amide;
(+/−)5-Chloro-2,3-dihydro-benzofuran-7-carboxylic acid (4-oxo -2-pyridin-4-yl-4,6,7,8,9,10-hexahydro-pyrimido[1,2-a]azepin-10-yl)-amide;
(+/−)2,3-Dihydro-benzofuran-7-carboxylic acid (4-oxo-2-pyridin -4-yl-4,6,7,8,9,10-hexahydro-pyrimido[1,2-a]azepin-10-yl)-amide;
(+/−)8-Amino-7-chloro-2,3-dihydro-benzo[1,4]dioxine-5-carboxylic acid (4-oxo-2-pyridin-4-yl-4,6,7,8,9,10-hexahydro-pyrimido[1,2-a]azepin-10-yl) -amide;
(+/−)2-Methoxy-N-(4-oxo-2-pyridin-4-yl-4,6,7,8,9,10-hexahydro-pyrimido[1,2-a]azepin-10-yl)-nicotinamide;
(+)2-Methoxy-N-(4-oxo-2-pyrimidin-4-yl-4,6,7,8,9,10-hexahydro-pyrimido[1,2-a]azepin-10-yl)-nicotinamide;
(−)2-Methoxy-N-(4-oxo-2-pyrimidin-4-yl-4,6,7,8,9,10-hexahydro-pyrimido[1,2-a]azepin-10-yl)-nicotinamide;
(+/−)2,6-Dimethoxy-N-(4-oxo-2-pyridin-4-yl-4,6,7,8,9,10-hexahydro-pyrimido[1,2-a]azepin-10-yl)-nicotinamide;
(+/−)N-(4-Oxo-2-pyridin-4-yl-4,6,7,8,9,10-hexahydro-pyrimido[1,2-a]azepin-10-yl)-6-(2,2,2-trifluoro-ethoxy)-nicotinamide;
(+/−)2-Fluoro-N-(4-oxo-2-pyridin-4-yl-4,6,7,8,9,10-hexahydro-pyrimido[1,2-a]azepin-10-yl)-nicotinamide;
(+/−)2-Methylsulfanyl-N-(4-oxo-2-pyridin-4-yl-4,6,7,8,9,10-hexahydro-pyrimido[1,2-a]azepin-10-yl)-nicotinamide;
(+/−)N-(4-Oxo-2-pyridin-4-yl-4,6,7,8,9,10-hexahydro-pyrimido[1,2-a]azepin-10-yl)-2-p-tolyloxy-nicotinamide;
(+/−)2-(4-Chloro-phenoxy)-N-(4-oxo-2-pyridin-4-yl-4,6,7,8,9,10-hexahydro-pyrimido[1,2-a]azepin-10-yl)-nicotinamide;
(+/−)3H-Imidazo[4,5-b]pyridine-6-carboxylic acid (4-oxo-2-pyridin-4-yl-4,6,7,8,9,10-hexahydro-pyrimido[1,2-a]azepin-10-yl)-amide;
(+/−)N-(4-Oxo-2-pyridin-4-yl-4,6,7,8,9,10-hexahydro-pyrimido[1,2-a]azepin-10-yl)-6-thiophen-2-yl-nicotinamide;
(+/−)6-Methyl-N-(4-oxo-2-pyridin-4-yl-4,6,7,8,9,10-hexahydro-pyrimido[1,2-a]azepin-10-yl)-nicotinamide;
(+/−)5-Furan-2-yl-N-(4-oxo-2-pyridin-4-yl-4,6,7,8,9,10-hexahydro-pyrimido[1,2-a]azepin-10-yl)-nicotinamide;
(+/−)5-(2-Methoxy-phenyl)-N-(4-oxo-2-pyridin-4-yl-4,6,7,8,9,10-hexahydro-pyrimido[1,2-a]azepin-10-yl)-nicotinamide;
(+/−)5-(3,4-Dimethoxy-phenyl)-N-(4-oxo-2-pyridin-4-yl-4,6,7,8,9,10-hexahydro-pyrimido[1,2-a]azepin-10-yl)-nicotinamide;
(+/−)Quinoline-3-carboxylic acid (4-oxo-2-pyridin-4-yl-4,6,7,8,9,10-hexahydro-pyrimido[1,2-a]azepin-10-yl)-amide;
(+/−)4-[5-(4-Oxo-2-pyridin-4-yl-4,6,7,8,9,10-hexahydro-pyrimido[1,2-a]azepin-10-ylcarbamoyl)-pyridin-2-yl]-[1,4]diazepane-1-carboxylic acid tert-butyl ester;
(+/−)5-(4-Bromo-phenyl)-N-(4-oxo-2-pyridin-4-yl-4,6,7,8,9,10-hexahydro-pyrimido[1,2-a]azepin-10-yl)-nicotinamide;
(+/−)N-(4-Oxo-2-pyridin-4-yl-4,6,7,8,9,10-hexahydro-pyrimido[1,2-a]azepin-1 0-yl)-nicotinamide;
(+/−)6-Chloro-N-(4-oxo-2-pyridin-4-yl-4,6,7,8,9,10-hexahydro-pyrimido[1,2-a]azepin-10-yl)-nicotinamide;
(+/−)2-Chloro-N-(4-oxo-2-pyridin-4-yl-4,6,7,8,9,10-hexahydro-pyrimido[1,2-a]azepin-10-yl)-nicotinamide;
(+/−)N-(4-Oxo-2-pyridin-4-yl-4,6,7,8,9,10-hexahydro-pyrimido[1,2-a]azepin-10-yl)-2-phenylsulfanyl-nicotinamide
(+/−)N-(4-Oxo-2-pyridin-4-yl-4,6,7,8,9,10-hexahydro-pyrimido[1,2-a]azepin-10-yl)-2-propylsulfanyl-nicotinamide;
(+/−)2-(4-Chloro-phenylsulfanyl)-N-(4-oxo-2-pyridin-4-yl -4,6,7,8,9,10-hexahydro-pyrimido[1,2-a]azepin-10-yl)-nicotinamide;
(+/−)4-Methyl-2-phenyl-pyrimidine-5-carboxylic acid (4-oxo-2-pyrimidin-4-yl-4,6,7,8,9,10-hexahydro-pyrimido[1,2-a]azepin-10-yl)-amide;
(+/−)Pyrimidine-5-carboxylic acid (4-oxo-2-pyrimidin-4-yl-4,6,7,8,9,10-hexahydro-pyrimido[1,2-a]azepin-10-yl)-amide;
(+/−)5-Chloro-2-methylsulfanyl-pyrimidine-4-carboxylic acid (4-oxo-2-pyrimidin-4-yl-4,6,7,8,9,10-hexahydro-pyrimido[1,2-a]azepin-10-yl)-amide;
(+/−)Pyridazine-4-carboxylic acid (4-oxo-2-pyrimidin-4-yl-4,6,7,8,9,10-hexahydro-pyrimido[1,2-a]azepin-10-yl)-amide;
(+/−)6-Phenyl-pyrimidine-4-carboxylic acid (4-oxo-2-pyrimidin -4-yl-4,6,7,8,9,10-hexahydro-pyrimido[1,2-a]azepin-10-yl)-amide;
(+/−)Cinnoline-4-carboxylic acid (4-oxo-2-pyrimidin-4-yl-4,6,7,8,9,10-hexahydro-pyrimido[1,2-a]azepin-10-yl)-amide;
(+/−)3,6-Dimethoxy-pyridazine-4-carboxylic acid (4-oxo-2-pyrimidin-4-yl-4,6,7,8,9,10-hexahydro-pyrimido[1,2-a]azepin-10-yl)-amide;
(+/−)Isoquinoline-1-carboxylic acid (4-oxo-2-pyridin-4-yl-4,6,7,8,9,10-hexahydro-pyrimido[1,2-a]azepin-10-yl)-amide;
(+/−)3-Phenyl-cinnoline-4-carboxylic acid (4-oxo-2-pyrimidin-4-yl-4,6,7,8,9,10-hexahydro-pyrimido[1,2-a]azepin-10-yl)-amide;
(+/−)[1,6]Naphthyridine-5-carboxylic acid (4-oxo-2-pyridin -4-yl-4,6,7,8,9,10-hexahydro-pyrimido[1,2-a]azepin-10-yl)-amide;
(+/−)[1,5]Naphthyridine-2-carboxylic acid (4-oxo-2-pyridin -4-yl-4,6,7,8,9,10-hexahydro-pyrimido[1,2-a]azepin-10-yl)-amide;
(+/−)[1,6]Naphthyridine-5-carboxylic acid (4-oxo-2-pyrimidin-4-yl-4,6,7,8,9,10-hexahydro-pyrimido[1,2-a]azepin-10-yl)-amide;
(+/−)[1,5]Naphthyridine-2-carboxylic acid (4-oxo-2-pyrimidin-4-yl-4,6,7,8,9,10-hexahydro-pyrimido[1,2-a]azepin-10-yl)-amide;
(+/−)4-Methoxy-quinoline-2-carboxylic acid (4-oxo-2-pyrimidin -4-yl-4,6,7,8,9,10-hexahydro-pyrimido[1,2-a]azepin-10-yl)-amide;

(+/−)Isoquinoline-1-carboxylic acid (4-oxo-2-pyrimidin-4-yl-4,6,7,8,9,10-hexahydro-pyrimido[1,2-a]azepin-10-yl)-amide;
(+/−)Pyridine-2-carboxylic acid (4-oxo-2-pyrimidin-4-yl-4,6,7,8,9,10-hexahydro-pyrimido[1,2-a]azepin-10-yl)-amide;
(+/−)6-Chloro-pyridine-2-carboxylic acid (4-oxo-2-pyrimidin-4-yl-4,6,7,8,9,10-hexahydro-pyrimido[1,2-a]azepin-10-yl)-amide;
(+/−)4-Methoxy-pyridine-2-carboxylic acid (4-oxo-2-pyrimidin-4-yl-4,6,7,8,9,10-hexahydro-pyrimido[1,2-a]azepin-10-yl)-amide;
(+/−)3,5-Difluoro-pyridine-2-carboxylic acid (4-oxo-2-pyrimidin-4-yl-4,6,7,8,9,10-hexahydro-pyrimido[1,2-a]azepin-10-yl)-amide;
(+/−)6-(2,6-Dimethoxy-phenyl)-pyridine-2-carboxylic acid (4-oxo-2-pyrimidin-4-yl-4,6,7,8,9,10-hexahydro-pyrimido[1,2-a]azepin-10-yl)-amide;
(+/−)4-Methyl-2-phenyl-pyrimidine-5-carboxylic acid (4-oxo-2-pyridin-4-yl-4,6,7,8,9,10-hexahydro-pyrimido[1,2-a]azepin-10-yl)-amide;
(+/−)3-Phenyl-cinnoline-4-carboxylic acid (4-oxo-2-pyridin-4-yl-4,6,7,8,9,10-hexahydro-pyrimido[1,2-a]azepin-10-yl)-amide;
(+/−)3,6-Dimethoxy-pyridazine-4-carboxylic acid (4-oxo-2-pyridin-4-yl-4,6,7,8,9,10-hexahydro-pyrimido[1,2-a]azepin-10-yl)-amide;
(+/−)2-Methyl-4-phenyl-pyrimidine-5-carboxylic acid (4-oxo-2-pyridin-4-yl-4,6,7,8,9,10-hexahydro-pyrimido[1,2-a]azepin-10-yl)-amide;
(+/−)6-Phenyl-pyrimidine-4-carboxylic acid (4-oxo-2-pyridin-4-yl-4,6,7,8,9,10-hexahydro-pyrimido[1,2-a]azepin-10-yl)-amide;
(+/−)6-(2-Fluoro-phenyl)-pyridine-2-carboxylic acid (4-oxo-2-pyrimidin-4-yl-4,6,7,8,9,10-hexahydro-pyrimido[1,2-a]azepin-10-yl)-amide;
(+/−)2,6-Dimethoxy-N-(4-oxo-2-pyrimidin-4-yl-4,6,7,8,9,10-hexahydro-pyrimido[1,2-a]azepin-10-yl)-nicotinamide;
(+/−)N-(4-Oxo-2-pyrimidin-4-yl-4,6,7,8,9,10-hexahydro-pyrimido[1,2-a]azepin-10-yl)-6-(2,2,2-trifluoro-ethoxy)-nicotinamide;
(+/−)2-Fluoro-N-(4-oxo-2-pyrimidin-4-yl-4,6,7,8,9,10-hexahydro-pyrimido[1,2-a]azepin-10-yl)-nicotinamide;
(+/−)5-Furan-2-yl-N-(4-oxo-2-pyrimidin-4-yl-4,6,7,8,9,10-hexahydro-pyrimido[1,2-a]azepin-10-yl)-nicotinamide;
(+/−)6-Methoxy-pyridine-2-carboxylic acid (4-oxo-2-pyrimidin-4-yl-4,6,7,8,9,10-hexahydro-pyrimido[1,2-a]azepin-10-yl)-amide;
(+/−)Quinoline-3-carboxylic acid (4-oxo-2-pyrimidin-4-yl-4,6,7,8,9,10-hexahydro-pyrimido[1,2-a]azepin-10-yl)-amide;
(+/−)4-[5-(4-Oxo-2-pyrimidin-4-yl-4,6,7,8,9,10-hexahydro-pyrimido[1,2-a]azepin-10-ylcarbamoyl)-pyridin-2-yl]-[1,4]diazepane-1-carboxylic acid tert-butyl ester;
(+/−)5-(2-Methoxy-phenyl)-N-(4-oxo-2-pyrimidin-4-yl-4,6,7,8,9,10-hexahydro-pyrimido[1,2-a]azepin-10-yl)-nicotinamide;
(+/−)5-(3,4-Dimethoxy-phenyl)-N-(4-oxo-2-pyrimidin-4-yl -4,6,7,8,9,10-hexahydro-pyrimido[1,2-a]azepin-10-yl)-nicotinamide;
(+/−)2,6-Dimethoxy-pyrimidine-4-carboxylic acid (4-oxo-2-pyrimidin-4-yl-4,6,7,8,9,10-hexahydro-pyrimido[1,2-a]azepin-10-yl)-amide;
(+/−)5-Bromo-2-methylsulfanyl-pyrimidine-4-carboxylic acid (4-oxo-2-pyrimidin-4-yl-4,6,7,8,9,10-hexahydro-pyrimido[1,2-a]azepin-10-yl)-amide;
(+/−)[1,5]Naphthyridine-2-carboxylic acid (10-methyl-4-oxo -2-pyrimidin-4-yl-4,6,7,8,9,10-hexahydro-pyrimido[1,2-a]azepin-10-yl)-amide;
(+/−)6-Methoxy-pyridine-2-carboxylic acid (10-methyl-4-oxo-2-pyrimidin-4-yl-4,6,7,8,9,10-hexahydro-pyrimido[1,2-a]azepin-10-yl)-amide;
(+/−)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide;
(+/−)N-(10-Ethyl-4-oxo-2-pyrimidin-4-yl-4,6,7,8,9,10-hexahydro-pyrimido[1,2-a]azepin-10-yl)-2-methoxy-nicotinamide;
(+/−)2-Methoxy-N-(10-methyl-4-oxo-2-pyridin-4-yl-4,6,7,8,9,10-hexahydro-pyrimido[1,2-a]azepin-10-yl)-nicotinamide;
(+/−)2,3-Dihydro-benzofuran-7-carboxylic acid (10-methyl-4-oxo -2-pyridin-4-yl-4,6,7,8,9,10-hexahydro-pyrimido[1,2-a]azepin-10-yl)-amide;
(+/−)2-Methoxy-N-(10-methyl-4-oxo-2-pyrimidin-4-yl-4,6,7,8,9,10-hexahydro-pyrimido[1,2-a]azepin-10-yl)-nicotinamide;
(+/−)2,3-Dihydro-benzofuran-7-carboxylic acid (10-methyl-4-oxo -2-pyrimidin-4-yl-4,6,7,8,9,10-hexahydro-pyrimido[1,2-a]azepin-10-yl)-amide;
(+/−)6-Fluoro-4H-benzo[1,3]dioxine-8-carboxylic acid (10-methyl-4-oxo-2-pyrimidin-4-yl-4,6,7,8,9,10-hexahydro-pyrimido[1,2-a]azepin-10-yl)-amide;
(+/−)2,6-Dimethoxy-N-(10-methyl-4-oxo-2-pyrimidin-4-yl-4,6,7,8,9,10-hexahydro-pyrimido[1,2-a]azepin-10-yl)-nicotinamide;
(+/−)Pyridine-2-carboxylic acid (10-methyl-4-oxo-2-pyrimidin-4-yl-4,6,7,8,9,10-hexahydro-pyrimido[1,2-a]azepin-10-yl)-amide;
(+/−)4-Methoxy-pyridine-2-carboxylic acid (10-methyl-4-oxo-2-pyrimidin-4-yl-4,6,7,8,9,10-hexahydro-pyrimido[1,2-a]azepin-10-yl)-amide;
(+/−)3,6-Dimethoxy-pyridazine-4-carboxylic acid (10-methyl-4-oxo-2-pyrimidin-4-yl-4,6,7,8,9,10-hexahydro-pyrimido[1,2-a]azepin-10-yl)-amide;
(+/−)6-Chloro-pyridine-2-carboxylic acid (10-methyl-4-oxo-2-pyrimidin-4-yl-4,6,7,8,9,10-hexahydro-pyrimido[1,2-a]azepin-10-yl)-amide;
(+/−)8-Amino-7-chloro-2,3-dihydro-benzo[1,4]dioxine-5-carboxylic acid (10-methyl-4-oxo-2-pyrimidin-4-yl-4,6,7,8,9,10-hexahydro-pyrimido[1,2-a]azepin-0-yl)-amide;
(+/−)5-Bromo-2-methylsulfanyl-pyrimidine-4-carboxylic acid (10-methyl-4-oxo-2-pyrimidin-4-yl-4,6,7,8,9,10-hexahydro-pyrimido[1,2-a]azepin-10-yl) -amide;
(+/−)6-Bromo-pyridine-2-carboxylic acid (10-methyl-4-oxo-2-pyrimidin-4-yl-4,6,7,8,9,10-hexahydro-pyrimido[1,2-a]azepin-10-yl)-amide;
(+/−)3,5-Difluoro-pyridine-2-carboxylic acid (10-methyl-4-oxo -2-pyrimidin-4-yl-4,6,7,8,9,10-hexahydro-pyrimido[1,2-a]azepin-10-yl)-amide;
(+/−)2,2-Dimethyl-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl) -amide;
(+/−)4-Methoxy-pyridine-2-carboxylic acid (10-ethyl-4-oxo-2-pyrimidin-4-yl-4,6,7,8,9,10-hexahydro-pyrimido[1,2-a]azepin-10-yl)-amide;
(+/−)5-Chloro-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide;

(+/−)5-Chloro-2-methylsulfanyl-pyrimidine-4-carboxylic acid (10-methyl-4-oxo-2-pyrimidin-4-yl-4,6,7,8,9,10-hexahydro-pyrimido[1,2-a]azepin-10-yl) -amide;

(+/−)8-Amino-7-chloro-2,3-dihydro-benzo[1,4]dioxine-5-carboxylic acid (10-ethyl-4-oxo-2-pyrimidin-4-yl-4,6,7,8,9,10-hexahydro-pyrimido[1,2-a]azepin-10-yl)-amide;

(+/−)3,6-Dimethoxy-pyridazine-4-carboxylic acid (10-ethyl-4-oxo-2-pyrimidin-4-yl-4,6,7,8,9,10-hexahydro-pyrimido[1,2-a]azepin-10-yl)-amide;

(+/−)6-Fluoro-4H-benzo[1,3]dioxine-8-carboxylic acid (10-ethyl-4-oxo-2-pyrimidin-4-yl-4,6,7,8,9,10-hexahydro-pyrimido[1,2-a]azepin-10-yl)-amide;

(+/−)N-(10-Ethyl-4-oxo-2-pyrimidin-4-yl-4,6,7,8,9,10-hexahydro-pyrimido[1,2-a]azepin-10-yl)-2,6-dimethoxy-nicotinamide;

(+/−)N-(3-Bromo-4-oxo-2-pyrimidin-4-yl-4,6,7,8,9,10-hexahydro-pyrimido[1,2-a]azepin-10-yl)-2-methoxy-nicotinamide;

(+/−)6-Chloro-pyridine-2-carboxylic acid (10-ethyl-4-oxo-2-pyrimidin-4-yl-4,6,7,8,9,10-hexahydro-pyrimido[1,2-a]azepin-10-yl)-amide;

(+)2,6-Dimethoxy-N-(4-oxo-2-pyrimidin-4-yl-4,6,7,8,9,10-hexahydro-pyrimido[1,2-a]azepin-10-yl)-nicotinamide;

(−)2,6-Dimethoxy-N-(4-oxo-2-pyrimidin-4-yl-4,6,7,8,9,10-hexahydro-pyrimido[1,2-a]azepin-10-yl)-nicotinamide;

(+)2-Methoxy-N-(10-methyl-4-oxo-2-pyrimidin-4-yl-4,6,7,8,9,10-hexahydro-pyrimido[1,2-a]azepin-10-yl)-nicotinamide;

(−)2,6-Dimethoxy-N-(10-methyl-4-oxo-2-pyrimidin-4-yl-4,6,7,8,9,10-hexahydro-pyrimido[1,2-a]azepin-10-yl)-nicotinamide;

(−)2-Methoxy-N-(10-methyl-4-oxo-2-pyrimidin-4-yl-4,6,7,8,9,10-hexahydro-pyrimido[1,2-a]azepin-10-yl)-nicotinamide;

(+)2,6-Dimethoxy-N-(10-methyl-4-oxo-2-pyrimidin-4-yl-4,6,7,8,9,10-hexahydro-pyrimido[1,2-a]azepin-10-yl)-nicotinamide;

(−)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide; and (+)5-Bromo-2,3-dihydro-benzofuran-7-carboxylic acid (10-methyl-4-oxo-2-pyrimidin-4-yl-4,6,7,8,9,10-hexahydro-pyrimido[1,2-a]azepin-10-yl)-amide;

or a salt thereof.

6. A pharmaceutical composition comprising a compound of formula (I) or a pharmaceutically acceptable salt thereof according to claim 1 in combination with at least one pharmaceutically acceptable excipient.

7. A pharmaceutical composition comprising a compound of formula (I) or a pharmaceutically acceptable salt thereof according to claim 2 in combination with at least one pharmaceutically acceptable excipient.

8. A pharmaceutical composition comprising a compound of formula (I) or a pharmaceutically acceptable salt thereof according to claim 3 in combination with at least one pharmaceutically acceptable excipient.

9. A pharmaceutical composition comprising a compound of formula (I) or a pharmaceutically acceptable salt thereof according to claim 4 in combination with at least one pharmaceutically acceptable excipient.

10. A pharmaceutical composition comprising a compound of formula (I) or a pharmaceutically acceptable salt thereof according to claim 5 in combination with at least one pharmaceutically acceptable excipient.

\* \* \* \* \*

UNITED STATES PATENT AND TRADEMARK OFFICE
CERTIFICATE OF CORRECTION

PATENT NO. : 8,198,287 B2
APPLICATION NO. : 12/487270
DATED : June 12, 2012
INVENTOR(S) : Aude Fayol et al.

It is certified that error appears in the above-identified patent and that said Letters Patent is hereby corrected as shown below:

Title Page Item (73) should read:

(73) Assignees: Sanofi-Aventis, Paris (FR); Mitsubishi Tanabe Pharma Corporation, Osaka (JP)

Signed and Sealed this
Fourteenth Day of May, 2013

Teresa Stanek Rea
*Acting Director of the United States Patent and Trademark Office*